(12) United States Patent
Wei et al.

(10) Patent No.: US 12,228,568 B2
(45) Date of Patent: Feb. 18, 2025

(54) REDOX-LABILE FLUORESCENT PROBES AND THEIR SURFACE IMMOBILIZATION METHODS FOR THE DETECTION OF METABOLITES

(71) Applicant: The Regents of the University of California, Oakland, CA (US)

(72) Inventors: Wei Wei, Seattle, WA (US); Min Xue, Chino Hills, CA (US); Zhonghan Li, Portland, OR (US); Hanjun Cheng, Seattle, WA (US)

(73) Assignee: The Regents of the University of California, Oakland, CA (US)

( * ) Notice: Subject to any disclaimer, the term of this patent is extended or adjusted under 35 U.S.C. 154(b) by 1044 days.

(21) Appl. No.: 17/258,427

(22) PCT Filed: Jul. 8, 2019

(86) PCT No.: PCT/US2019/040872
§ 371 (c)(1),
(2) Date: Jan. 6, 2021

(87) PCT Pub. No.: WO2020/014153
PCT Pub. Date: Jan. 16, 2020

(65) Prior Publication Data
US 2021/0278401 A1 Sep. 9, 2021

Related U.S. Application Data

(60) Provisional application No. 62/695,699, filed on Jul. 9, 2018.

(51) Int. Cl.
*G01N 33/543* (2006.01)
*B01L 3/00* (2006.01)
*C09B 62/78* (2006.01)
*C09K 11/07* (2006.01)
*C12Q 1/26* (2006.01)
*C12Q 1/32* (2006.01)

(52) U.S. Cl.
CPC .. *G01N 33/54353* (2013.01); *B01L 3/502761* (2013.01); *C09B 62/78* (2013.01); *C09K 11/07* (2013.01); *C12Q 1/26* (2013.01); *C12Q 1/32* (2013.01); *B01L 2200/16* (2013.01); *B01L 2300/0636* (2013.01); *B01L 2300/0819* (2013.01); *B01L 2300/0829* (2013.01); *B01L 2300/0867* (2013.01); *B01L 2300/0893* (2013.01); *B01L 2300/123* (2013.01); *C09K 2211/1018* (2013.01)

(58) Field of Classification Search
CPC ......... B01L 2200/16; B01L 2300/0636; B01L 2300/0819; B01L 2300/0829; B01L 2300/0867; B01L 2300/0893; B01L 2300/0896; B01L 2300/123; B01L 2400/06; B01L 3/502761; C09B 62/78; C09K 11/07; C09K 2211/1018; C12Q 1/26; C12Q 1/32; G01N 33/532; G01N 33/54353
See application file for complete search history.

(56) References Cited

U.S. PATENT DOCUMENTS

| | | | |
|---|---|---|---|
| 6,703,216 B2 | 3/2004 | Parsons et al. | |
| 6,982,152 B2* | 1/2006 | Riss | G01N 33/5014 |
| | | | 435/25 |
| 7,989,188 B2 | 8/2011 | Gengrinovitch et al. | |
| 2012/0021951 A1 | 1/2012 | Hess et al. | |
| 2013/0053252 A1 | 2/2013 | Xie et al. | |
| 2013/0130289 A1* | 5/2013 | Benink | G01N 33/582 |
| | | | 435/8 |
| 2015/0219654 A1* | 8/2015 | Naleway | G01N 33/5076 |
| | | | 530/328 |
| 2016/0054303 A1 | 2/2016 | Hanson | |
| 2017/0037248 A1* | 2/2017 | Batchelor | C09B 19/00 |

OTHER PUBLICATIONS

Cheng et al., "Single-cell profiling of D-2-hydroxyglutarate using surface-immobilized resazurin analogs," Biosens. Bioelectron., Oct. 15, 2021, 190:113368; Epub May 29, 2021, pp. 1-9.*
Supplementary Material, pp. 1-11 to Cheng et al., "Single-cell profiling of D-2-hydroxyglutarate using surface-immobilized resazurin analogs," Biosens. Bioelectron., Oct. 15, 2021, 190:113368; Epub May 29, 2021, pp. 1-9.*
Stapleton et al., "Development of an In Vitro Compartmentalization Screen for High-Throughput Directed Evolution of [FeFe] Hydrogenases," 2010, PLoS One, vol. 5, issue 12, e15275, pp. 1-8.*
User Guide, "Thermo Scientific™ Pierce™ Biotin-Fluorescein Conjugate," Jan. 2015, retrieved from https://www.fishersci.com/shop/products/pierce-biotin-conjugated-proteins-molecules-1/PI22030 on May 13, 2024.*
Amir El-Ad D., et al., "ViSNE Enables Visualization of High Dimensional Single-cell Data and Reveals Phenotypic Heterogeneity of Leukemia," Nature biotechnology, 2013, vol. 31 (6), pp. 545-552.
Bendall S C., et al., "Single-cell Trajectory Detection Uncovers Progression and Regulatory Coordination in Human B Cell Development," Cell, 2014, vol. 157 (3), pp. 714-725.
Cairns R A., et al., "Regulation of Cancer Cell Metabolism," Nature Reviews. Cancer, 2011, vol. 11 (2), pp. 85-95.
Candeias L P., et al., "The Catalysed NADH Reduction of Resazurin to Resorufin," Journal of the Chemical Society, 1998, vol. 2, pp. 2333-2334.
Eyer K., et al., "A Microchamber Array for Single Cell Isolation and Analysis of Intracellular Biomolecules," Lab on a Chip, 2012, vol. 12 (4), pp. 765-772.

(Continued)

*Primary Examiner* — Galina M. Yakovleva
(74) *Attorney, Agent, or Firm* — Suzannah K. Sundby, Esq.; Canady + Lortz LLP

(57) ABSTRACT

Disclosed herein is an analytical method for profiling lactate (or other analyte) production in single cells, via the use of coupled enzyme reactions on surface-grafted resazurin/resorufin molecules is provided. Additionally surface-bound resazurin/resorufin that retains redox indicator activity as well as microfluidic devices comprising such surface-bound resazurin/resorufin indicators are provided.

23 Claims, 44 Drawing Sheets
Specification includes a Sequence Listing.

(56) References Cited

OTHER PUBLICATIONS

Hanahan D., et al., "Hallmarks of Cancer: The Next Generation," Leading Edge Review, Cell, 2011, vol. 144, pp. 646-674.
Hitosugi T., et al., "Post-translational Modifications and the Warburg Effect," Oncogene, 2014, vol. 33 (34), pp. 4279-4285.
International Preliminary Report on Patentability and Written Opinion dated Jan. 21, 2021 in PCT Application No. PCT/US2019/040872.
International Search Report and Written Opinion dated Nov. 14, 2019 in PCT Application No. PCT/US2019/040872.
Ito K., et al., "Metabolic Requirements for the Maintenance of Self-renewing Stem Cells," Nature Reviews. Molecular Cell Biology, 2014, vol. 15 (4), pp. 243-256.
Jewett J.C., et al., "Cu-free Click Cycloaddition Reactions in Chemical Biology," Chemical Society Reviews, 2010, vol. 39 (4), pp. 1272-1279.
Kohli L., et al., "Surviving Change: the Metabolic Journey of Hematopoietic Stem Cells," Trends in Cell Biology, 2014, vol. 24 (8), pp. 479-487.
Levine J H., et al., "Data-driven Phenotypic Dissection of Aml Reveals Progenitor-like Cells That Correlate With Prognosis," Cell, 2015, vol. 162 (1), pp. 1-14.
Li Z., et al., "Surface Immobilization of Redox-Labile Fluorescent Probes Enables Single-Cell Co-Profiling of Aerobic Glycolysis and Oncogenic Protein Signaling Activities," Angewandte Chemie, 2018, vol. 57 (36), pp. 1-13.
Locasale J W., et al., "Metabolic Flux and the Regulation of Mammalian Cell Growth," Cell Metabolism Review, 2011, vol. 14, pp. 443-451.
Lunt S Y., et al., "Aerobic Glycolysis: Meeting the Metabolic Requirements of Cell Proliferation," Annual review of cell and developmental biology, 2011, vol. 27, pp. 441-464.
McGranahan N., et al., "Clonal Heterogeneity and Tumor Evolution: Past, Present, and the Future," Cell, 2017, vol. 168 (4), pp. 613-628.
O'Brien J., et al., "Investigation of the Alamar Blue (resazurin) Fluorescent Dye for the Assessment of Mammalian Cell Cytotoxicity," European Journal of Biochemistry, 2000, vol. 267 (17), pp. 5421-5426.
Palomino J., et al., "Resazurin Microtiter Assay Plate: Simple and Inexpensive Method for Detection of Drug Resistance in *Mycobacterium tuberculosis*," Antimicrobial Agents and Chemotherapy, 2002, vol. 46 (8), pp. 2720-2722.
Park J H., et al., "Erlotinib Binds Both Inactive and Active Conformations of the EGFR Tyrosine Kinase Domain," The Biochemical journal, 2012, vol. 448 (3), pp. 417-423.
Shi Q., et al., "Single-cell Proteomic Chip for Profiling Intracellular Signaling Pathways in Single Tumor Cells," Proceedings of the National Academy of Sciences of the United States of America, 2012, vol. 109 (2), pp. 419-424.
TeSlaa T., et al., "Techniques to Monitor Glycolysis," Methods in Enzymology, 2014, vol. 542, pp. 91-114.
Xue M., et al., "Chemical Methods for the Simultaneous Quantitation of Metabolites and Proteins From Single Cells," Journal of the American Chemical Society, 2015, vol. 137 (12), pp. 4066-4069.
Xue M., et al., "Supramolecular Probes for Assessing Glutamine Uptake Enable Semi-quantitative Metabolic Models in Single Cells," Journal of the American Chemical Society, 2016, vol. 138 (9), pp. 3085-3093.
Zhao Y., et al., "Genetically Encoded Fluorescent Sensors for Intracellular NADH Detection," Cell Metabolism, 2011, vol. 14 (4), pp. 555-566.
Zheng X., et al., "Optical Detection of Single Cell Lactate Release for Cancer Metabolic Analysis," Analytical Chemistry, 2010, vol. 82 (12), pp. 5082-5087.

\* cited by examiner

A

B

F
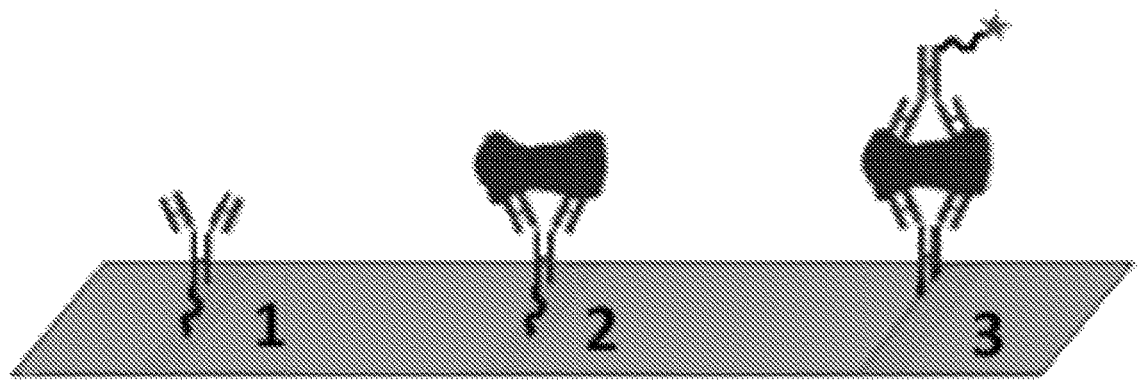
Protein detection – sandwich immunofluorescence
G
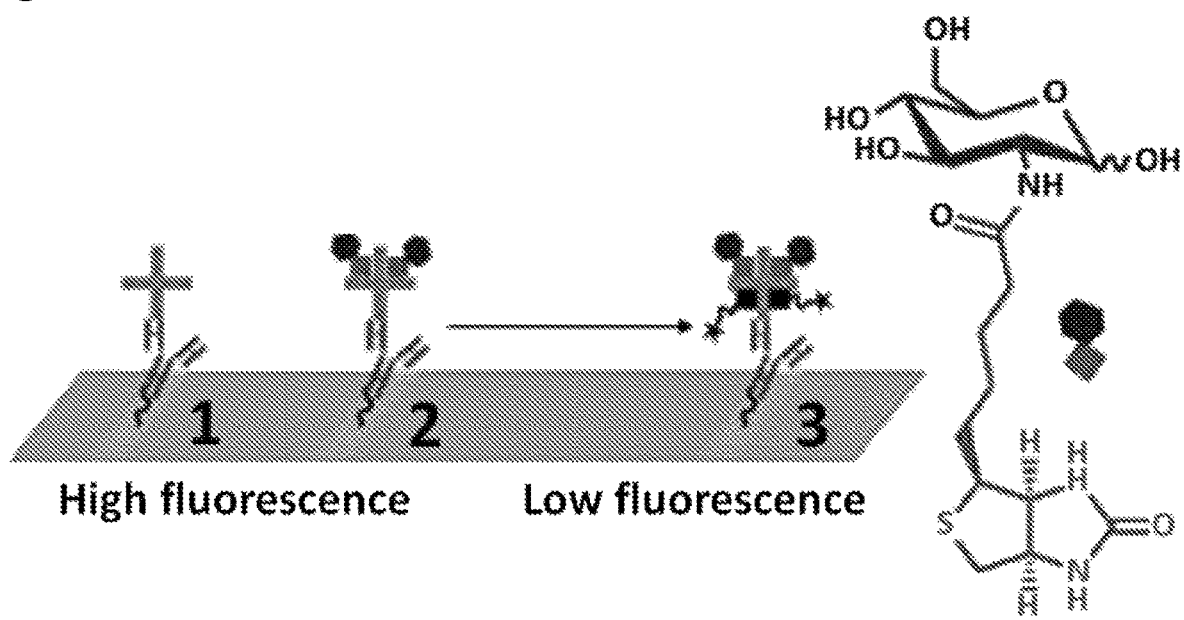
Glucose uptake detection – competitive FRET assay
*Fig. 18, cont'd.*

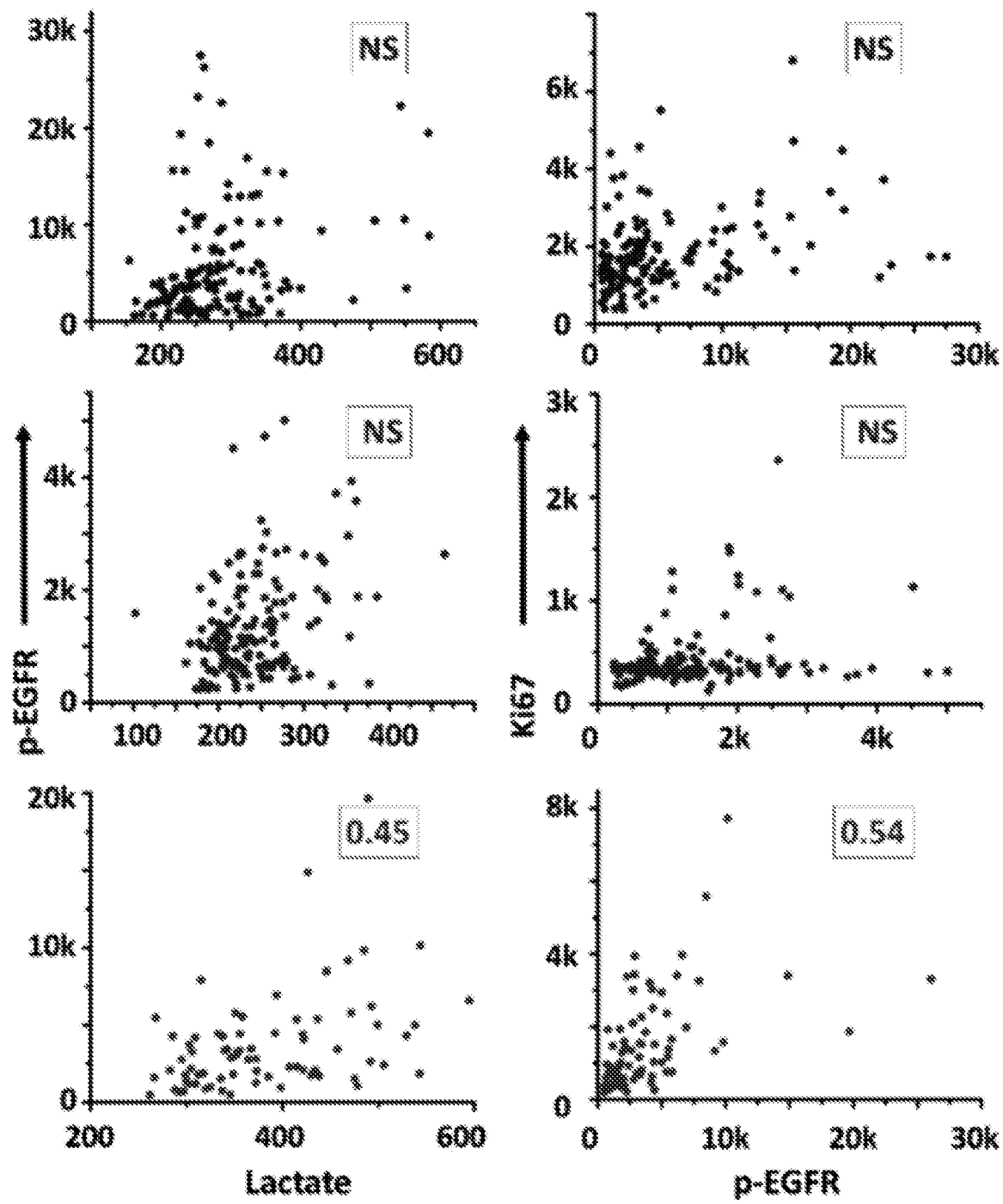
*Fig. 25, cont'd.*

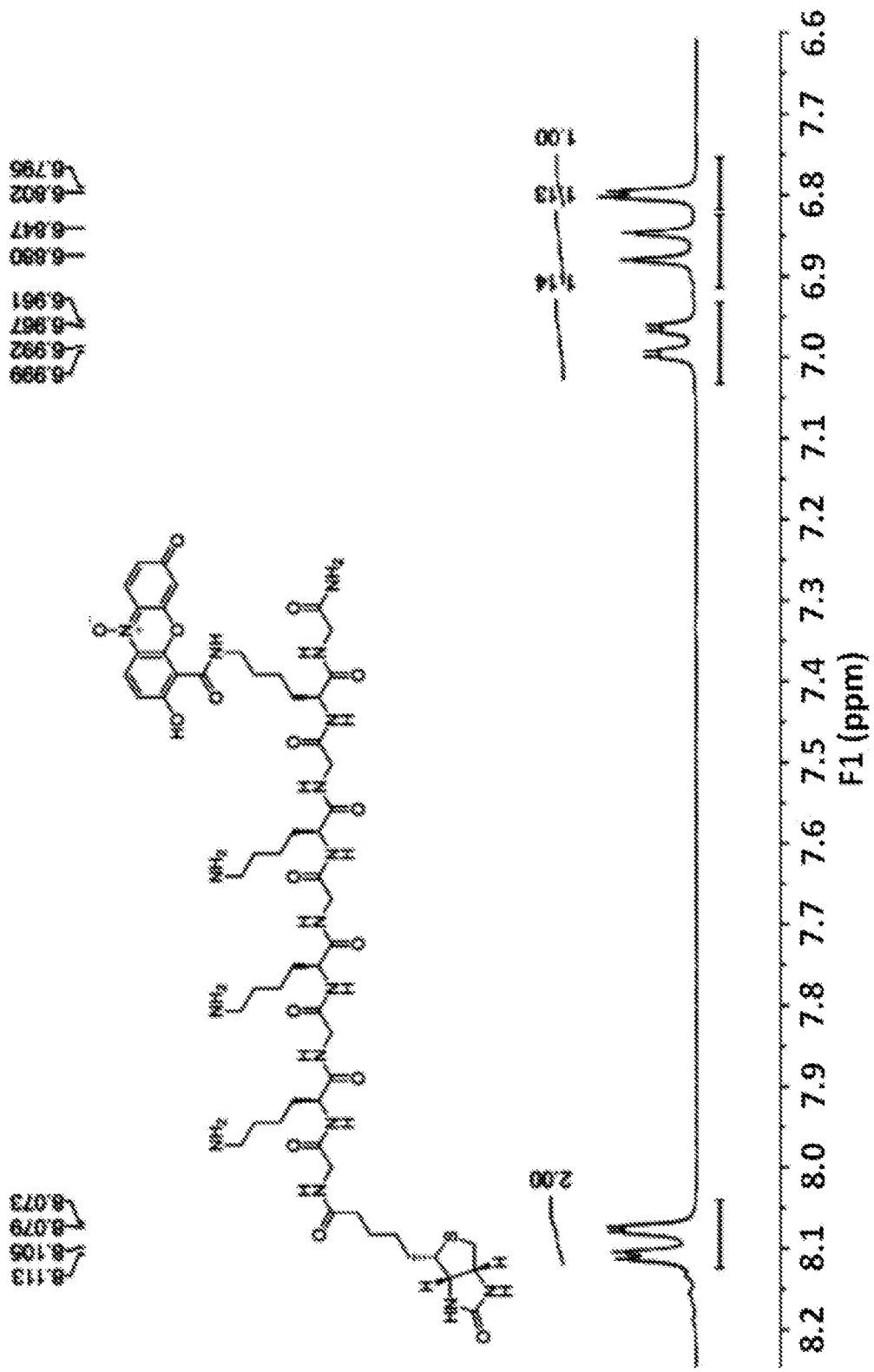
Fig. 30, cont'd.

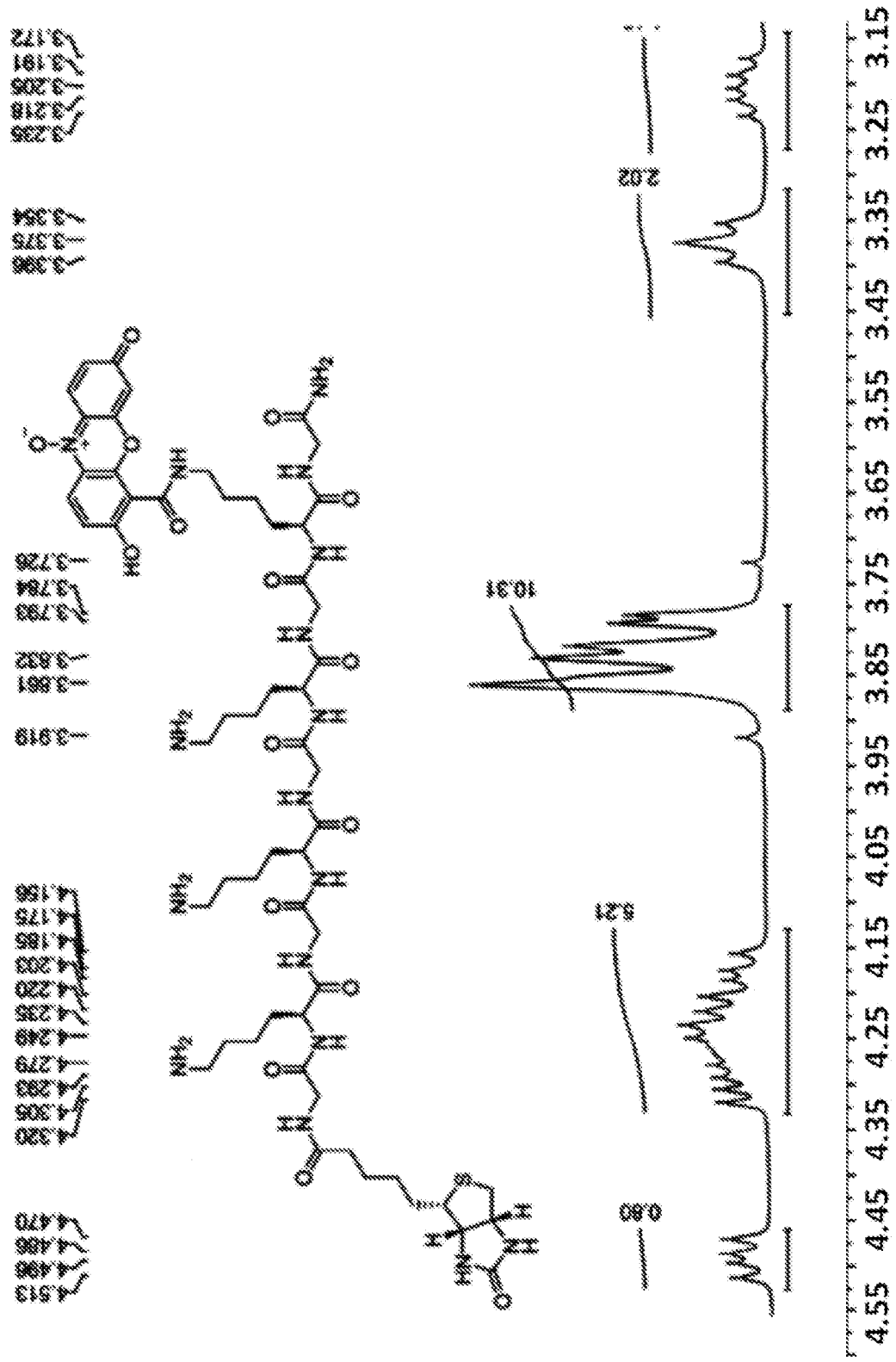
Fig. 30, cont'd.

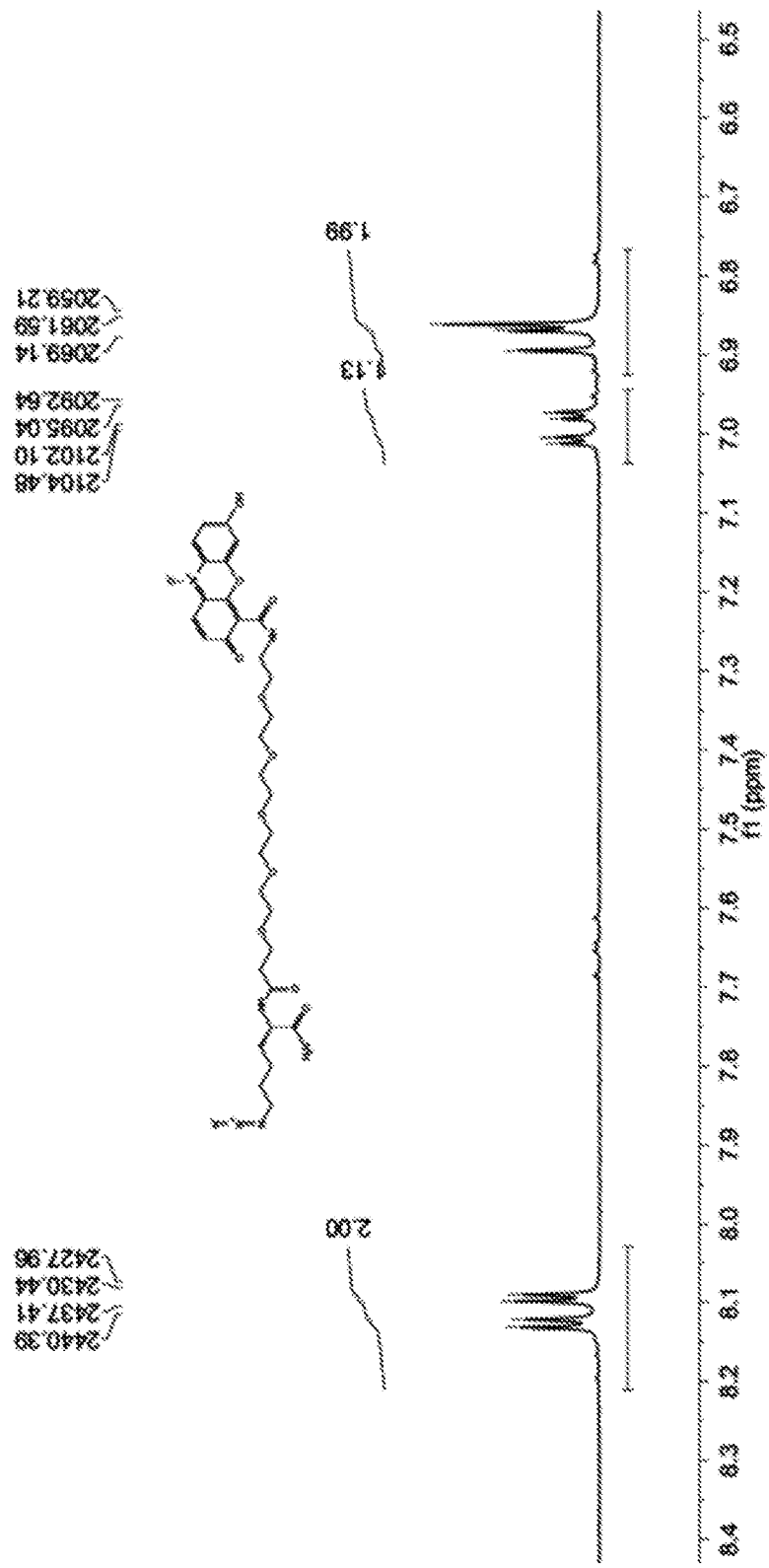
Fig. 31, con't.d

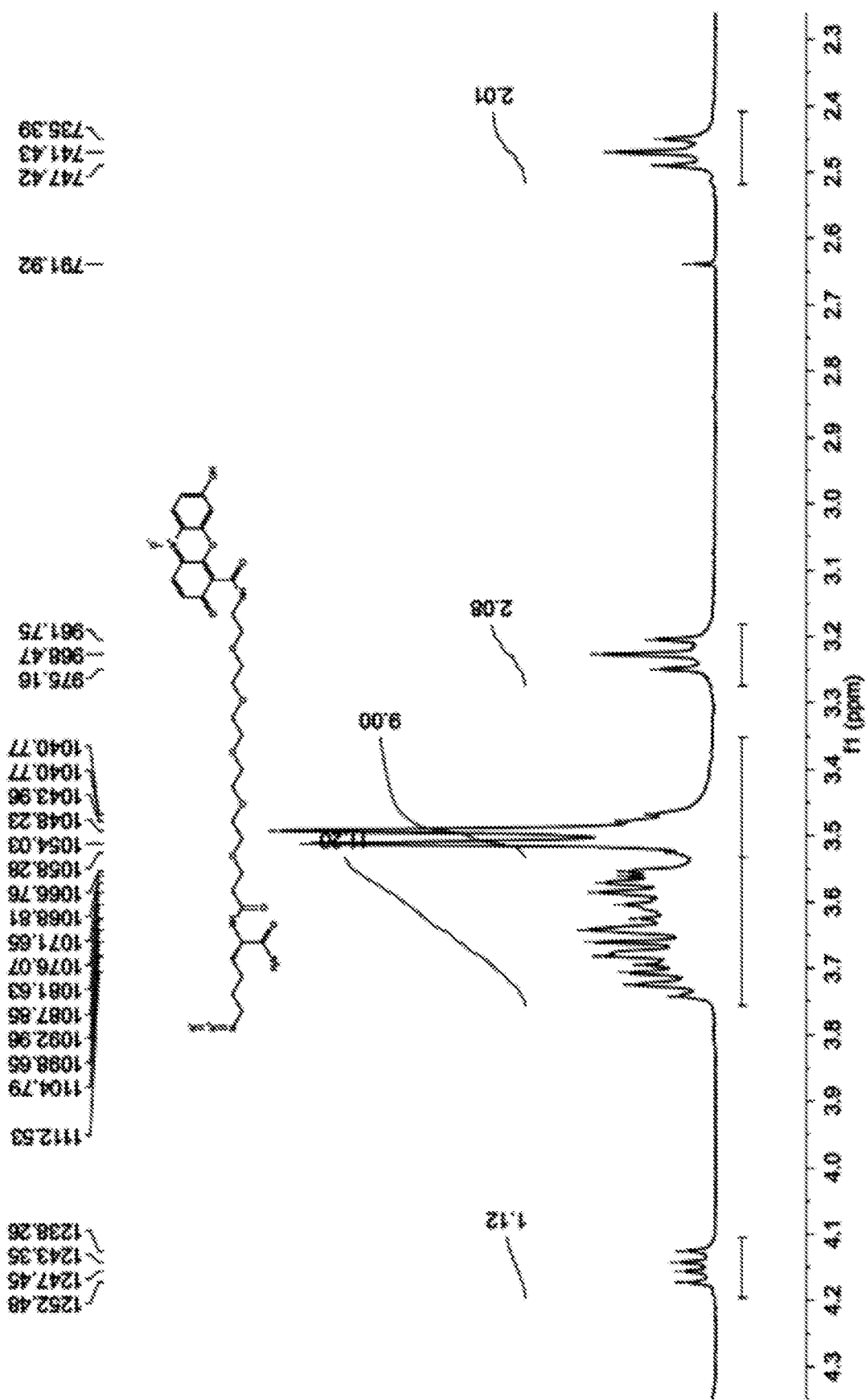
Fig. 31, con't.d

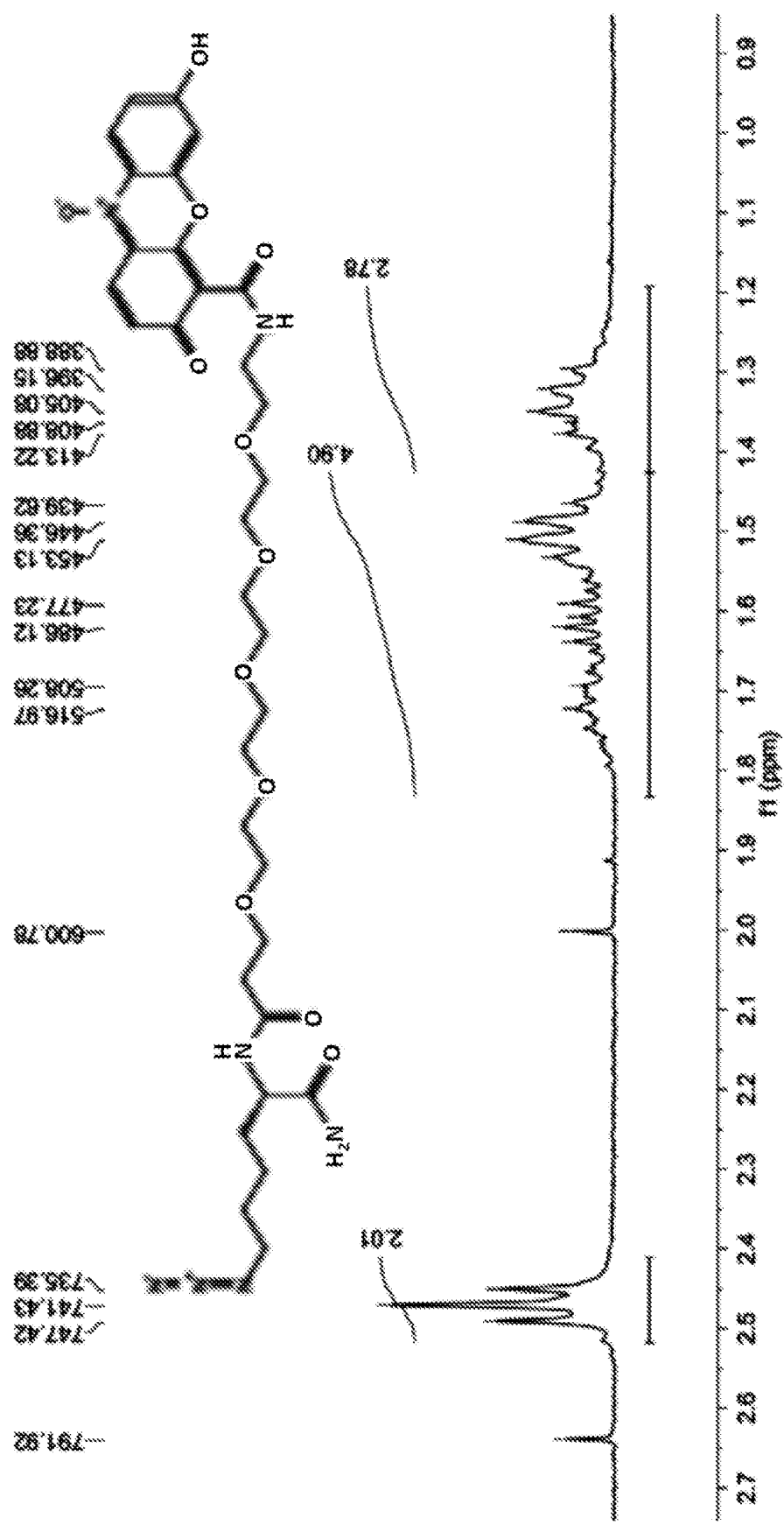
Fig. 31, con't.d

REDOX-LABILE FLUORESCENT PROBES AND THEIR SURFACE IMMOBILIZATION METHODS FOR THE DETECTION OF METABOLITES

CROSS-REFERENCE TO RELATED APPLICATIONS

This application is a 371 National Phase of PCT/US2019/040872, filed Jul. 8, 2019, which claims priority to and the benefit of U.S. Ser. No. 62/695,699, filed on Jul. 9, 2018, each of which are incorporated herein by reference in their entirety for all purposes.

STATEMENT OF GOVERNMENTAL SUPPORT

This invention was made with government support under Grant Numbers CA199090 and CA217655, awarded by the National Institutes of Health. The Government has certain rights in the invention.

INCORPORATION BY REFERENCE OF SEQUENCE LISTING PROVIDED AS A TEXT FILE

This application contains references to nucleic acid sequences that have been submitted concurrently herewith as the sequence listing text file "UCLA-P205US_ST25.txt", file size 1,347 bytes, created on Jul. 31, 2021, which is incorporated by reference in its entirety pursuant to 37 C.F.R. § 1.52 (e) (5).

BACKGROUND

The upregulation of aerobic glycolysis, known as the Warburg effect, is a hallmark of many cancers (Ito & Suda (2014) *Nat. Rev. Mol. Cell Biol.* 15:243-256; Kohli & Passegué (2014) *Trend. Cell Biol.* 24:479-487; Cairns et al. (2011) *Nat. Rev. Cancer,* 11:85-95). A common paradigm is that the driver oncogenic signaling confers and maintains the elevated glycolytic activities (Hanahan & Weinberg (2011) *Cell,* 144:646-674); however, recent studies have revealed that metabolic processes, such as aerobic glycolysis, are also capable of actively modulating cell-signaling networks (Locasale & Cantley (2011) (*Cell Metab.* 14:443-451). Those results highlight the complex interactions that exist between aerobic glycolysis and oncogenic signaling. Efforts in deciphering such interactions can be confounded by the intra- and inter-tumoral heterogeneity—a common feature of all cancers. Such heterogeneity facilitates tumor cells to adapt to stress through adopting new signaling and metabolic paradigms (Amir et al. (2013) *Nat. Biotech.* 31:545-552; McGranahan & Swanton (2017) (*Cell,* 168:613-628).

Single cell assays hold the promise to unveil the heterogeneity as well as the interplay between metabolic and oncogenic signaling, informing the rational design of therapeutic strategies that target tumor vulnerabilities. To this end, we have recently developed integrated proteomic and metabolic single cell assays on the single cell barcode chip (SCBC) platform, where glucose influx and signaling protein activities were simultaneously quantified from individual cells with fluorescence readouts (Xue et al. (2015) *J. Am. Chem. Soc.,* 137:4066-4069). However, glucose influx provides only an incomplete view of aerobic glycolytic capabilities (Cairns et al. (2011) *Nat. Rev. Cancer,* 11:85-95; Lunt & Heiden (2011) *Annu. Rev. Cell Dev. Biol.* 27:441-464), because the metabolic fate of the consumed glucose is not resolved. This caveat is especially prominent under drug perturbations, where subpopulations of cells may alter their glucose utilization to tolerate the drug stress (Xue et al. (2015). *J. Am. Chem. Soc.,* 137:4066-4069; Xue et al. (2016) *J. Am. Chem. Soc.* 138:3085-3093). Thus, quantifications of both glucose influx and lactate production at the single-cell level is required for a comprehensive understanding of the aerobic glycolysis in heterogeneous tumors.

In addition, there is an ever-increasing interest in further deciphering how the interplays between the Warburg effect and the oncogenic signaling provide a metabolic advantage to cancer cells, thereby promoting tumor growth (Hitosugi (2013) *J. Chen, Oncogene,* 33:4279). With the aim of untangling the mechanistic links among those components in heterogeneous tumors, it is necessary to perform simultaneous measurements on a panel of oncogenic signaling phosphoproteins, glucose influx and lactate production at the single cell level. To date, such task is only possible through the SCBC technology. Therefore, an orthogonal chemical approach that translates lactate quantity to fluorescence readouts so as to be incorporated into the SCBC platform is a pressing need.

Currently, quantification of lactate at the single cell level remains challenging. A major obstacle is the secretion nature of lactate, which renders those well-established uptake-based detection schemes incompatible. Another challenge is the lack of lactate-specific antibodies, due to their extremely small size and endogenous existence. Therefore, it is impractical to develop immuno-based lactate detection methods.

SUMMARY

Described herein is an analytical method for profiling lactate production in single cells, via the use of coupled enzyme reactions on surface-grafted resazurin molecules. The immobilization of the redox-labile probes was achieved through chemical modifications on resazurin, followed by bio-orthogonal click reactions. The lactate detection scheme was demonstrated to be sensitive and specific. The method was incorporated into the single cell barcode chip platform for simultaneous quantification of aerobic glycolysis activities and oncogenic signaling phosphoproteins in cancer. We interrogated the interplay between glycolysis and oncogenic signaling activities on a glioblastoma cell line. Results revealed a drug-induced oncogenic signaling reliance accompanying shifted metabolic paradigms. A drug combination that exploits this induced reliance exhibited synergistic effects in growth inhibition.

Accordingly, various embodiments contemplated herein may include, but need not be limited to, one or more of the following:

Embodiment 1

A detection reagent comprising a redox-active resazurin attached to a solid support.

Embodiment 2

The detection reagent of embodiment 1, wherein the attached resazurin demonstrates prominent fluorescence spectral changes in detecting NADH.

Embodiment 3

The detection reagent according to any one of embodiments 1-2, wherein the resazurin comprises 4-carboxyresazurin (CRz) wherein the aromatic carboxyl group is converted to an aliphatic reactive group.

Embodiment 4

The detection reagent of embodiment 3, wherein said aliphatic reactive group comprises a reactive group selected from the group consisting of an azide, a biotin, an amine, and a carboxyl.

Embodiment 5

The detection reagent of embodiment 4, wherein said aliphatic reactive group comprises an azide or a biotin.

Embodiment 6

The detection reagent of embodiment 5, wherein said aliphatic reactive group comprises an azide functional group and said resazurin comprises an azide-modified resazurin (APRz).

Embodiment 7

The detection reagent of embodiment 6, wherein said resazurin comprises the structure:

APRz wherein n is 2 to 24.

Embodiment 8

The detection reagent of embodiment 7, wherein n is 4.

Embodiment 9

The detection reagent according to any one of embodiments 6-8, wherein said resazurin is attached via said azide functional group to a diarylcyclooctyne moiety that is attached to said solid support.

Embodiment 10

The detection reagent of embodiment said 9, wherein said diarylcyclooctyne moiety comprises dibenzylcyclooctyne (DBCO).

Embodiment 11

The detection reagent according to any one of embodiments 9-10, wherein said diarylcyclooctyne moiety is attached to a solid support by a linker.

Embodiment 12

The detection reagent of embodiment 11, wherein said linker comprises a nucleic acid.

Embodiment 13

The detection reagent of embodiment 12, wherein said linker comprises a first nucleic acid attached to said diarylcyclooctyne moiety and said first nucleic acid is hybridized to a second nucleic acid attached to said solid support.

Embodiment 14

The detection reagent of embodiment 5, wherein said aliphatic reactive group comprises a biotin and said resazurin comprises an biotin-modified resazurin (BRz).

Embodiment 15

The detection reagent of embodiment 14, wherein said aliphatic reactive group comprises a peptide linker attaching said biotin to said resazurin.

Embodiment 16

The detection reagent of embodiment 15, wherein said peptide linker ranges in length from 1 amino acid, or from 2 amino acids up to about 20 amino acids, or up to about 15 amino acids, or up to about 10 amino acids, or up to about 8 amino acids, or up to about 6 amino acids.

Embodiment 17

The detection reagent of embodiment 16, wherein said peptide linker comprise the amino acid sequence GKGKGK (SEQ ID NO: 1).

Embodiment 18

The detection reagent of embodiment 17, wherein said biotin-modified resazurin comprise the structure:

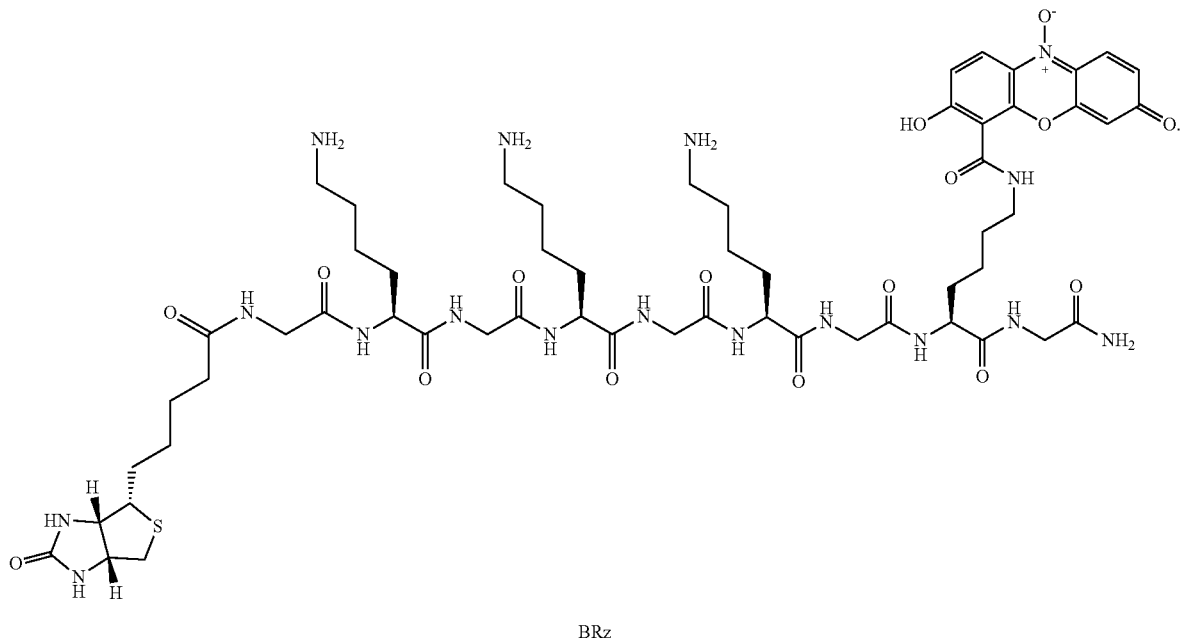
BRz
Embodiment 19
The detection reagent of embodiment 14, wherein said aliphatic reactive group comprises a polyethylene glycol (PEG) linker attaching said biotin to said resazurin.
Embodiment 20
The detection reagent of embodiment 19, wherein said biotin-modified resazurin comprises the structure:
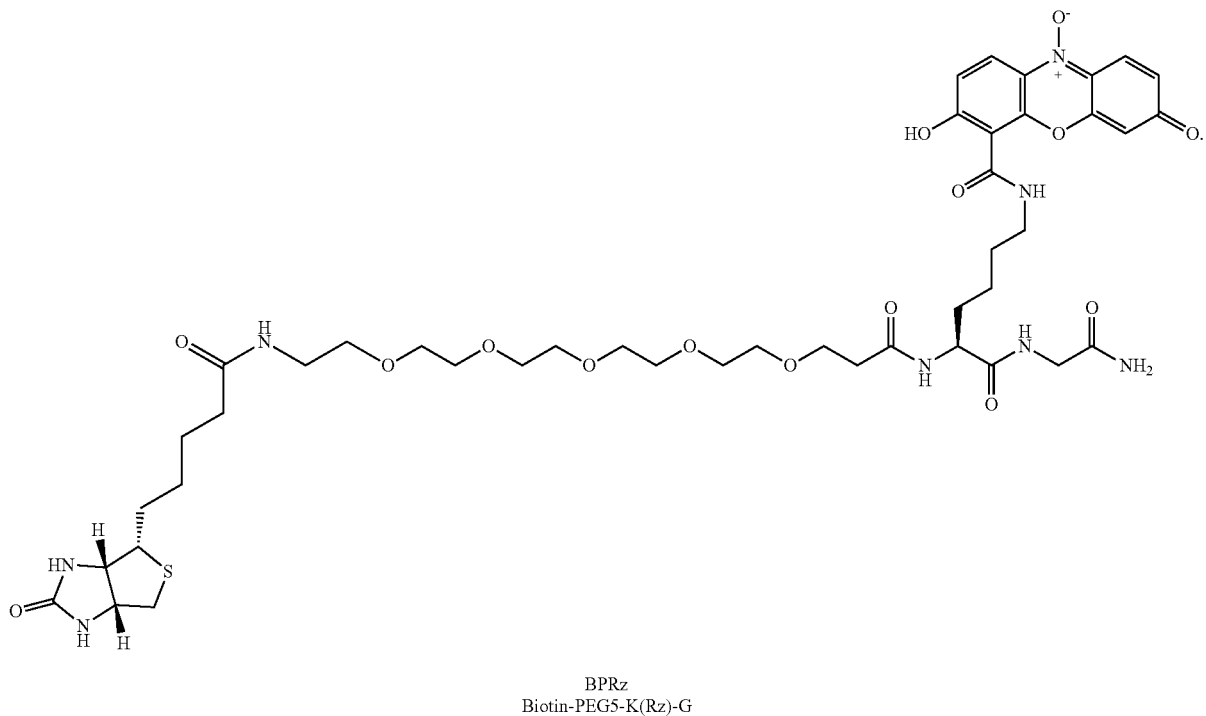
BPRz
Biotin-PEG5-K(Rz)-G

Embodiment 21

The detection reagent of embodiment 19, wherein said biotin-modified resazurin comprises the structure:

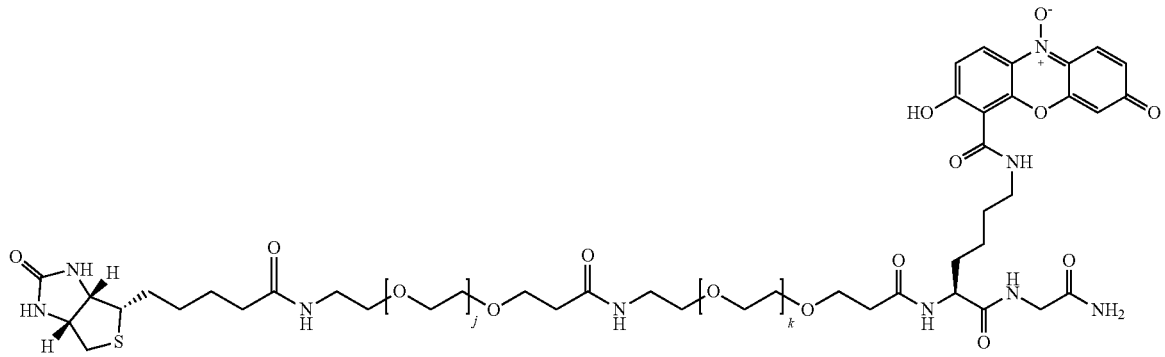

wherein j and k are independently 2-46.

Embodiment 22

The detection reagent of embodiment 21, wherein said biotin-modified resazurin comprises the structure:

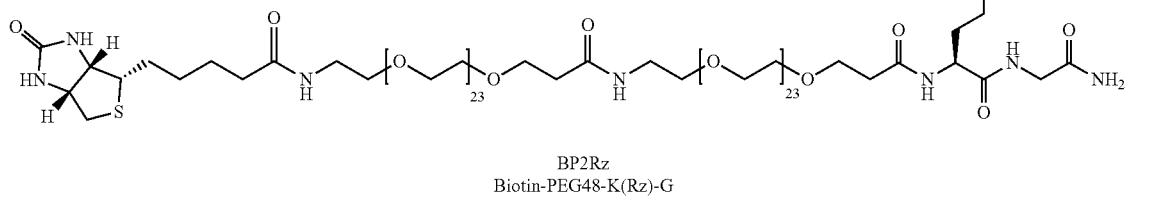

BP2Rz
Biotin-PEG48-K(Rz)-G

Embodiment 23

The detection reagent according to any one of embodiments 14-22, wherein said resazurin is attached via said biotin to a streptavidin that is attached to said solid support.

Embodiment 24

The detection reagent of embodiment 23, wherein said streptavidin is attached to a solid support by a linker.

Embodiment 25

The detection reagent of embodiment 24, wherein said streptavidin is attached to a solid support by a linker comprising a nucleic acid.

Embodiment 26

The detection reagent of embodiment 25, wherein said linker comprising a nucleic acid is hybridized to a second nucleic acid attached to said solid support.

Embodiment 27

The detection reagent according to any one of embodiments 6-26, wherein the reduced APRz exhibits higher fluorescence intensity than unmodified resorufin.

Embodiment 28

The detection reagent according to any one of embodiments 1-27, wherein said solid support comprise a surface of a microfluidic device.

Embodiment 29

The detection reagent according to any one of embodiments 1-28, wherein said solid support comprises a surface of a microchannel or a microwell.

Embodiment 30

The detection reagent according to any one of embodiments 1-29, wherein said solid support comprises a surface of an elastomeric microfluidics device.

Embodiment 31

The detection reagent of embodiment 30, wherein said solid support comprises a microchamber in a single cell barcode device.

Embodiment 32

The detection reagent of embodiment 31, wherein said single cell barcode device comprises a plurality of microchambers.

Embodiment 33

The detection reagent of embodiment 32, wherein said microchambers have a volume sufficient to contain one or a few mammalian cells.

Embodiment 34

The detection reagent of embodiment 33, wherein said microchambers each have a volume of about 2 nL or less, or about 1.5 nL.

Embodiment 35

The detection reagent according to any one of embodiments 30-34, wherein said device comprises one or a plurality of lysis buffer reservoirs.

Embodiment 36

The detection reagent of embodiment 35, wherein each microchamber has a companion lysis buffer reservoir separated from the microchamber/microwell by a valve.

Embodiment 37

The detection reagent according to any one of embodiments 30-36, wherein each microchamber comprises a set of DNA barcode stripes.

Embodiment 38

The detection reagent of embodiment 37, wherein said barcode stripes comprise a scaffold for multiplex measurements.

Embodiment 39

The detection reagent according to any one of embodiments 37-38, wherein said barcode(s) each represent a spatial address upon which a sandwich immunofluorescence assay for a specific protein is executed.

Embodiment 40

The detection reagent of embodiment 39, wherein said device provides for immunofluorescence assays for one or more signaling proteins.

Embodiment 41

The detection reagent of embodiment 40, wherein said signaling proteins comprise one or more proteins selected from the group consisting of phosph-P70 kinase, EGFR, p53, phosphor-TOR, phosphor-ERK1, NDRG1, Phospho-Src, phosphoAkt1, Ki67/MKI67.

Embodiment 42

The detection reagent according to any one of embodiments 30-41, wherein said microfluidic device said comprises a 2-layer microfluidic device.

Embodiment 43

The detection reagent according to any one of embodiments 30-42, wherein said microfluidic device said comprises greater than 100, or greater than 200, or greater than 300, or greater than 350 microchambers.

Embodiment 44

The detection reagent according to any one of embodiments 30-43, wherein said microfluidic device is configured to quantify lactate production.

Embodiment 45

The detection reagent of embodiment 44, wherein said device, in operation, is loaded with lactate dehydrogenase, diaphorase, and nicotinamide adenine dinucleotide (NAD+).

Embodiment 46

The detection reagent according to any one of embodiments 30-45, wherein said microfluidic device is configured to quantify glucose intake.

Embodiment 47

A single cell barcode chip (SCBC) comprising:
a plurality of microchambers of a size sufficient to contain one or a few mammalian cells;
a detection reagent according to any one of embodiments 1-27, attached to a surface comprising each of said microchambers.

Embodiment 48

The barcode chip of embodiment 47, wherein said microchambers microwells each have a volume of about 2 nL or less, or about 1.5 nL.

Embodiment 49

The barcode chip according to any one of embodiments 47-48, wherein said barcode chip comprises one or a plurality of lysis buffer reservoirs.

Embodiment 50

The barcode chip of embodiment 49, wherein each microchamber has a companion lysis buffer reservoir separated from the microchamber/microwell by a valve.

Embodiment 51

The barcode chip according to any one of embodiments 47-50, wherein each microchamber/microwell comprises a set of DNA barcode stripes.

Embodiment 52

The barcode chip of embodiment 51, wherein said barcode stripes comprise a scaffold for multiplex measurements.

Embodiment 53

The barcode chip according to any one of embodiments 51-52, wherein said barcode(s) each represent a spatial address upon which a sandwich immunofluorescence assay for a specific protein is executed.

Embodiment 54

The barcode chip of embodiment 53, wherein said device provides for immunofluorescence assays for one or more signaling proteins.

Embodiment 55

The barcode chip of embodiment 54, wherein said signaling proteins comprise phosph-P70 kinase.

Embodiment 56

The barcode chip according to any one of embodiments 54-55, wherein said signaling proteins comprise EGFR.

Embodiment 57

The barcode chip according to any one of embodiments 54-56, wherein said signaling proteins comprise p53.

Embodiment 58

The barcode chip according to any one of embodiments 54-57, wherein said signaling proteins comprise phosphor-TOR.

Embodiment 59

The barcode chip according to any one of embodiments 54-58, wherein said signaling proteins comprise phosphor-ERK1.

Embodiment 60

The barcode chip according to any one of embodiments 54-59, wherein said signaling proteins comprise NDRG1.

Embodiment 61

The barcode chip according to any one of embodiments 54-60, wherein said signaling proteins comprise Phospho-Src.

Embodiment 62

The barcode chip according to any one of embodiments 54-61, wherein said signaling proteins comprise phospho-Akt1.

Embodiment 63

The barcode chip according to any one of embodiments 54-62, wherein said signaling proteins comprise Ki67/MKI67.

Embodiment 64

The barcode chip according to any one of embodiments 47-63, wherein said microfluidic device said comprises a 2-layer microfluidic device.

Embodiment 65

The barcode chip according to any one of embodiments 47-64, wherein said microfluidic device said comprises a The greater than 100, or greater than 200, or greater than 300, or greater than 350 microchambers.

Embodiment 66

The barcode chip according to any one of embodiments 47-65, wherein said microfluidic device is configured to quantify lactate production.

Embodiment 67

The barcode chip of embodiment 66, wherein said device, in operation, is loaded with lactate dehydrogenase, diaphorase, and nicotinamide adenine dinucleotide (NAD+).

Embodiment 68

The barcode chip according to any one of embodiments 47-67, wherein said microfluidic device is configured to quantify glucose intake.

Embodiment 69

A method of determining lactate production of a cell, said method comprising:
  providing a cell lysate; and
  contacting the cell lysate with a detection reagent according to any one of embodiments 1-27 and enzymes and/or substrates that catalyze and couple the oxidation of lactate to the reduction of NAD or NADP;
  where said reduction of NAD or NADP converts said resazurin to resorufin providing a fluorescent signal that is a measure of the amount of lactate produced by said cell.

Embodiment 70

The method of embodiment 69, wherein said reagents and/or substrates that catalyze and couple the oxidation of lactate to the reduction of NAD or NADP comprises lactate dehydrogenase, nicotine adenine dinucleotide (NAD), and diaphorase.

Embodiment 71

The method according to any one of embodiments 69-70, wherein said solid support comprises a surface of a microfluidic device.

Embodiment 72

The method according to any one of embodiments 69-71, wherein said solid support comprises a surface of a microchannel or a microwell.

Embodiment 73

The method according to any one of embodiments 69-72, wherein said solid support comprises a surface of an elastomeric microfluidics device.

Embodiment 74

The method of embodiment 73, wherein said method is performed in a single cell barcode chip (SCBC) according to any one of embodiments 47-68.

Embodiment 75

The method of embodiment 74, wherein said method further comprises quantifying glucose intake by said cell.

Embodiment 76

The method according to any one of embodiments 74-75, wherein said method further comprises detecting and/or quantifying one or more signaling proteins.

Embodiment 77

The method of embodiment 76, wherein said signaling proteins comprise phosph-P70 kinase.

Embodiment 78

The method according to any one of embodiments 76-77, wherein said signaling proteins comprise EGFR.

Embodiment 79

The method according to any one of embodiments 76-78, wherein said signaling proteins comprise p53.

Embodiment 80

The method according to any one of embodiments 76-79, wherein said signaling proteins comprise phosphor-TOR.

Embodiment 81

The method according to any one of embodiments 76-80, wherein said signaling proteins comprise phosphor-ERK1.

Embodiment 82

The method according to any one of embodiments 76-81, wherein said signaling proteins comprise NDRG1.

Embodiment 83

The method according to any one of embodiments 76-82, wherein said signaling proteins comprise Phospho-Src.

Embodiment 84

The method according to any one of embodiments 76-83, wherein said signaling proteins comprise phosphoAkt1.

Embodiment 85

The method according to any one of embodiments 76-84, wherein said signaling proteins comprise Ki67/MKI67.

Embodiment 86

The method according to any one of embodiments 69-85, wherein said cell is a mammalian cell.

Embodiment 87

The method of embodiment 86, wherein said cell is a human cell.

Embodiment 88

The method of embodiment 86, wherein said cell is a non-human cell.

Embodiment 89

The method according to any one of embodiments 86-88, wherein said cell is a cancer cell.

Embodiment 90

A method of evaluating the effect of a one or more test agent(s) on a cell, said method comprising:
  contacting said cell with said test agent(s); and
  performing a method according to any one of embodiments 69-89 to determine at least the lactate production of said cell where the effect of said test agent(s) on said lactate production is determined.

Embodiment 91

The method of embodiment 90, wherein the effect of said test agent is with reference to a control cell in the absence of said test agent.

Embodiment 92

The method according to any one of embodiments 90-91, wherein said method further comprises quantifying glucose intake by said cell.

Embodiment 93

The method according to any one of embodiments 90-92, wherein said method further comprises detecting and/or quantifying one or more signaling proteins.

Embodiment 94

The method of embodiment 93, wherein said signaling proteins comprise phosph-P70 kinase.

Embodiment 95

The method according to any one of embodiments 93-94, wherein said signaling proteins comprise EGFR.

Embodiment 96

The method according to any one of embodiments 93-95, wherein said signaling proteins comprise p53.

Embodiment 97

The method according to any one of embodiments 93-96, wherein said signaling proteins comprise phosphor-TOR.

Embodiment 98

The method according to any one of embodiments 93-97, wherein said signaling proteins comprise phosphor-ERK1.

Embodiment 99

The method according to any one of embodiments 93-98, wherein said signaling proteins comprise NDRG1.

Embodiment 100

The method according to any one of embodiments 93-99, wherein said signaling proteins comprise Phospho-Src.

Embodiment 101

The method according to any one of embodiments 93-100, wherein said signaling proteins comprise phospho-Akt1.

Embodiment 102

The method according to any one of embodiments 93-101, wherein said signaling proteins comprise Ki67/MKI67.

Embodiment 103

The method according to any one of embodiments 90-102, wherein said cell is a mammalian cell.

Embodiment 104

The method of embodiment 103, wherein said cell is a human cell.

Embodiment 105

The method of embodiment 103, wherein said cell is a non-human cell.

Embodiment 106

The method according to any one of embodiments 103-105, wherein said cell is a cancer cell.

Embodiment 107

The method according to any one of embodiments 90-106, wherein said test agent is selected from the group consisting of a protein, an antibody, a small organic molecule, and a nucleic acid.

Embodiment 108

The method of embodiment 107, wherein said test agent comprises a pharmaceutical.

Embodiment 109

The method of embodiment 107, wherein said test agent comprises an anti-cancer compound

Embodiment 110

Test agent comprises one or more anti-cancer drugs.

Embodiment 111

The method according to any one of embodiments 90-110, wherein said method is performed in a single cell barcode chip (SCBC) according to any one of embodiments 47-68.

Embodiment 112

A method of detecting and/or quantifying a reducible or oxidizable analyte in a sample, said method comprising:
  contacting said sample with a reagent comprising a redox-active resazurin attached to a solid support according to any one of embodiments 1-27, wherein said sample further comprises enzyme(s) and/or substrates that enzymatically couple oxidation or reduction of said analyte with oxidation or reduction of said resazurin; and
  detecting a change in fluorescence of said resazurin, wherein said change in fluorescence comprises a measure of presence and/or quantity of said analyte.

Embodiment 113

The method of embodiment 112, wherein said analyte comprises an analyte selected from the group consisting of lactate, formate, glutamate, triacylglyceride, hydroxylglutarate, malate, fumarate, succinate, and citrate.

Embodiment 114

The method according to any one of embodiments 112-113, wherein said enzymes and/or substrates catalyze and couple the oxidation of said substrate to the reduction of NAD or NADP; and said reduction of NAD or NADP converts said resazurin to resorufin providing a fluorescent signal that is a measure of the amount of said analyte produced by said cell.

Embodiment 115

The method of embodiment 114, wherein said analyte comprises lactate.

Embodiment 116

The method of embodiment 115, wherein said reagents and/or substrates that catalyze and couple the oxidation of lactate to the reduction of NAD or NADP comprises lactate dehydrogenase, nicotine adenine dinucleotide (NAD), and diaphorase.

Embodiment 117

A modified resazurin functionalized for attachment to a substrate while preserving the oxidation-reduction indicator activity of said resazurin when attached to said substrate.

Embodiment 118

The modified resazurin of embodiment 117, wherein the resazurin comprises 4-carboxy-resazurin (CRz) wherein the aromatic carboxyl group is converted to an aliphatic reactive group.

Embodiment 119

The modified resazurin of embodiment 118, wherein said aliphatic reactive group comprises a reactive group selected from the group consisting of an azide, a biotin, an amine, and a carboxyl.

Embodiment 120

The modified resazurin of embodiment 119, wherein said aliphatic reactive group comprises an azide or a biotin.

Embodiment 121

The modified resazurin of embodiment 120, wherein said aliphatic reactive group comprises an azide functional group and said resazurin comprises an azide-modified resazurin (APRz).

Embodiment 122

The modified resazurin of embodiment 121, wherein said resazurin comprises the structure:

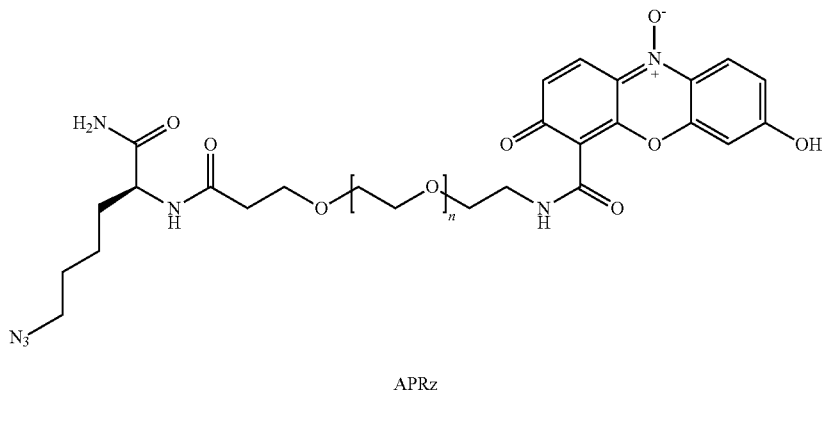

APRz wherein n is 2 to 24.

Embodiment 123

The modified resazurin of embodiment 122, wherein n is 4.

Embodiment 124

The modified resazurin according to any one of embodiments 121-123, wherein said resazurin is attached via said azide to a diarylcyclooctyne moiety that is attached to a linker.

Embodiment 125

The modified resazurin of embodiment said 124, wherein said diarylcyclooctyne moiety comprises dibenzylcyclooctyne (DBCO).

Embodiment 126

The modified resazurin according to any one of embodiments 124-125, wherein said linker is selected from the group consisting of a nucleic acid, a protein, an antibody, and an aliphatic linker.

Embodiment 127

The modified resazurin of embodiment 126, wherein said linker comprises a nucleic acid.

Embodiment 128

The modified resazurin of embodiment 120, wherein said aliphatic reactive group comprises a biotin and said resazurin comprises an biotin-modified resazurin (BRz).

Embodiment 129

The modified resazurin of embodiment 128, wherein said aliphatic reactive group comprises a peptide linker attaching said biotin to said resazurin.

Embodiment 130

The modified resazurin of embodiment 129, wherein said peptide linker ranges in length from 1 amino acid, or from 2 amino acids up to about 20 amino acids, or up to about 15 amino acids, or up to about 10 amino acids, or up to about 8 amino acids, or up to about 6 amino acids.

Embodiment 131

The modified resazurin of embodiment 130, wherein said peptide linker comprise the amino acid sequence GKGKGK (SEQ ID NO: 1).

Embodiment 132

The modified resazurin of embodiment 131, wherein said biotin-modified resazurin comprise the structure:

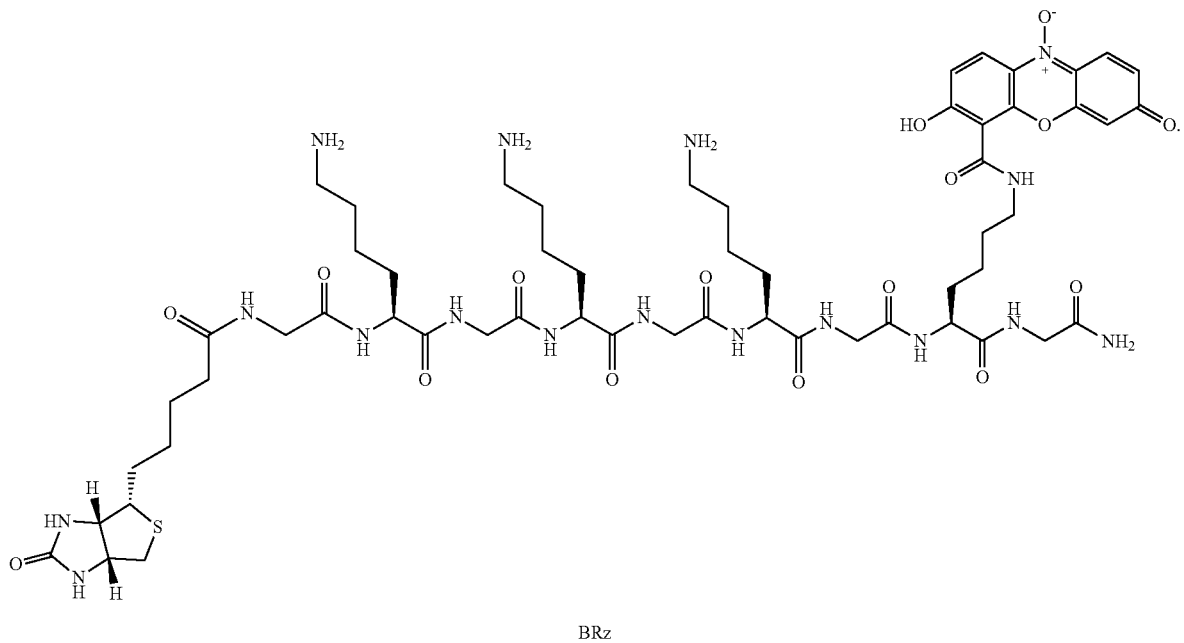
BRz
Embodiment 133
The modified resazurin of embodiment 128, wherein said aliphatic reactive group comprises a polyethylene glycol (PEG) linker attaching said biotin to said resazurin.
Embodiment 134
The modified resazurin of embodiment 133, wherein said biotin-modified resazurin comprises the structure:
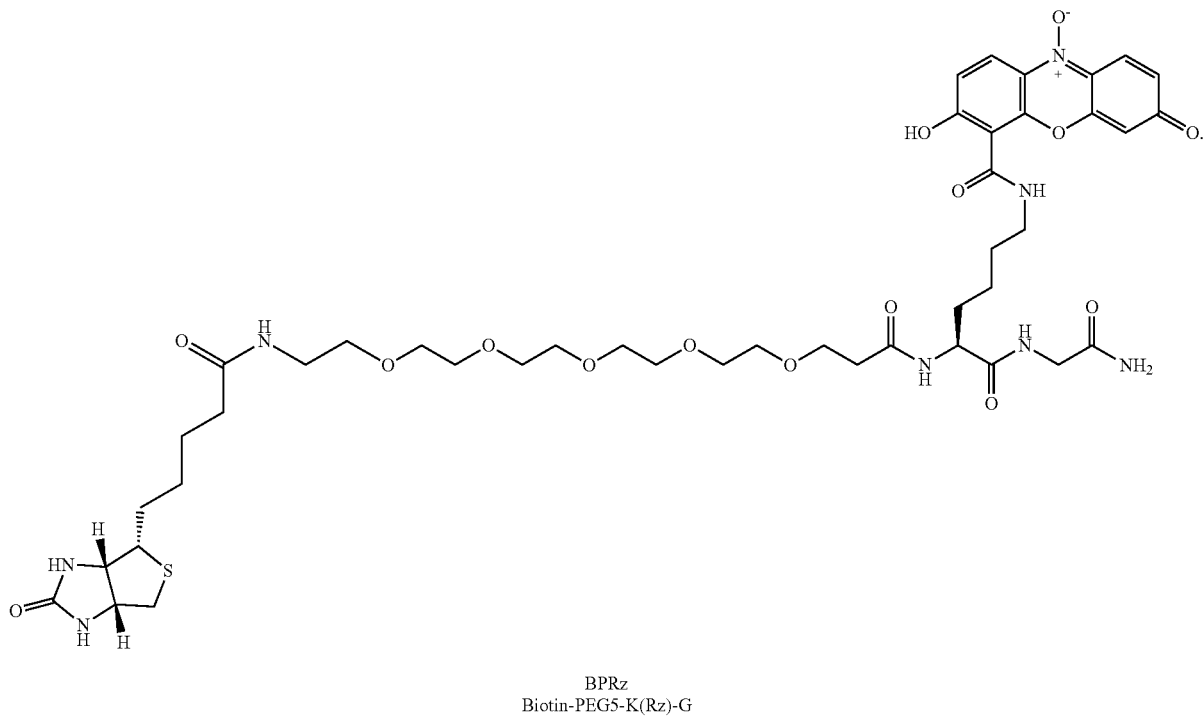
BPRz
Biotin-PEG5-K(Rz)-G

Embodiment 135

The modified resazurin of embodiment 133, wherein said biotin-modified resazurin comprises the structure:

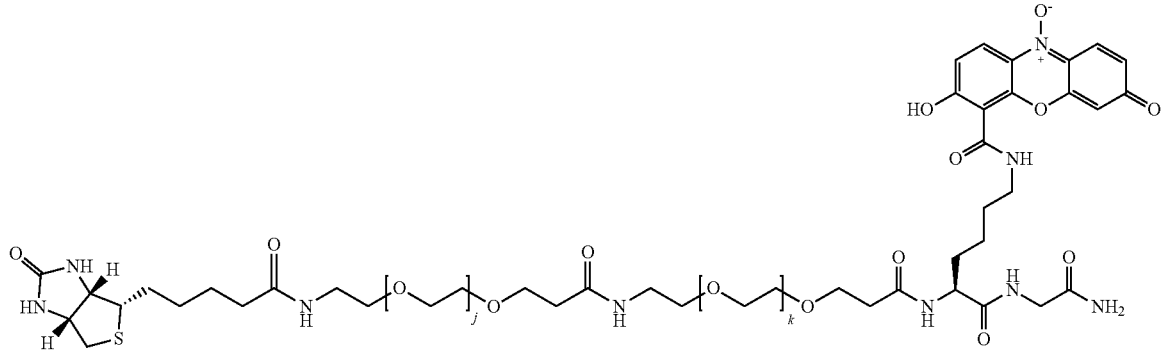

wherein j and k are independently 2-46.

Embodiment 136

The modified resazurin of embodiment 135, wherein said biotin-modified resazurin comprises the structure:

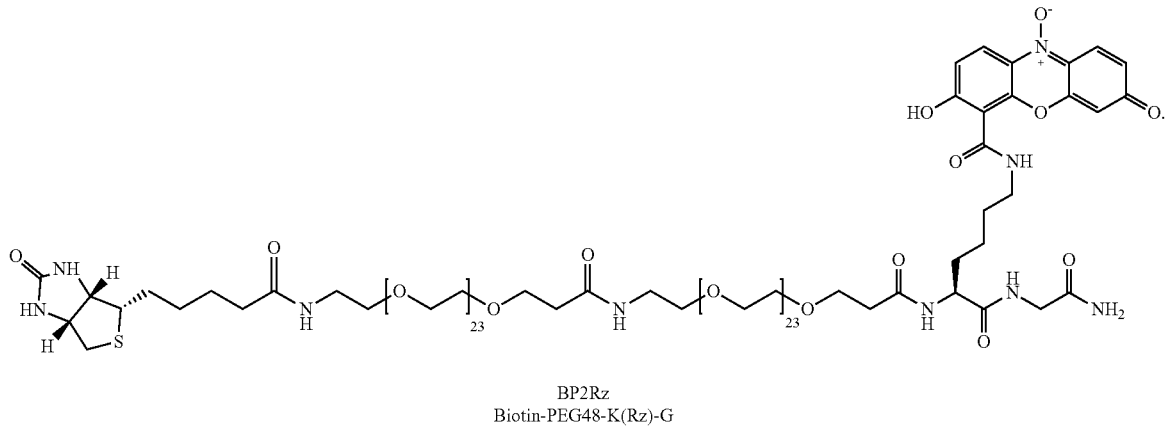

BP2Rz
Biotin-PEG48-K(Rz)-G

Embodiment 137

The modified resazurin according to any one of embodiments 128-136, wherein said resazurin is attached via said biotin to a streptavidin that is attached to said a solid support and/or to a linker.

Embodiment 138

The modified resazurin of embodiment 137, wherein said linker comprises a nucleic acid.

Definitions

The terms microchambers or microwells are used interchangeably to refer to chambers or wells in a microfluidics device. In certain embodiments the microchamber or microwells have a volume of about 50 nL or less, or about 40 nL or less, or about 30 nL or less, or about 20 nL or less, or about 10 nL or less, or about 5 nL or less, or about 3 nL or less, or about 2 nL or less.

As used herein, the terms "chip," "array chip," "chip platform," an "elastomeric microfluidics device" refer to a solid substrate or to a microfluidic device comprising a solid substrate upon which the resazurin/resorufinresorufin probe(s) described herein, and in certain embodiments, additional probes/assay components are immobilized. As disclosed herein, chip platforms may be made of any suitable materials. For example, chips may be made of polydimethylsiloxane (PDMS), glass, and/or thermoplastics including polymethyl methacrylate (PMMA), polycarbonate (PC), polystyrene (PS), cyclic olefin copolymer (COC), and/or cyclic olefin polymer (COP), and the like. In certain embodiments, some chip platforms may have more than one layer. For example, the single cell barcode chip (SCBC) is an example of a chip platform. In certain embodiments SCBC is a two-layer PDMS (or other soft-lithography material) chip and a DNA barcode glass slide.

As used herein the terms "immobilized, "immobilizing, and like terms refer to the conjugation or coupling of a molecule (e.g., a resazurin/resorufinresorufin probe, a DNA, a protein, an antibody, a small molecule) to a substrate, e.g., to a surface in a microfluidic chip.

As used herein, the term "DNA-immobilized and like terms refer to the coupling of a moiety (e.g., an antibody, a resazurin/resorufinresorufin probe described herein, etc.) onto a chip. In certain embodiments illustrative, but non-limiting embodiments, the immobilization is by nucleic acid (e.g., DNA) hybridization. In this approach, the chip is attached to a single stranded nucleic acid (e.g., ssDNA) that is complementary to a nucleic acid (e.g., ssDNA) conjugated to the moiety that is to be immobilized. Hybridization of the two nucleic acids results in immobilization of the moiety onto the chip.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49 (10): 1925) and references therein; Letsinger (1970) *J. Org. Chem.* 35:3800; Sprinzl et al. (1977) *Eur. J. Biochem.* 81:579; Letsinger et al. (1986) *Nucl. Acids Res.* 14:3487; Sawai et al. (1984) *Chem. Lett.* 805, Letsinger et al. (1988) *J. Am. Chem. Soc.* 110:4470; and Pauwels et al. (1986) *Chemica Scripta* 26:141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992). *J. Am. Chem. Soc.* 114:1895; Meier et al. (1992) *Chem. Int. Ed. Engl.* 31:1008; Nielsen (1993) *Nature*, 365:566; Carlsson et al. (1996) *Nature* 380:207). Other analog nucleic acids include those with positive backbones (Denpcy et al. (1995) *Proc. Natl. Acad. Sci. USA* 92:6097; non-ionic backbones (U.S. Pat. Nos. 5,386,023, 5,637,684, 5,602,240, 5,216,141 and 4,469,863; Angew. (1991) *Chem. Intl. Ed. English* 30:423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4:395; Jeffs et al. (1994) J. *Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. In addition, it is possible that nucleic acids of the present invention can alternatively be triple-stranded.

DETAILED DESCRIPTION

In various embodiments, a modified resazurin is provided that is functionalized for attachment to a substrate while preserving the oxidation-reduction indicator activity of the resazurin when attached to the substrate. As explained herein (see, e.g., Example 1) a 4-carboxyresazurin (CRz) was synthesized to enable further conjugation. Other modifications to resazurin, such as alkylation and acetylation on the phenolic hydroxyl group, render the resulting resorufin counterparts non-fluorescent.

Because direct conjugation of CRz to the surface led to negligible yield, to improve the CRz reactivity, the aromatic carboxylic group was converted to various to aliphatic reactive groups. In particular, an extended CRz structure bearing an azide functional group was shown to demonstrate prominent fluorescence spectral changes in detecting NADH even when attached to a surface (e.g., a solid substrate).

Figure 1:
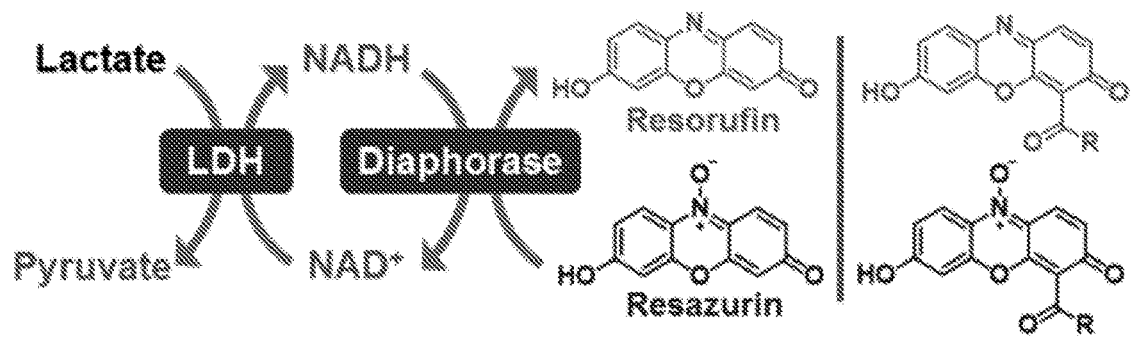
FIG. 1. Panel A) The principle of assaying lactate through coupled enzyme reactions on resazurin substrates. The amount of lactate translates to the fluorescence intensity of resorufin. Panel B) Surface immobilization of the resazurin analogs integrated with microfluidic-based technology enable the quantification of lactate production from single cells.
Figure 1:
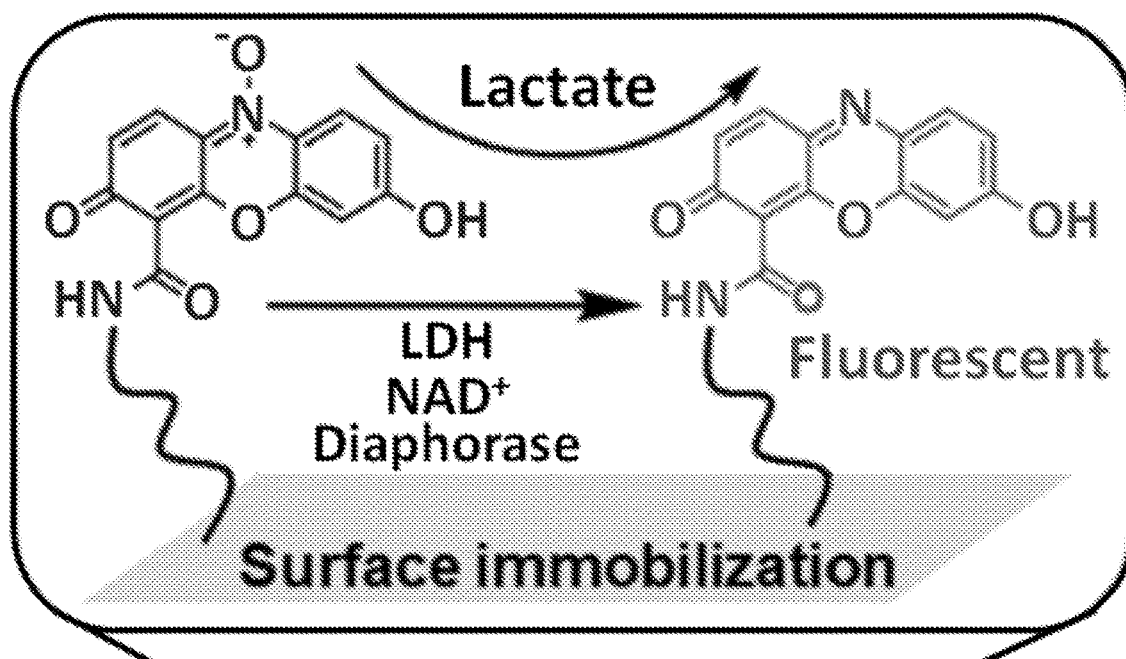
Figure 1:
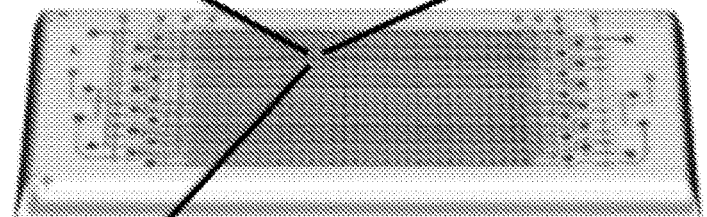
Figure 13:
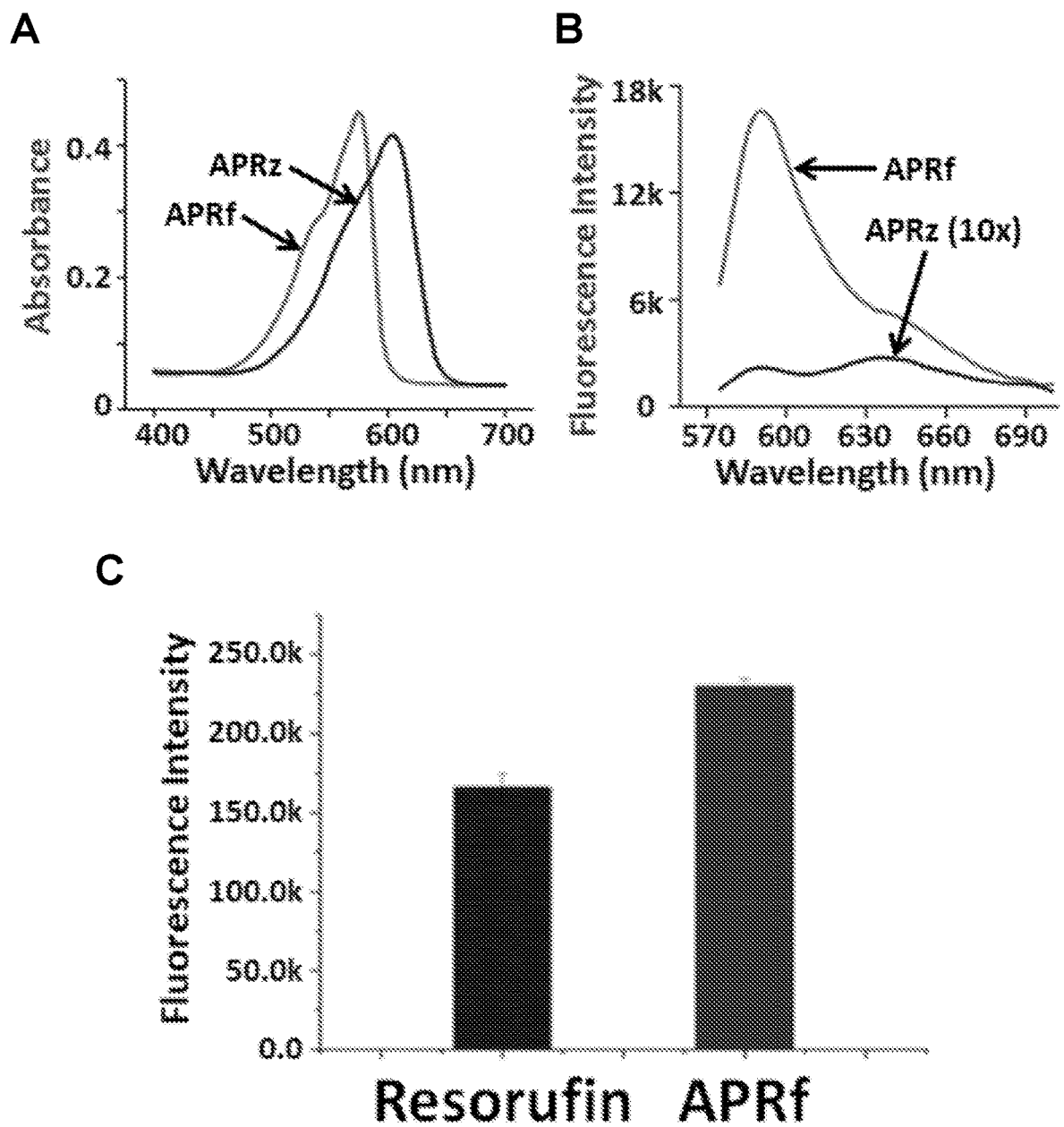
FIG. 13. Panel a) Absorption and panel (b) fluorescence spectra of APRz and the reduced form, APRf. Panel c) Comparison of fluorescence intensity of 4-carboxyresorufin and APRf, both at a concentration of 10 μM in pH 7.4 PBS. Excitation/Emission: 540 nm/590 nm.

The azide functionalized resazurin (APRz) probe when used in an enzyme coupled lactate assay (see, e.g., FIG. 1, panel a) exhibited almost ten-fold increase of fluorescence intensity after lactate conversion (FIG. 1, panel b). Moreover, the reduced APRz exhibited higher fluorescence intensity than unmodified resorufin (see, e.g., FIG. 13). In addition, the APRz showed faster reaction kinetics in a diaphorase catalyzed NADH oxidation reaction than unmodified resazurin, demonstrating its superior performance (see, e.g., FIG. 14).

Figure 3:
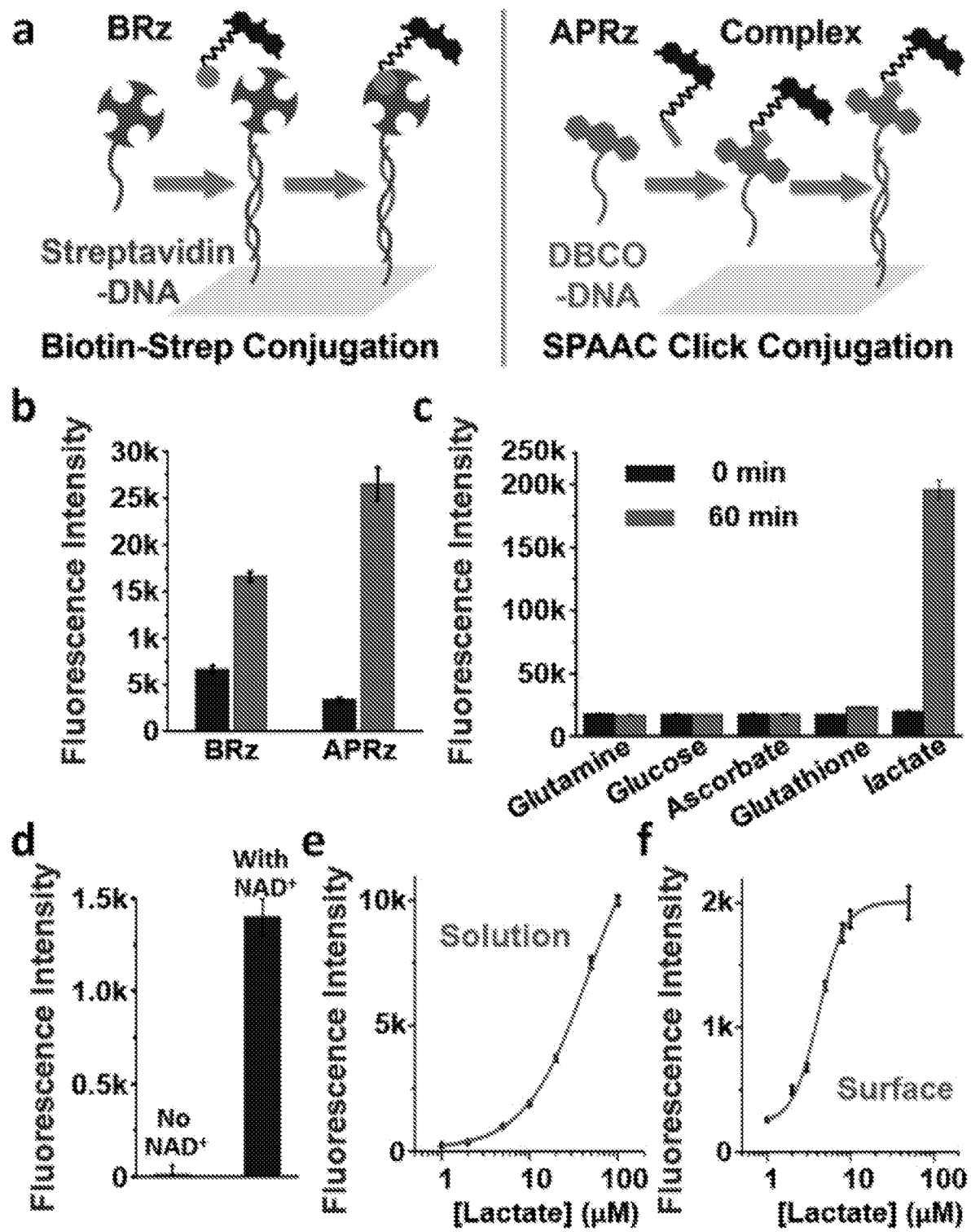
FIG. 3. Panel a) Biotin-modified CRz (BRz) and azide-modified CRz (APRz) enable surface immobilization. Panel b) Surface fluorescence intensities before and after the lactate assay. Larger increase of fluorescence indicates better efficiency in lactate detection. Panel c) Comparison of the fluorescence increase of APRz resulted from lactate conversion and other intracellular reducing agents. Panel d) Lactate assay results using GBM39 cell lysates. APRz was mixed with diaphorase and LDH. To this mixture was added cell lysate, or cell lysate/NAD+. Background fluorescence value obtained from a lysis buffer control was subtracted. Panels e, f) Working curve for the solution phase and surface-based lactate detection, using APRz as the substrate. The curves were obtained through fitting with Hill functions.
Figure 15:
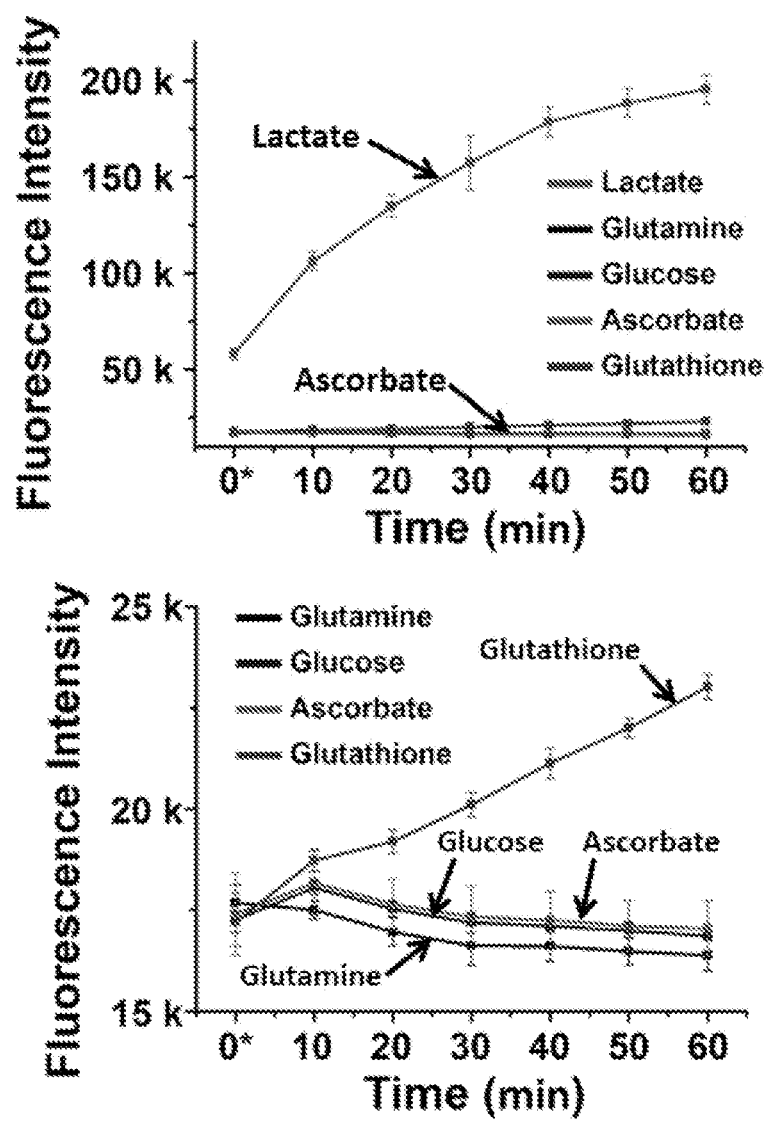
FIG. 15. Comparison of the reaction kinetics using different reducing agents. The concentrations used were: Lactate 16 μM; Glutamine 6 mM; Glucose 6 mM; Ascorbate 100 nM; Glutathione 6 mM, APRz 8 UM in PBS. *Some delay after reaction start was involved, due to the time required for mixing and starting the measurements.

The substrate-bound azide-functionalized resorufinresorufin (APRz) additionally showed very slow reaction kinetics and led to insignificant fluorescence increase within the duration of an assay in response to common intracellular reducing agents such as glutathione and ascorbic acid, as well as glucose and glutamine (see, e.g., FIG. 3, panel c, FIG. 15). Additionally, using cell lysates, without the addition of extra NAD+, the reduction of APRz was negligible (see, e.g., FIG. 3, panel d, and FIG. 16).

In view of these and other observations (see, e.g., Example 1), the azide-functionalized resorufin provides an effective indicator for detecting oxidation/reduction reactions and can readily utilized to detect and quantify an analyte whose oxidation or reduction can be enzymatically coupled to the oxidation or reduction of this indicator.

In addition to azide-functionalized resorufin, in certain embodiments resorufin functionalized with biotin, or amide, or carbonyl, are also contemplated.

The functionalized resorufin can readily be incorporated into a test device by attachment to a surface of that device. In certain embodiments the immobilization of the redox-labile modified resazurin probes can achieved through bio-orthogonal click reactions that readily facilitate attachment to essentially any desired surface. Where the resazurin probe is functionalized with a biotin, the probe can readily be coupled to a surface by reaction with an avidin or streptavidin. Thus, for example, in certain embodiments the resorufin is coupled to a surface of a microfluidic device. In certain embodiments the surface comprises a surface of a microchannel or a microwell. In certain embodiments the surface comprise a surface of an elastomeric microfluidics device.

By way of non-limiting illustration, as described herein the substrate-bound functionalized resorufin probe can readily be adapted single cell level of analyte quantitation. Thus, as shown in Example 1, a lactate assay using the functionalized resorufin probe was incorporated into a single-cell barcode chip (SCBC) that allowed quantitation on of a plurality of analytes in addition to lactate. In an illustrative, but non-limiting embodiment, glucose uptake, lactate pro-duction, and a panel of signaling proteins were quantified. The effect of test agents such as erlotinib (EGFR inhibitor), and oligomycin A (ATPase inhibitor) on these parameters was evaluated.

Accordingly, in various embodiments a modified resazurin/resorufin functionalized for attachment to a substrate while preserving the oxidation-reduction indicator activity of the resazurin/resorufin when attached to the substrate is provided. In certain embodiments a redox detection reagent comprising a redox-active resazurin attached to a solid support is provided. In various embodiments a microfluidic device is provided (e.g., a device comprising a plurality of microchambers and/or microchannels) where the modified resazurin/resorufin is attached to a surface (e.g., a surface of a chamber and/or channel) in the device. In certain embodiments the microfluidic device comprise a single cell barcode device (SCBC). In certain embodiments the SCBC device can be configured for the detection of lactate (or other redox analytes) using the attached resazurin/resorufin probe(s). In certain embodiments the SCBC device can additionally be configured to detect additional analytes including, but not limited to glucose (e.g., cellular glucose uptake), and/or various signaling proteins. In various embodiments methods of detecting and/or quantifying a reducible or oxidizable analyte (e.g., lactate, formate, glutamate, etc.) in a sample using the immobilized resazurin/resorufin probe(s) are provided. The methods can also be used to screen the effect of one or more test agents on cells.

Functionalized Resorufin Probe.

In various embodiments a resazurin/resorufin functionalized for attachment to a surface while retaining redox indicator activity is provided. In certain embodiments the resazurin comprises 4-carboxy-resazurin (CRz) where the aromatic carboxyl group is converted to an aliphatic reactive group (see, e.g., Example 1). In certain embodiments the reactive group comprises an azide, a biotin, an amine, or a carboxyl. In certain embodiments the reactive group comprises an azide or a biotin.

In certain embodiments the aliphatic reactive group comprises an azide functional group and the resazurin comprises an azide-modified resazurin (APRz). In certain embodiments the resazurin comprises the structure:

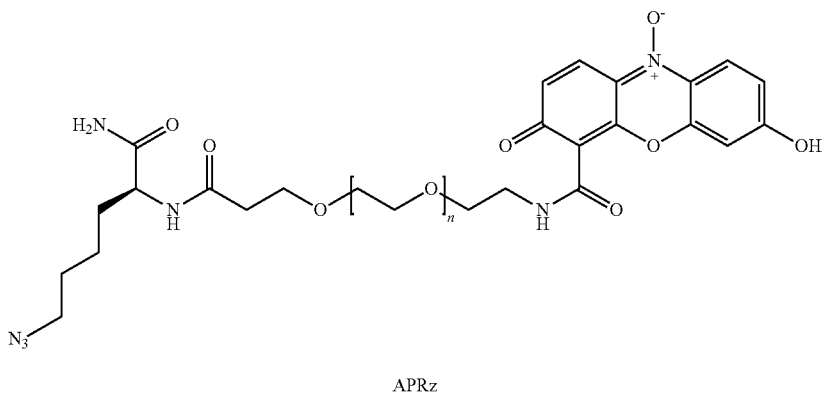

APRz wherein n is n is 2 to 24, or 2 to 18, or 2 to 12. In certain embodiments n is 4. In certain embodiments n is 2, or 3, or 5, or 6, or 7, or 8, or 9, or 10, or 11, or 12, or 13, or 14, or 15, or 16, or 17, or 18, or 19, or 20, or 21, or 22, or 23, or 24.

The azide moiety on the functionalized resazurin can readily be exploited to attach the resazurin to another moiety comprising a diarylcyclooctyne moiety using click chemistry. This click chemistry is based on the reaction of a diarylcyclooctyne moiety (DBCO, or ADIBO) with an azide-labeled reaction partner, known as strain-promoted alkyne azide cycloaddition (SPAAC). This click reaction, unlike conventional click chemistry, is very fast at room temperature and does not require a cytotoxic Cu(I) catalyst that is toxic to most organisms.

In certain embodiments the diarylcyclooctyne moiety is attached to a linker that can be coupled to a substrate. Illustrative linkers include, but are not limited to a nucleic acid, a protein, an antibody, an aliphatic linker, and the like. Where the linker comprises a single strand nucleic acid (e.g., ssDNA), the attached resazurin/resorufin probe can readily be attached to a substrate by hybridization to a complementary nucleic acid which, in turn, is attached to that substrate (see, e.g., Example 1).

In certain embodiments the aliphatic reactive group comprises a biotin and the resazurin comprises an biotin-modified resazurin (BRz). In various embodiments the liphatic reactive group comprises a peptide linker attaching said biotin to said resazurin. In certain embodiments the peptide linker ranges in length from 1 amino acid, or from 2 amino acids up to about 40 amino acids, or up to about 30 amino acids, or up to about 20 amino acids, or up to about 15 amino acids, or up to about 10 amino acids, or up to about 8 amino acids, or up to about 6 amino acids. In certain embodiments the peptide linker comprises 1, or 2, or 3, or 4, or 5, or 6, or 7, or 9, or 10, or 11, or 12, or 13, or 14, or 15, or 16, or 17, or 18, or 19, or 20, or 21, or 22, or 23, or 24, or 25, or 26, or 27, or 28, or 29, or 30 amino acids. In certain embodiments the peptide linker comprise the amino acid sequence GKGKGK (SEQ ID NO: 1), or the amino acid sequence GKGK (SEQ ID NO:2), or the amino acid sequence GKGKGKGK (SEQ ID NO:3), or the amino acid sequence GKGKGKGKGK (SEQ ID NO:4), or the amino acid sequence GKGKGKGKGKGK (SEQ ID NO: 5). In certain embodiments the biotin-modified resazurin comprises the structure:

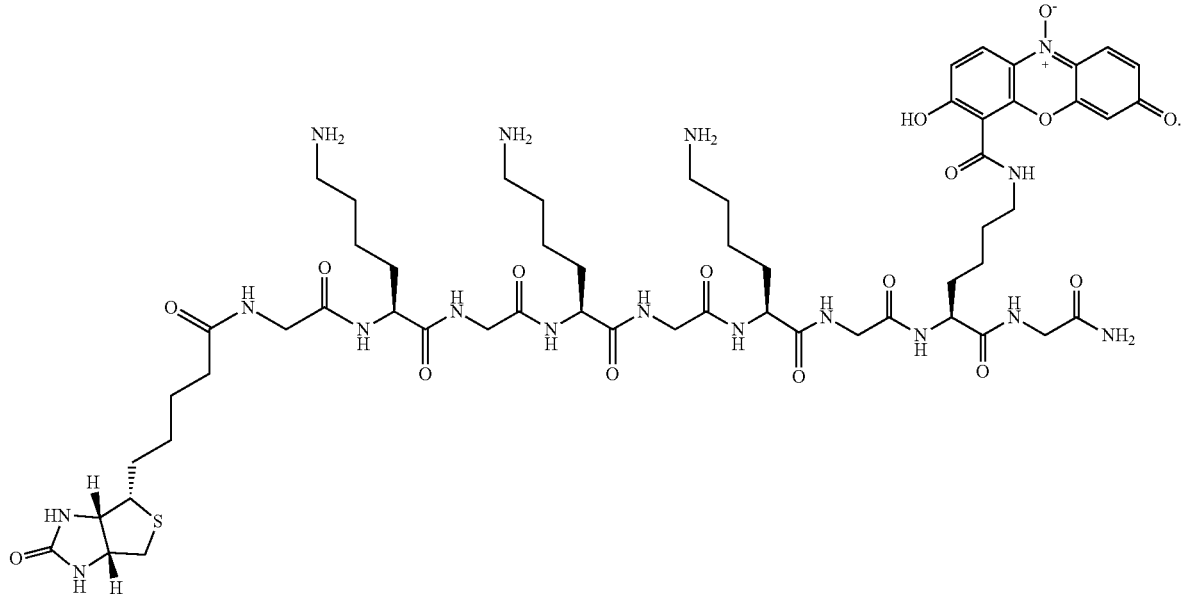

BRz

In certain embodiments the aliphatic reactive group comprises a polyethylene glycol (PEG) linker attaching the biotin to the resazurin. In certain embodiments the biotin-modified resazurin comprises the structure:

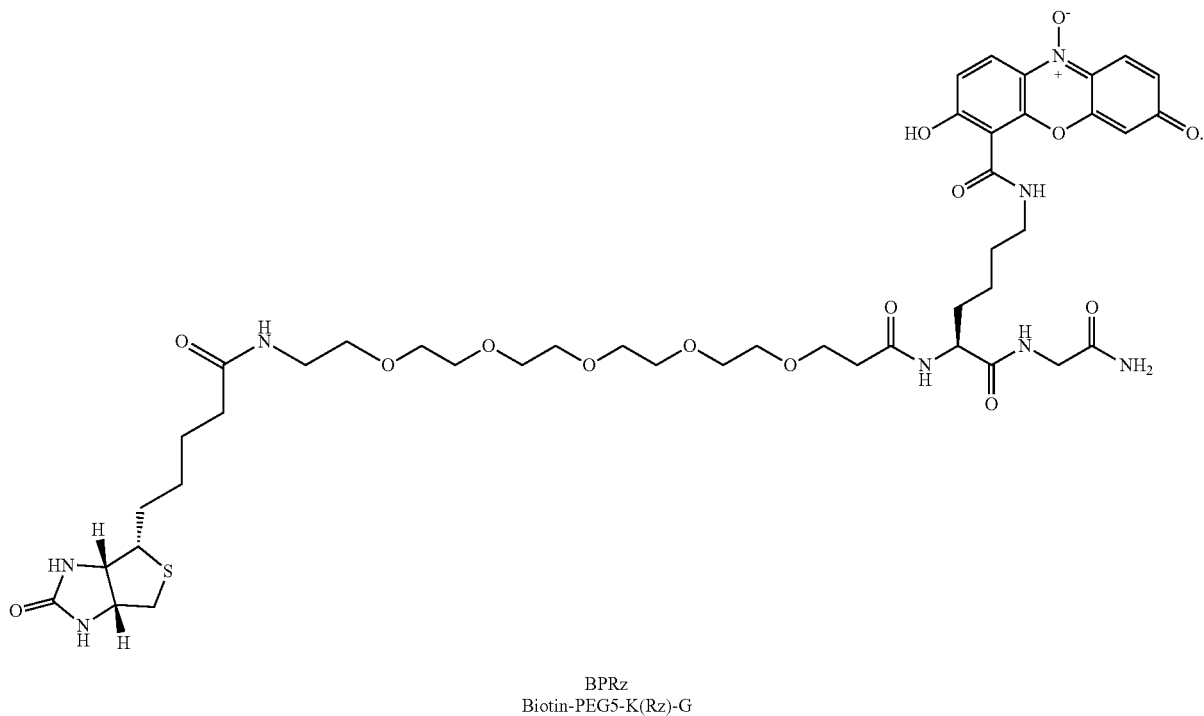

BPRz
Biotin-PEG5-K(Rz)-G

In certain embodiments the biotin-modified resazurin comprises the structure:

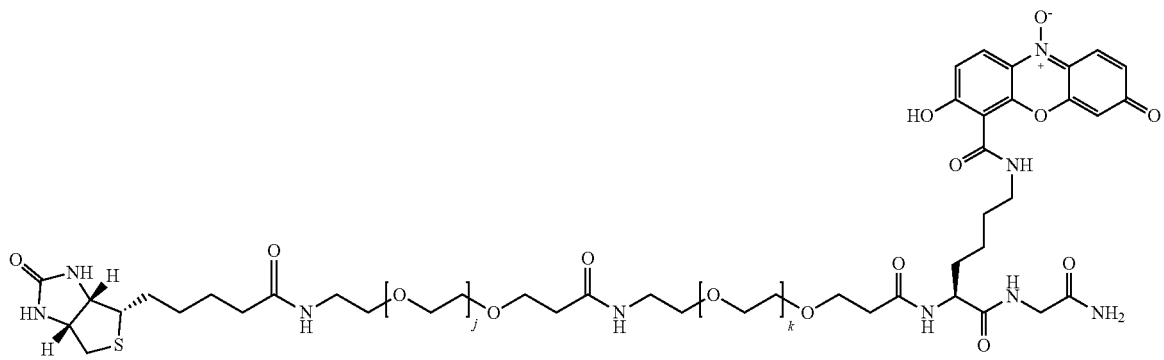

wherein j and k are independently 2-46. In certain embodiments j and/or k are independently 1, or 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30, or 31, or 32, or 33, or 34, or 35, or 36, or 37, or 38, or 39, or 40, or 4, or 42, or 43, or 44, or 45, or 46, or 47, or 48, or 49, or 50. In certain embodiments the biotin-modified resazurin comprises the structure:

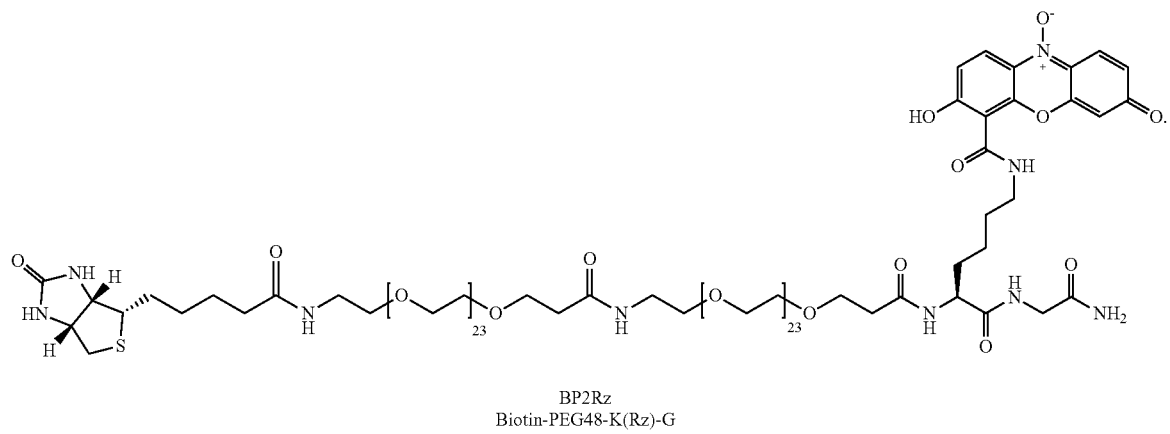

BP2Rz
Biotin-PEG48-K(Rz)-G

In certain embodiments the resazurin is attached via the biotin to an avidin or streptavidin that is can be or is attached to a solid support. In certain embodiments the avidin or streptavidin is attached to a solid support by a linker. In certain embodiments such a linker comprises a nucleic acid. In certain embodiments the linker comprises a nucleic acid is hybridized to a second nucleic acid attached to said solid support.

Figure 8:
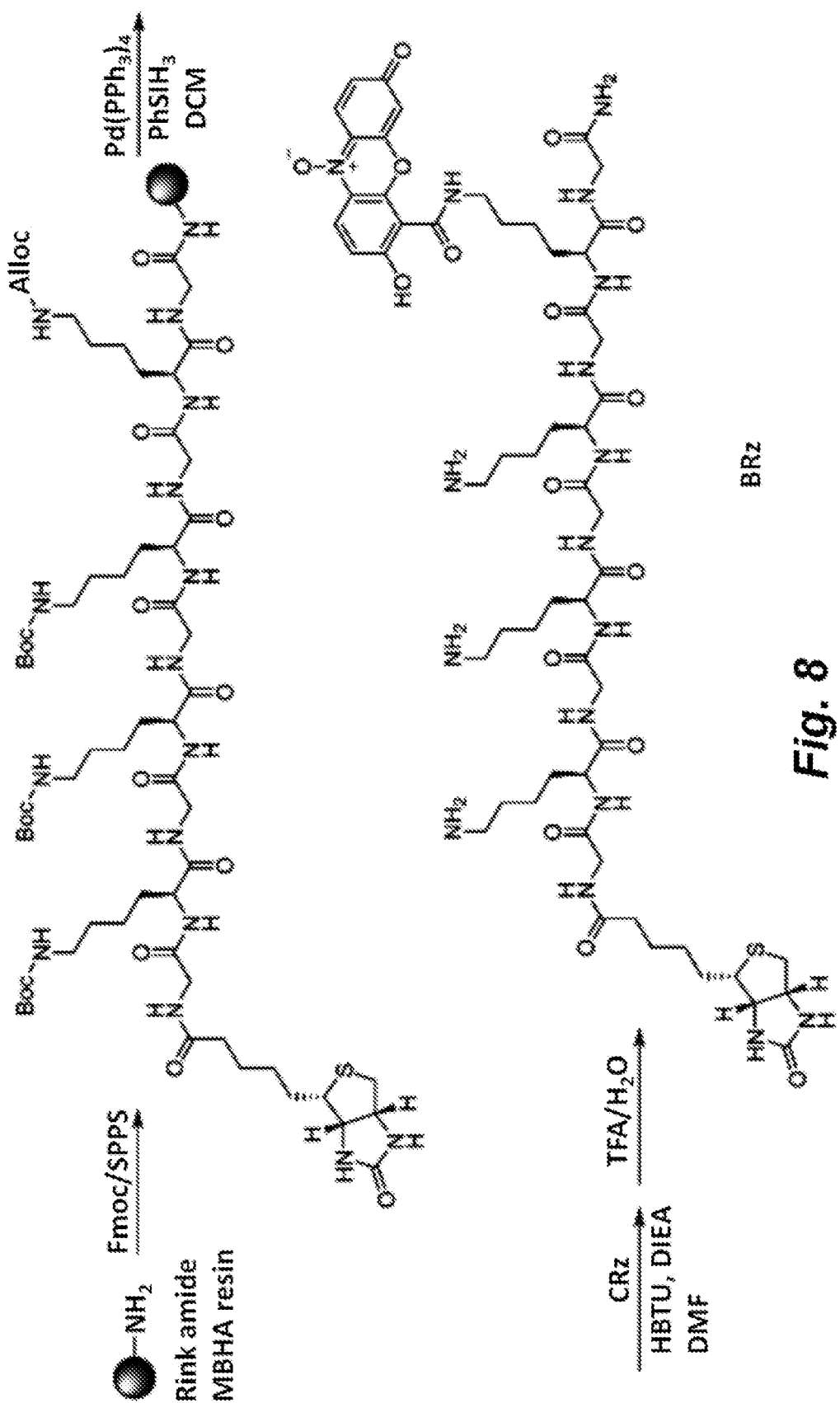
FIG. 8. Synthesis of the biotin-modified CRz (BRz). The GKGKGK (SEQ ID NO:1) sequences were added to improve the solubility of the product.

An illustrative, but non-limiting, synthesis protocol for a biotin-modified CRz (BRz) is shown in FIG. 8. The GKGKGK (SEQ ID NO:1) sequences were added to improve the solubility of the product. This BRz structure has been shown to be a useful probe.

Figure 38:
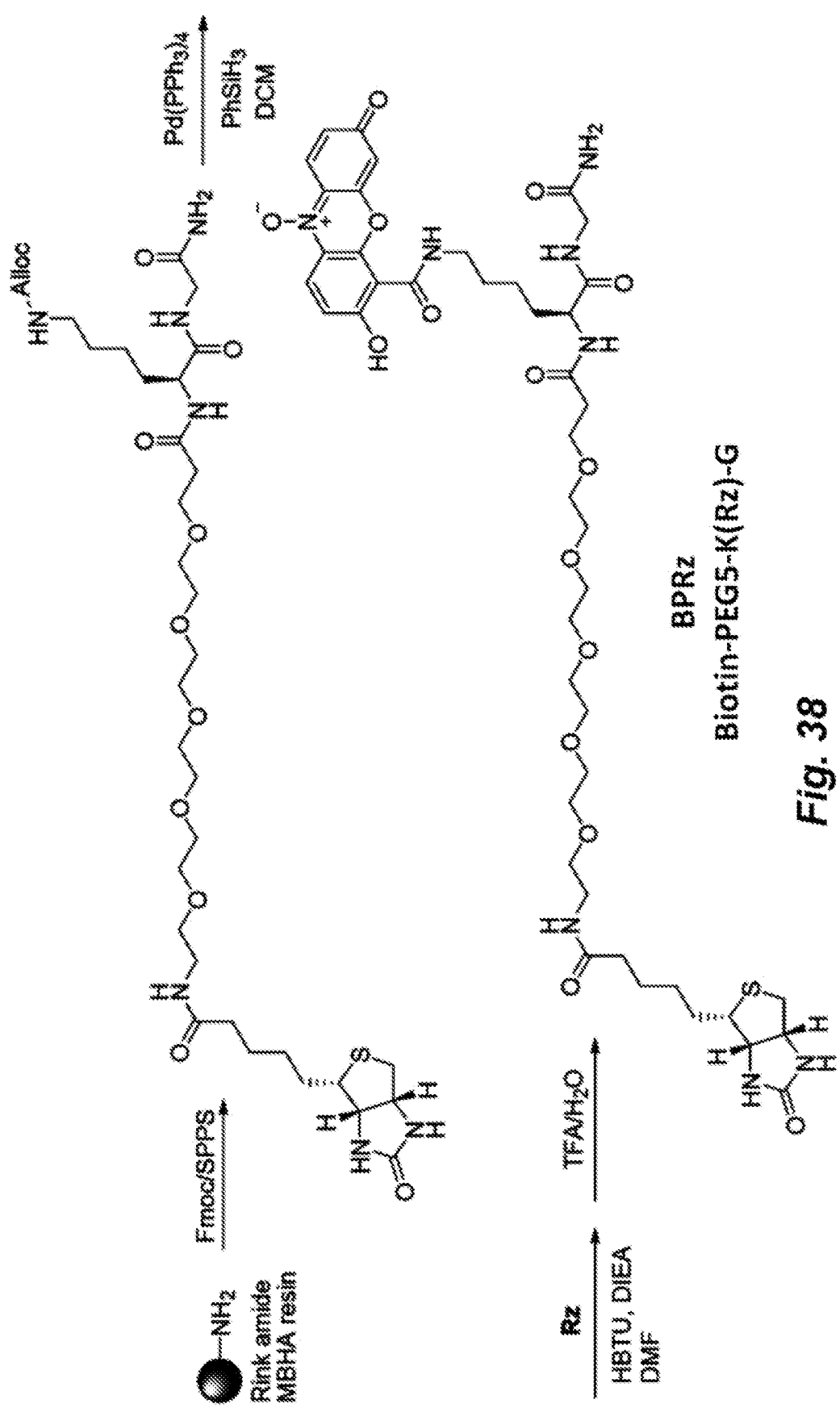
FIG. 38. Synthesis protocol for a biotin-functionalized resazurin (Biotin-PEG5-K(Rz)-G) where the biotin is attached to the resazurin by a linkage comprising polyethylene glycol.
Figure 39:
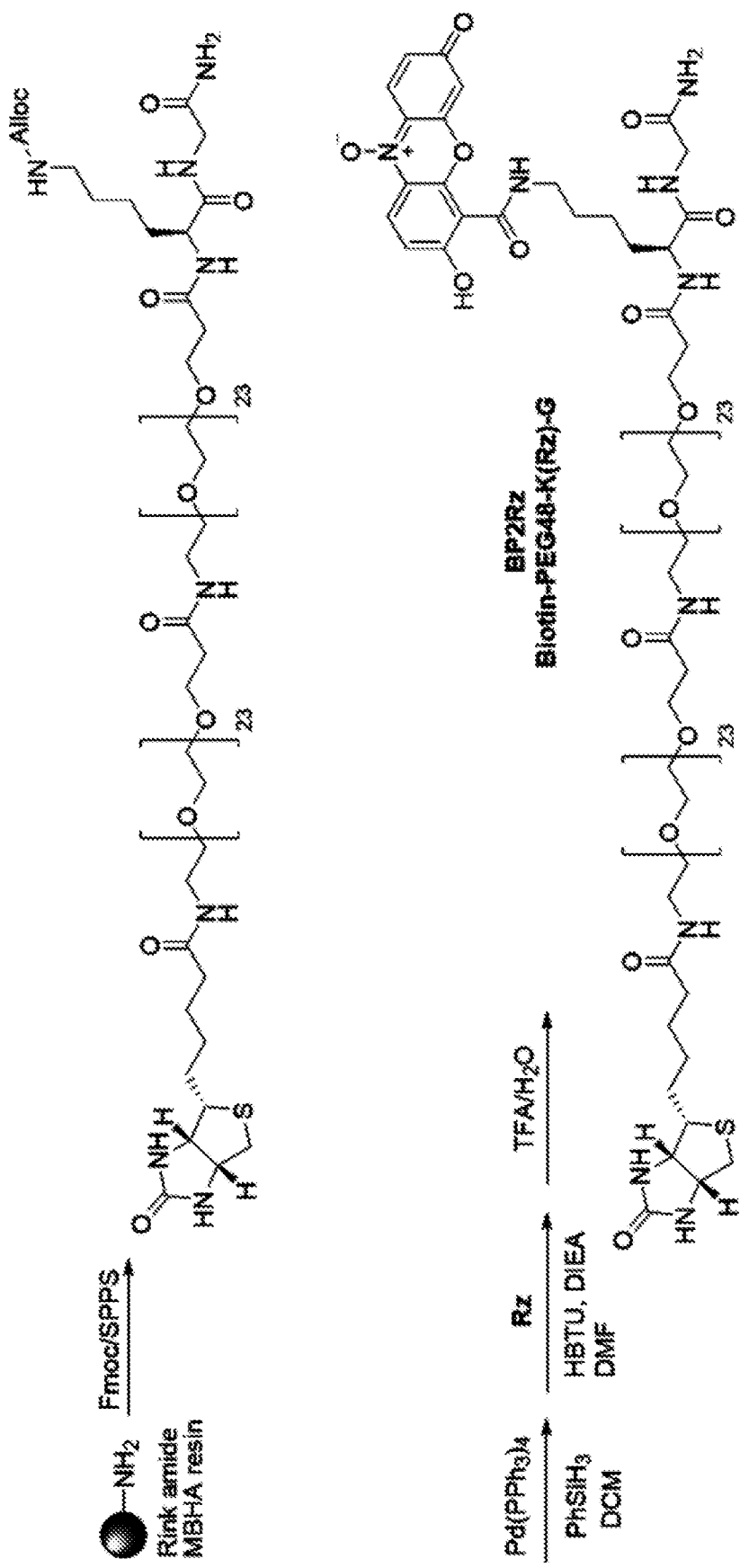
FIG. 39. Synthesis protocol for another biotin-functionalized resazurin (Biotin-PEG48-K(Rz)-G) where the biotin is attached to the resazurin by a linkage comprising polyethylene glycol.

As indicated above, in certain embodiments the biotin-functionalized resazurin probe comprises a biotin attached to the resazurin by a linker comprising a polyethylene glycol. Illustrative, but non-limiting synthesis schemes illustrating the synthesis of a biotin attached to a resazurin by a linkage comprising a polyethylene glycol (PEG) are shown in FIGS. 38 and 39.

The foregoing is illustrative and non-limiting. Using the teachings provided herein, numerous other functionalized resazurin/resorufin probes will be available to one of skill in the art.

Microfluidic Devices Comprising Resorufin.

As explained above, the functionalized resazurin/resorufin probes described herein can readily be attached to a surface and in certain embodiments the surface comprises a surface in a microfluidic device. In various embodiments microfluidic devices comprise microwell arrays, or microwell cartridges, or microfluidic devices comprising a plurality of microchannels and/or microchambers. Microfluidic devices are well known in the art and typically include one or more microfluidic chips and, in certain embodiments, may additionally comprise fluid-moving devices such as sippers or pipettes. In certain embodiments the microfluidic chips have at least one microchannel, and may include any number of channels within the dimensions of the microfluidic chip. Examples of microfluidic devices known in the art include, but are not limited to, Chow et al. (U.S. Pat. No. 6,447,661), Kopf-Sill (U.S. Pat. No. 6,524,830), Spaid (U.S. Pat. No. 7,101,467), Dubrow et al. (U.S. Pat. No. 7,303,727), Schembri (U.S. Pat. Nos. 7,390,457 and 7,402,279), Takahashi et al. (U.S. Pat. No. 7,604,938), Knapp et al. (U.S. Patent Application Publication No. 2005/0042639), Hasson et al. (U.S. Patent Application Publication No. 2010/0191482), and the like.

In one illustrative, but non-limiting embodiment the microfluidics device comprise a single cell barcode chip (SCBC). SCBCs are well-known to those of skill in het art are described, for example, in U.S. Patent Pub. No: 2016/0238594, by Xue et al. (2015) *J. Am. Chem. Soc.*, 137:4066-4069, by Shi et al. (2012) *Proc. Natl. Acad. Sci. USA*, 109 (2): 419-424, and the like.

Figure 18:
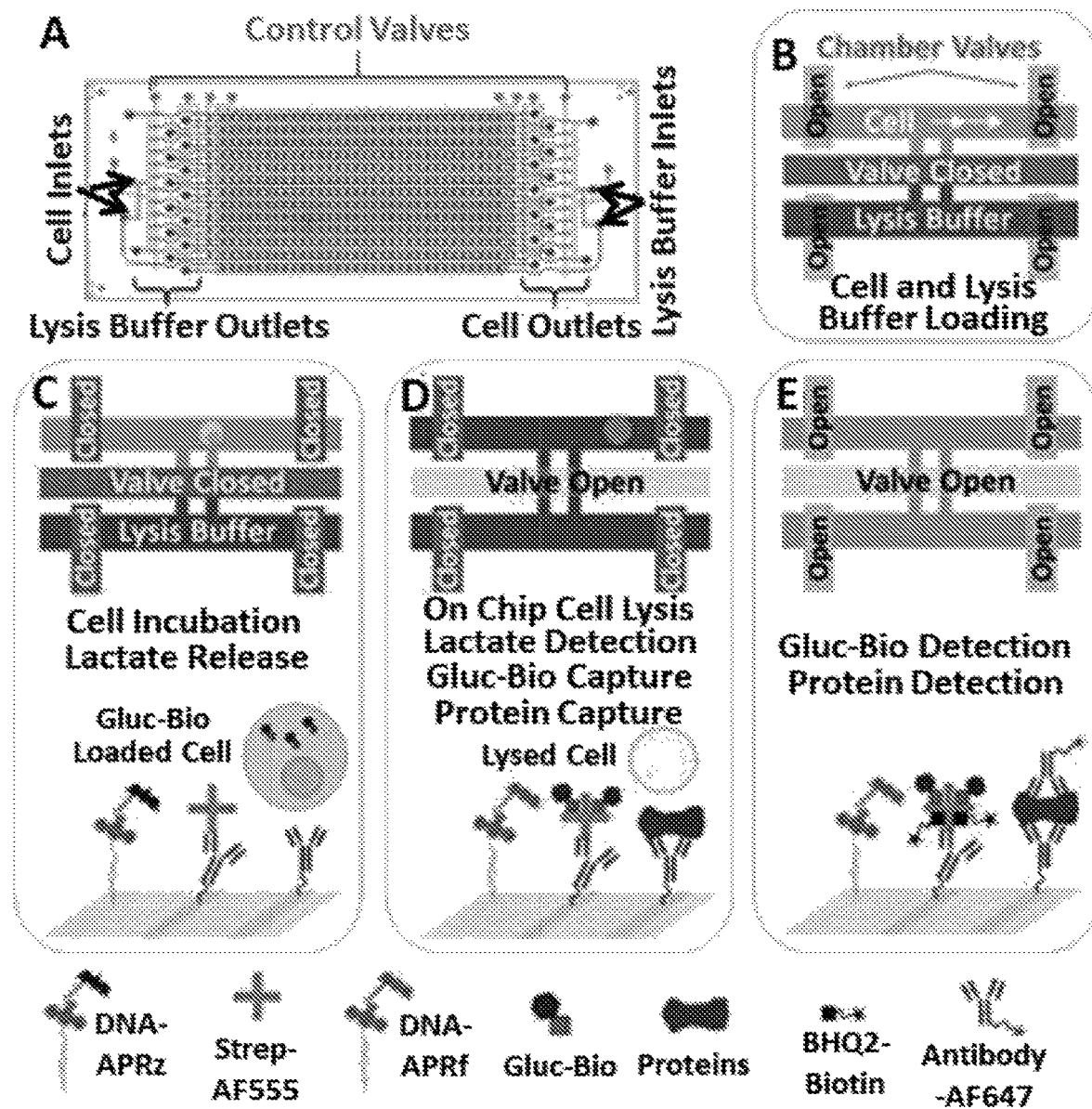
FIG. 18. Panel a) The layout of the SCBC device. Panels b-e) Schematic representation of a micro chamber in the SCBC device and the operation protocol of the device. Cells were first loaded with a glucose analog (GlucBio) and subsequently isolated, incubated and lysed in individual chambers. Panel f) The principle of protein detection using sandwich immunofluorescence assays. Panel g) The mechanism of glucose uptake quantification using glucose-biotin as a surrogate. The SCBC platform, excluding the lactate detection, has been described in detail in our previous study (Xue et al. (2015) *J. Am. Chem. Soc.* 137:4066-4069).

In certain embodiments the SCBC chip comprises a plurality of microchambers having a dimension that allows them to hold one or at most a few mammalian cells. In certain embodiments the microchambers have a volume less than about 5 nL, or less than about 4 nL, or less than about 3 nL, or less than about 2 nL. In certain embodiments the microchambers have a volume of about 1.5 nL. In certain embodiments the SCBC chips comprise at least 2, or at least 4, or least 10, or at least 50, or at least 100, or at least 150, or at least 200, or at least 250, or at least 300, or at least 350 microchambers. In one illustrative, but non-limiting embodiment the SCBC comprises 310 1.5 nL microchambers (FIG. 18, panel a).

Cells can be loaded into each chamber and, in various embodiments, each chamber contains a full barcode array. In certain embodiments each microchamber has a companion lysis buffer reservoir separated by a programmable valve (see, e.g., FIG. 18, panel b, Shi et al., supra.). In certain embodiments, for protein assays, specific stripes in the barcode represent a spatial address upon which a sandwich immunofluorescence assay for a specific protein can be executed. Each barcode stripe can be initially patterned with a unique ssDNA oligomer, and the barcode is converted into an antibody array using the DNA-encoded antibody library (DEAL) approach (see, e.g., Bailey et al. (2007). *J. Am. Chem. Soc.*, 129 (7): 1959-1967), and/or can be used to couple/immobilize a resazurin/resorufin probe as described herein.

The assays can be can be calibrated in absolute terms, and each individual assay can be analyzed for cross-reactivity against all other assays. Typically, each assay will be localized to a particular barcode stripe, yield a fluorescent output, and may be automatically executed using steps that are compatible with the other assays performed in the device.

In various embodiments the SCBC is configured to measure at least lactate production. In certain embodiments the SCBC is configured to additionally assay glucose uptake. In certain embodiments the SCBC is configured to additionally assay various proteins (e.g., signaling proteins). In certain embodiments the additional proteins include one or more of phosph-P70 kinase, EGFR, p53, phosphor-TOR, phosphor-ERK1, NDRG1, Phospho-Src, phosphoAkt1, and/or Ki67/MKI67.

The microfluidics platforms and the SCBC platforms described herein are illustrative and non-limiting. Using the teachings provided herein, other microfluidics devices comprising a resazurin/resorufin probe as described herein, and, in particular SCBCs comprising a resazurin/resorufin probe as described herein will be readily available to one of skill in the art.

Methods of Quantifying Analytes.

In various embodiments the resazurin/resorufin probe(s) described herein can be used to detect and/or to quantify essentially any analyte that can be enzymatically coupled to oxidation-reduction reactions. Accordingly, in certain embodiments, methods of detecting and/or quantifying a reducible or oxidizable analyte in a sample are provided. In certain embodiments the method involves contacting a sample (e.g., a cell lysate) with a resazurin/resorufin probe described herein attached to a solid support, wherein said sample further comprises enzyme(s) and/or substrates that enzymatically couple oxidation or reduction of the analyte with oxidation or reduction of the resazurin; and detecting a change in color or fluorescence of the resazurin, where the change in color or fluorescence comprises a measure of presence and/or quantity of the analyte.

As illustrated in Example 1, in certain embodiments this method is utilized to quantify lactate production by a cell. As described herein, in various illustrative, but non-limiting embodiments the method can involve providing a cell lysate from the cell(s) that are to be assayed, and contacting the lysate with a resazurin/resorufin probe described herein and enzymes and/or substrates that catalyze and couple the oxidation of lactate to the reduction of NAD or NADP where the reduction of NAD or NADP converts the resazurin to resorufin providing a fluorescent (or color) signal that is a measure of the amount of lactate produced by the cell(s). In certain embodiments the enzymes and/or substrates that catalyze and couple the oxidation of lactate to the reduction of NAD or NADP comprise lactate dehydrogenase, nicotine adenine dinucleotide (NAD), and diaphorase.

The quantification of lactate is illustrative and non-limiting. One of skill in the art will readily recognize that utilizing the teachings provided herein numerous other analytes can be detected and/or quantified using the resazurin/resorufin probes described herein. Such analytes include, but are not limited to formate, glutamate, triacylglyceride, hydroxylglutarate, malate, fumarate, succinate, citrate, and the like.

In certain embodiments the methods and devices described herein can be used to evaluate the effect of one or more test agents on a cell. In certain embodiments the method involves contacting the cell with said test agent(s); and performing a method as described above, determine at least the lactate production of the cell where the effect of the test agent(s) on the lactate production is determined. In certain embodiments the method additionally involves quantifying glucose uptake, e.g., as described in Example 1. In certain embodiments the method additionally involves detecting one or more proteins (e.g., one or more of phosph-P70 kinase, EGFR, p53, phosphor-TOR, phosphor-ERK1, NDRG1, Phospho-Src, phosphoAkt1, and/or Ki67/MKI67 and the like.

Kits.

In various embodiments kits for the detection of lactate and/or other analytes are provided. In certain embodiments the kits comprise a resazurin/resorufin probe as described herein and/or a device (e.g., a microfluidic device) comprising a resazurin/resorufin probe as described herein. In certain embodiments the kits additionally include enzyme(s) and/or substrates that enzymatically couple oxidation or reduction of the analyte of interest with oxidation or reduction of the resazurin.

In certain embodiments the kit is for the quantification of lactate and the kit additionally includes enzyme(s) and/or substrates that enzymatically couple oxidation or reduction of the lactate of interest with oxidation or reduction of the resazurin. In certain embodiments the kit includes one or more of lactate dehydrogenase, nicotine adenine dinucleotide (NAD), and diaphorase.

In certain embodiments the kit comprises instructions (instructional materials) for using the kit for quantification of one or more target analytes.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Surface Immobilization of Redox-Labile Fluorescent Probes Enables Single Cell Profiling of Aerobic Glycolysis Activities Herein, we report on a chemical method for quantifying lactate production from single cells using a surface-immobilized redox-labile fluorescent probe and coupled enzyme reactions (FIG. 1, panel a). This approach was designed to be compatible with our previously reported SCBC platform (FIG. 1, panel b).[5] By integrating the quantitation of lactate production with glucose influx, as well as assays for key elements of the epidermal growth factor receptor (EGFR) signaling pathway, we were able to interrogate a glycolysis-addicted patient-derived EGFR variant III (EGFRvIII) mutant glioblastoma neurosphere model (GBM39) under different therapeutic perturbations. We resolved the aerobic glycolysis activity and its interplay with the oncogenic signaling at the single-cell level.

The lactate detection in this study was based on the surface-immobilized resazurin/resorufin as the fluorescence reporter (FIG. 1, panel a). The resazurin/resorufin pair has been widely employed in various analytical methods for redox-active metabolites due to its fast reaction kinetics and prominent fluorescence spectra changes in detecting NADH—a common mediator of enzymatic redox processes.[9] However, those studies were exclusively carried out in bulk solutions. To the best of our knowledge, there is no report of incorporating this redox pair for surface-based biosensor construction. This is probably due to the challenges in immobilizing resazurin, whose redox lability could lead to insufficient probe stability and poor assay sensitivity.

Figure 2:
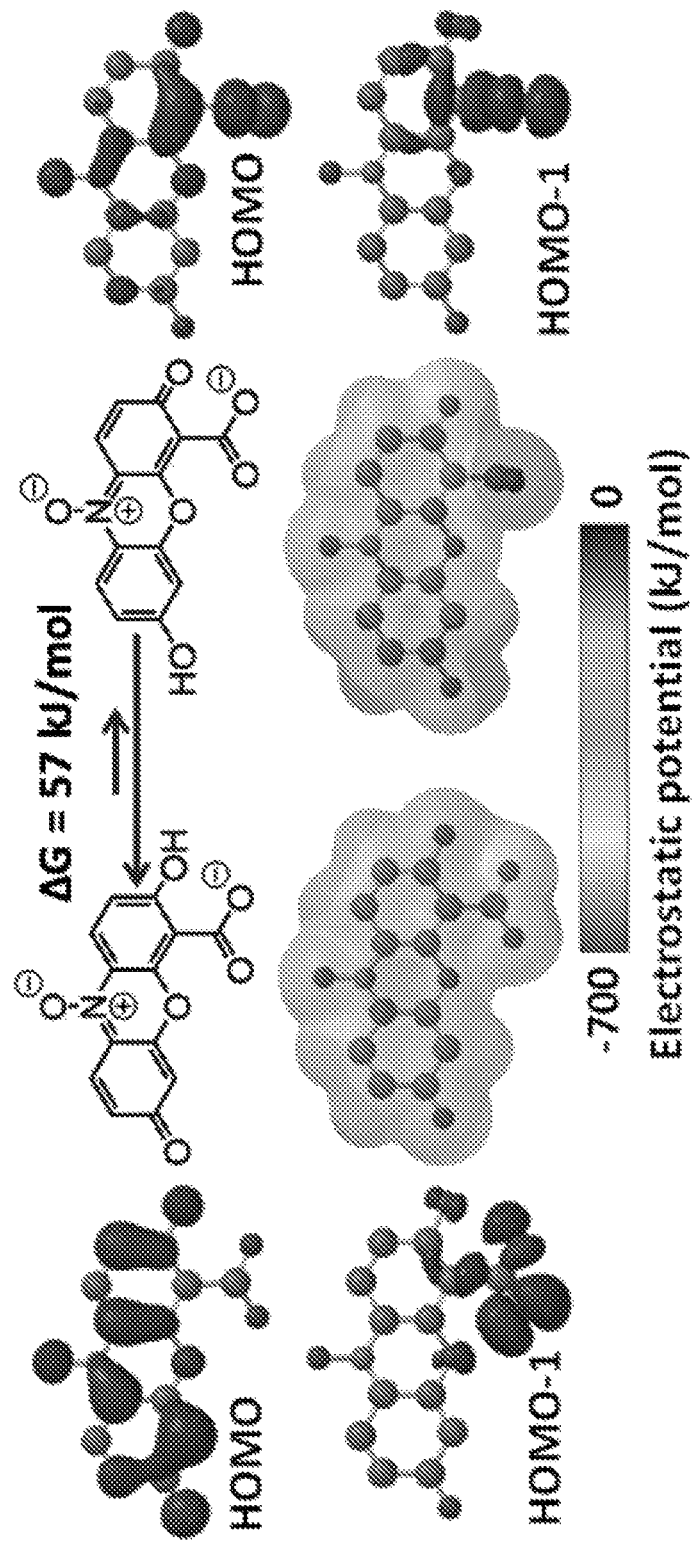
FIG. 2. Electrostatic potential and molecular orbital calculations reveal that the dominant salicylic isomer has compromised nucleophilicity and is unsuitable for further conjugations.
Figure 5:
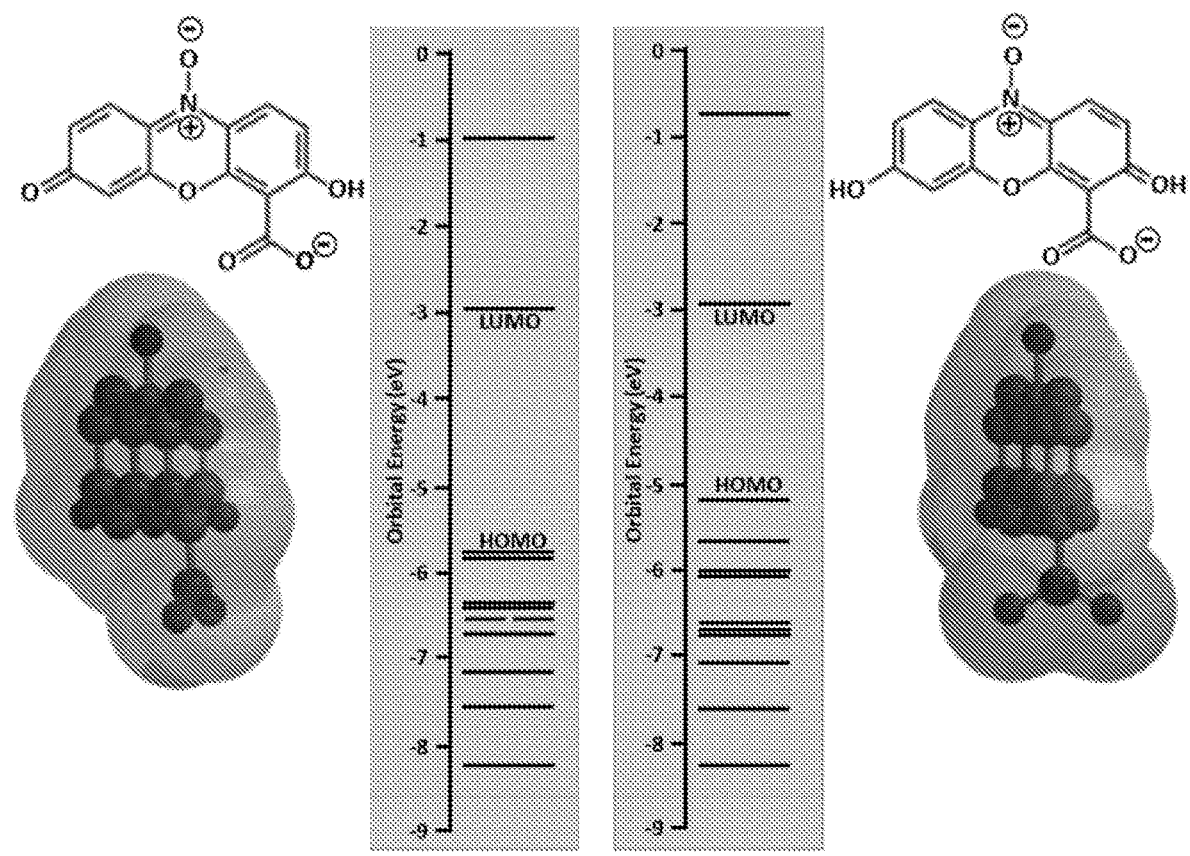
FIG. 5. Calculated energy levels and electrostatic potentials for the two CRz isomers. The salicylic acid form is of lower energy and adopts a planer geometry. In contrast, the carboxyl group in the quinone form is out of the aromatic plane. The calculation was performed on Spartan software (Wavefunction, Inc. 2016) using density functional method, with EDF2 functional and 6-31G*basis sets. Calculation was carried out in a solvent environment with a dielectric constant of 78 (water) using CPCM model.

As the starting point for attempting resazurin immobilization, we first synthesized 4-carboxyresazurin (CRz) to enable further conjugation. Other modifications to resazurin, such as the alkylation and acetylation on the phenolic hydroxyl group, render the resulting resorufin counterparts non-fluorescent. A closer investigation revealed that the CRz adopted the salicylic acid structure as the preferred configuration (FIG. 2, FIG. 5). Although both isomers demonstrated negative electrostatic potentials on the carboxyl groups, the salicylic form exhibited a weaker and more dispersed potential. In addition, the highest occupied molecular orbital (HOMO) for the salicylic form involved no contribution from the carboxyl group. In comparison, the carboxyl-quinone isomer had a more carboxyl-centric HOMO. All these factors contribute to the strongly compromised reactivity of the carboxyl group. As a result, direct conjugation of CRz to the surface led to negligible yield. In order to improve the CRz reactivity, we converted the aromatic carboxylic group to aliphatic reactive groups. Four types of extended CRz structures bearing amine, carboxyl, biotin and azide functional groups were successfully synthesized at appreciable quantities (FIGS. 6-9). These functional groups provided the basis for surface immobilization reactions.

Figure 10:
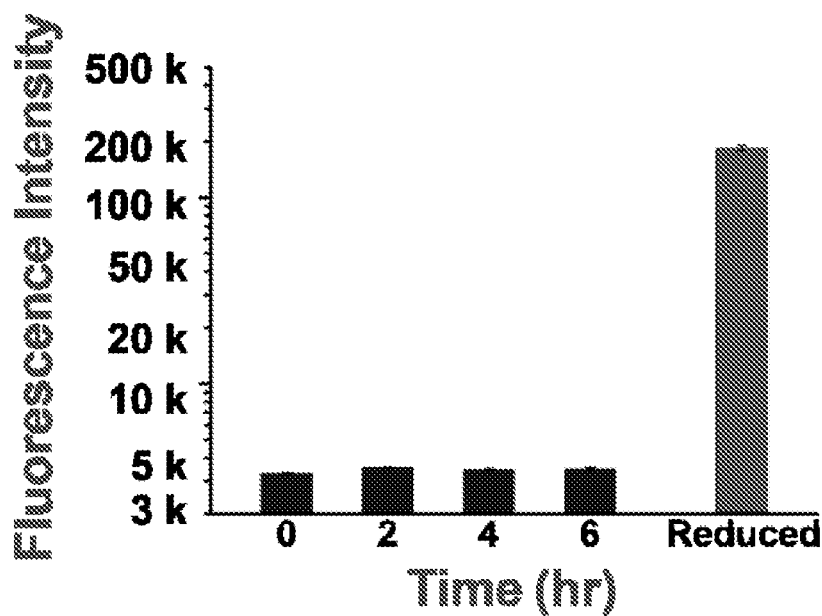
FIG. 10. Stability of Biotin-modified CRz (BRz) in solution phase. 8 μM in PBS. At 6 hrs, all the BPRz was reduced through adding 10 units of Diaphorase and 1 mM of NADH in PBS.
Figure 11:
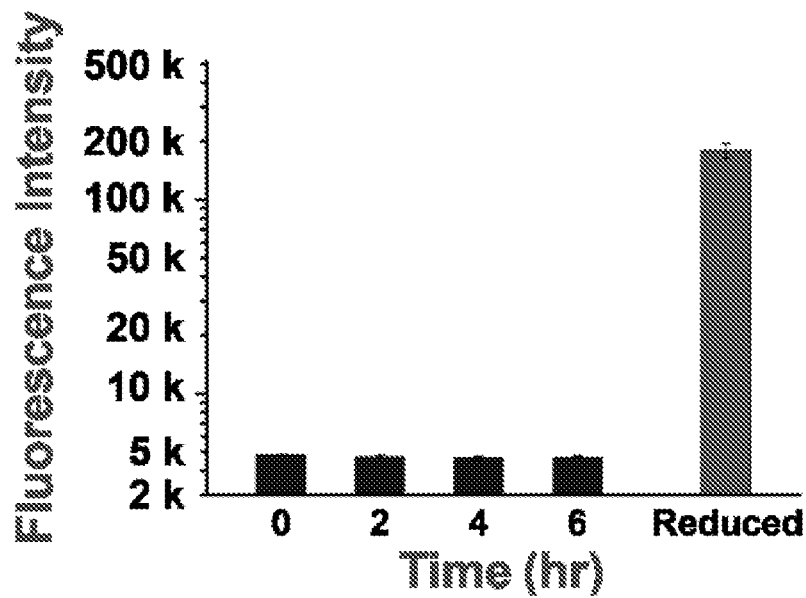
FIG. 11. Stability of the APRz probe (8 μM in PBS). The "reduced" signal was obtained through adding 10 units of Diaphorase and 1 mM of NADH to the APRz solution followed by a 1 hour incubation.

In order to be adapted to the SCBC platform, the probe immobilization process should be compatible with the single-stand DNA hybridization process.[5] However, the N-oxide group on CRz confers strong redox lability. Consequently, the attempt of conjugating the amine-modified CRz to a single strand DNA (ssDNA) was unsuccessful. Likewise, ssDNA coupled to carboxyl-modified CRz suffered from spontaneous reduction. On the contrary, both the biotin-modified CRz (BRz) and azide-modified CRz (APRz) demonstrated superior stability (FIGS. 10, 11).

Figure 12:
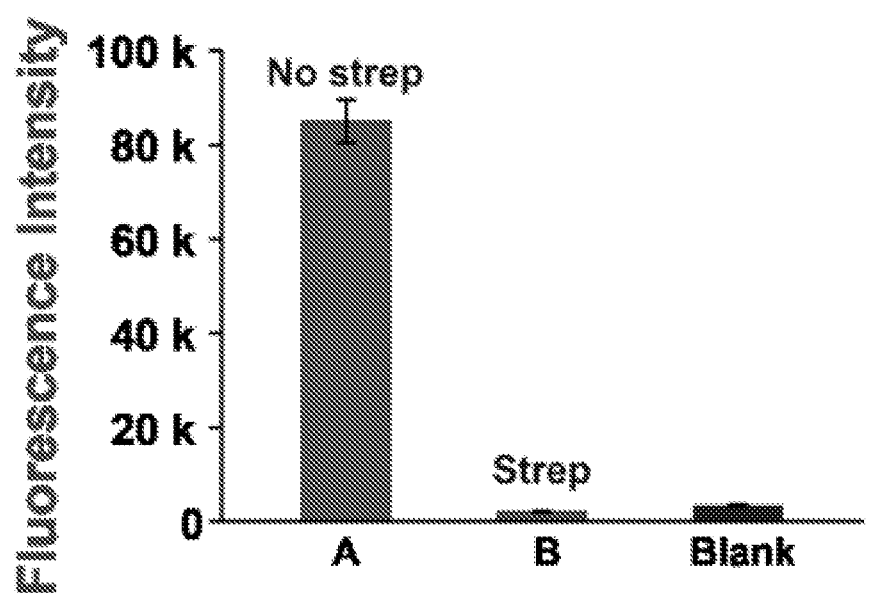
FIG. 12. Fluorescence quenching effect of the Biotin-modified CRf (BRf) by streptavidin. More than 4 equivalents of streptavidin was used.
Figure 14:
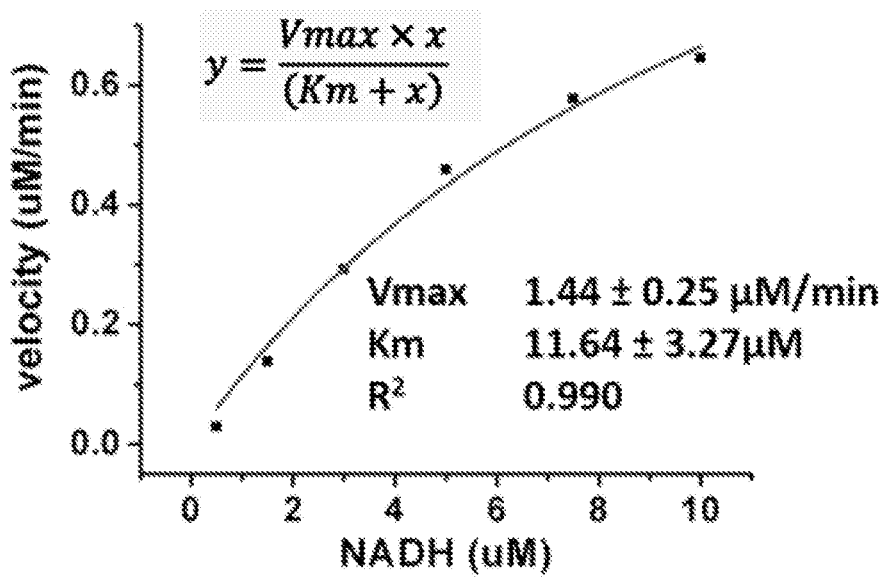
FIG. 14. Michaelis-Menten kinetics curves for (panel a) APRz (panel b) resazurin in the diaphorase catalyzed NADH oxidation reaction. The concentration for APRz and Resazurin were both 10 μM in PBS. The lines were obtained through fitting with Michaelis-Menten functions.
Figure 14:
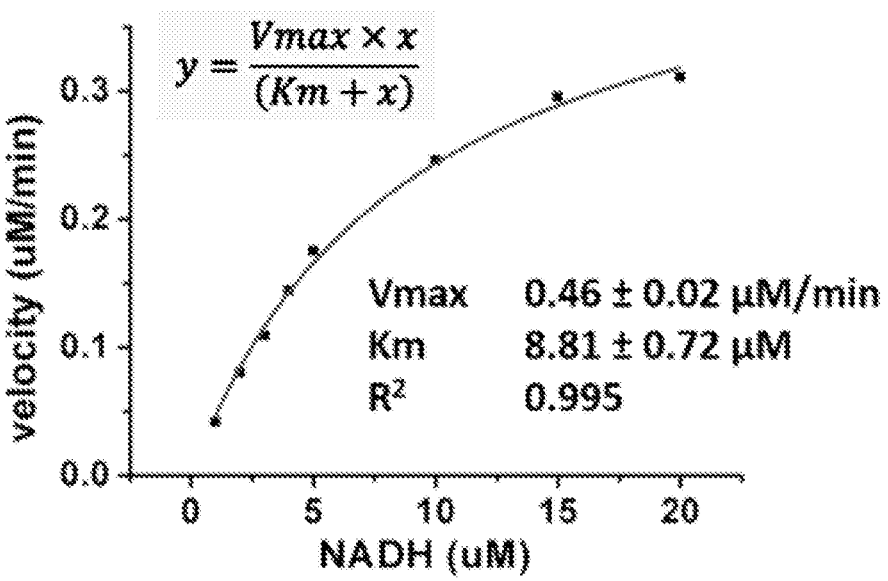

We then evaluated the BRz and APRz probes for their performance in lactate detection experiments. BRz was immobilized onto the surface through ssDNA-streptavidin conjugates. Similarly, dibenzocyclooctyne-modified ssDNA enabled surface grafting of APRz molecules (FIG. 3, panel a).[10] The resazurin-modified surfaces were exposed to a solution containing a mixture of sodium lactate, nicotinamide adenine dinucleotide (NAD+), lactate dehydrogenase (LDH) and diaphorase. In this case, the enzyme reaction cascade shown in FIG. 1, panel a translates the lactate quantity to fluorescence readouts. As shown in FIG. 3, panel b, BRz exhibited unsatisfactory fluorescence increase. Further investigation revealed that the resorufin fluorescence was severely quenched by streptavidin (FIG. 12). On the other hand, APRz probes exhibited almost ten-fold increase of fluorescence intensity after lactate conversion (FIG. 3, panel b). More interestingly, the reduced APRz exhibited higher fluorescence intensity than unmodified resorufin (FIG. 13), possibly due to the intramolecular hydrogen bond stabilizing the structure. In addition, the APRz showed faster reaction kinetics in the diaphorase catalyzed NADH oxidation reaction than unmodified resazurin, demonstrating its superior performance (FIG. 14).

Figure 16:
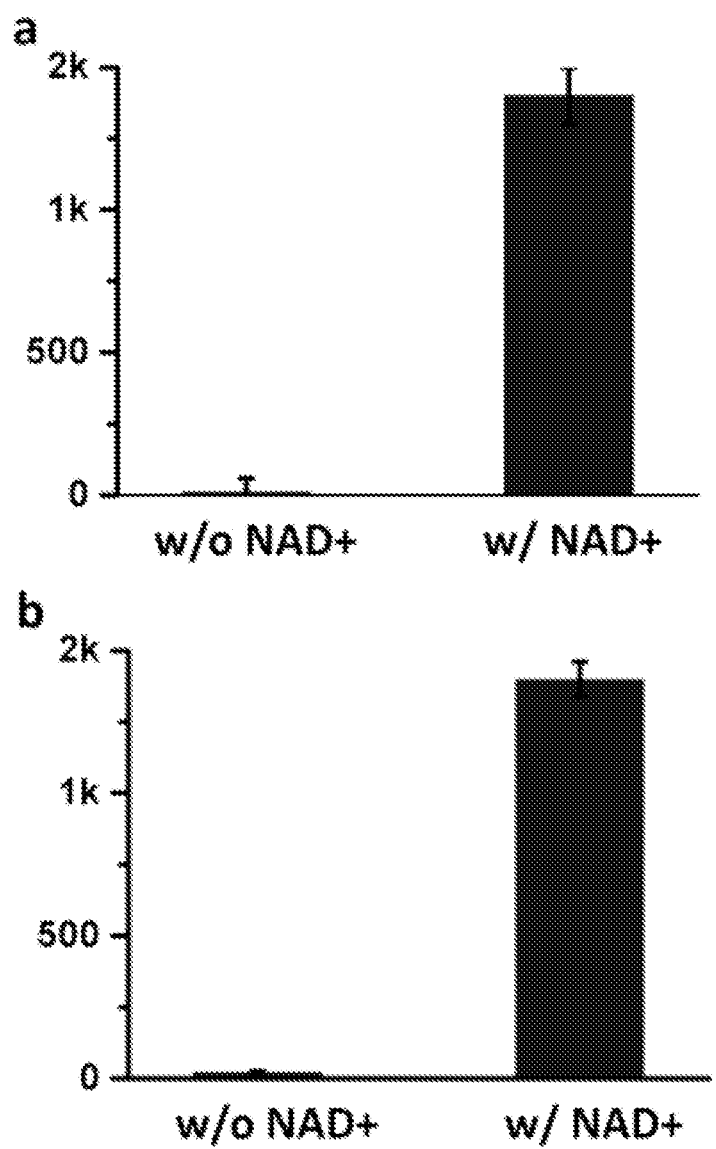
FIG. 16. Lactate assay results using (panel a) GBM39 cell lysates and (panel b) WM 266-4 cell lysates. APRz-DNA complex were immobilized on the slides first and then the mixture of diaphorase and LDH, cell lysate w/o NAD+, or cell lysate/NAD+ were added. Background fluorescence value obtained from a lysis buffer control was subtracted and the data was normalized for comparison.
Figure 17:
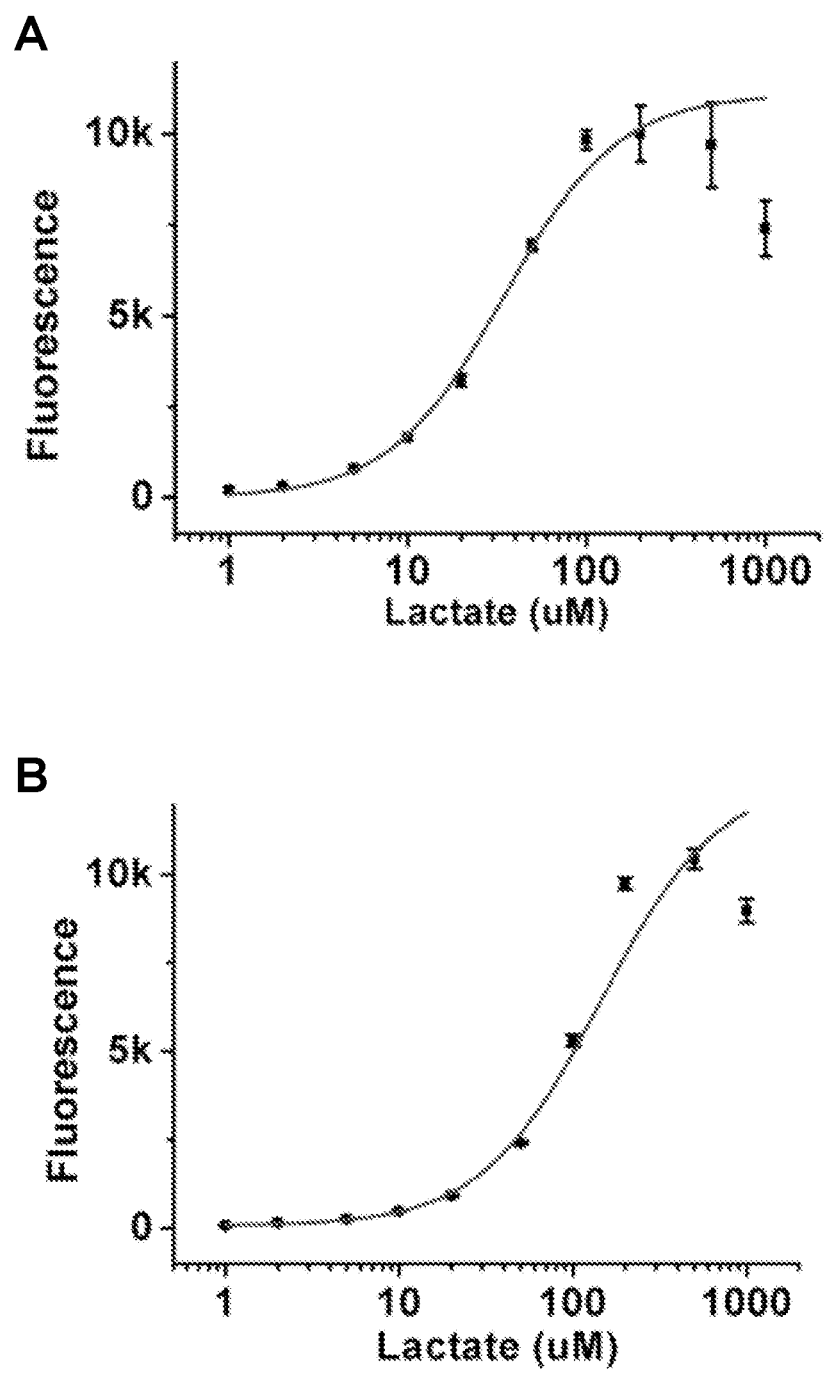
FIG. 17. Working curve for (panel a) APRz and (panel b) resazurin in solution phase, both at concentration of 8 μM in PBS. The curves were obtained through fitting with Hill functions. Both APRf and resorufin exhibit self-quenching at concentrations higher than the biologically-relevant range.

A potential concern of employing the enzymatic mechanism for lactate quantitation was the specificity of the method. The complex intracellular contents always pose strong challenges on such redox-based methods. In order to validate the detection scheme, we assessed the potential interference from common intracellular reducing agents such as glutathione and ascorbic acid, as well as glucose and glutamine. We found that all these compounds exhibited very slow reaction kinetics and led to insignificant fluorescence increase within the assay duration (FIG. 3, panel c, FIG. 15). In order to evaluate the combined interference from all intracellular components, we further performed validation using GBM39 cell lysates. Indeed, without the addition of extra NAD+, the reduction of APRz was negligible (FIG. 3, panel d, FIG. 16). This result was because the endogenous NAD (P) H level was two to three magnitudes lower than that of the lactate, and cells constantly produced lactate. Therefore, the intracellular NAD (P) H would contribute only negligibly to the observed fluorescence signal. In addition, by providing excess amount of LDH and NAD+, the conversion of lactate would be significantly preferred. We also found that the increase of fluorescence intensity corresponded well with the lactate concentration, both in the solution phase and on the surface (FIG. 3, panels e, f, FIG. 17). Particularly, the dynamic range of the surface APRz well covers the expected lactate concentrations at single cell level.[12] These results demonstrated that the APRz-based detection scheme was suitable for single cell lactate quantitation.

We then sought to adapt the lactate assay for single cell level quantitation. The surface-based lactate assay was incorporated onto the SCBC platform, which consisted of a two-layer elastomer microfluidics device coupled to a DNA barcoded glass slide.[5, 7] The device contained 384 programmable microchambers where cells were loaded and lysed for analysis. Each microchamber was equipped with a set of DNA barcode stripes, which served as a scaffold for multiplex measurements (FIG. 18). We quantified glucose uptake, lactate production and a panel of signaling proteins from GBM39 single cells. GBM39 is a human glioblastoma cell line that harbors a mutated form of the epidermal growth factor receptor (EGFR), which drives cell proliferation. Cells were treated with 1 μM of erlotinib (EGFR inhibitor), 0.1 μM of oligomycin A (ATPase inhibitor) or DMSO (control) before analysis.

Figure 4:
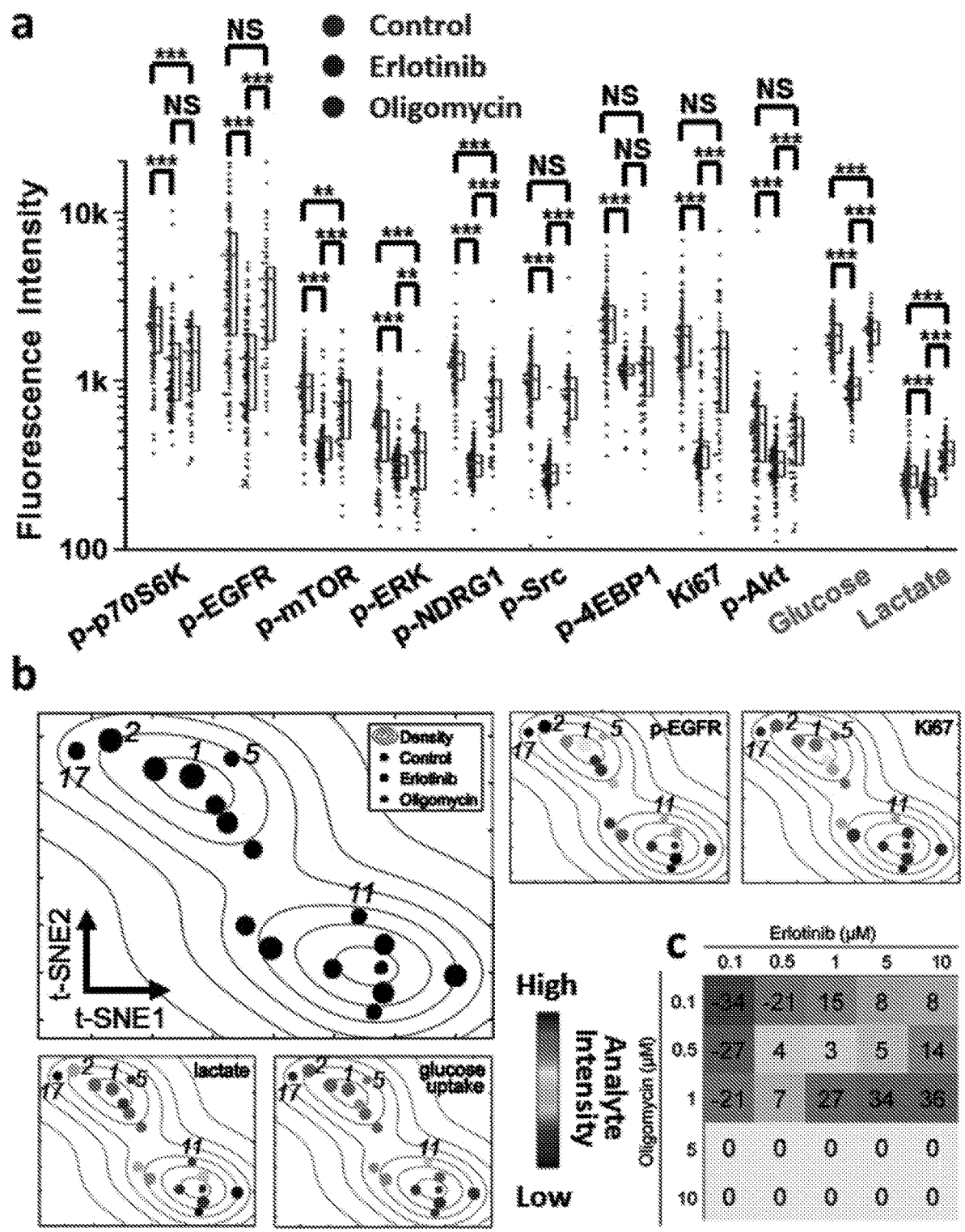
FIG. 4. Panel a) Scatter plot of the single cell dataset. Horizontal bars denote the average analyte levels and boxes represent the first and third quartiles of analyte distributions. Wilcoxon-Mann-Whitney significance levels: NS, $p>0.01$; , $p<0.01$; *, $p<0.001$. Panel b) t-SNE projection of the PhenoGraph clusters from GBM39 single cell dataset. Each cluster is represented by a single circle scaled to the number of cells in that cluster. The clusters are either color coded by the treatment conditions (the larger panel) or by median expression of indicated analytes (smaller panels). The numbers next to the circles denote the cluster name. Panel c) Synergistic effects observed in erlotinib and oligomycin co-treatment experiments on GBM39 cells. Positive numbers represent synergistic effects, and negative numbers represent antagonist effects.
Figure 19:
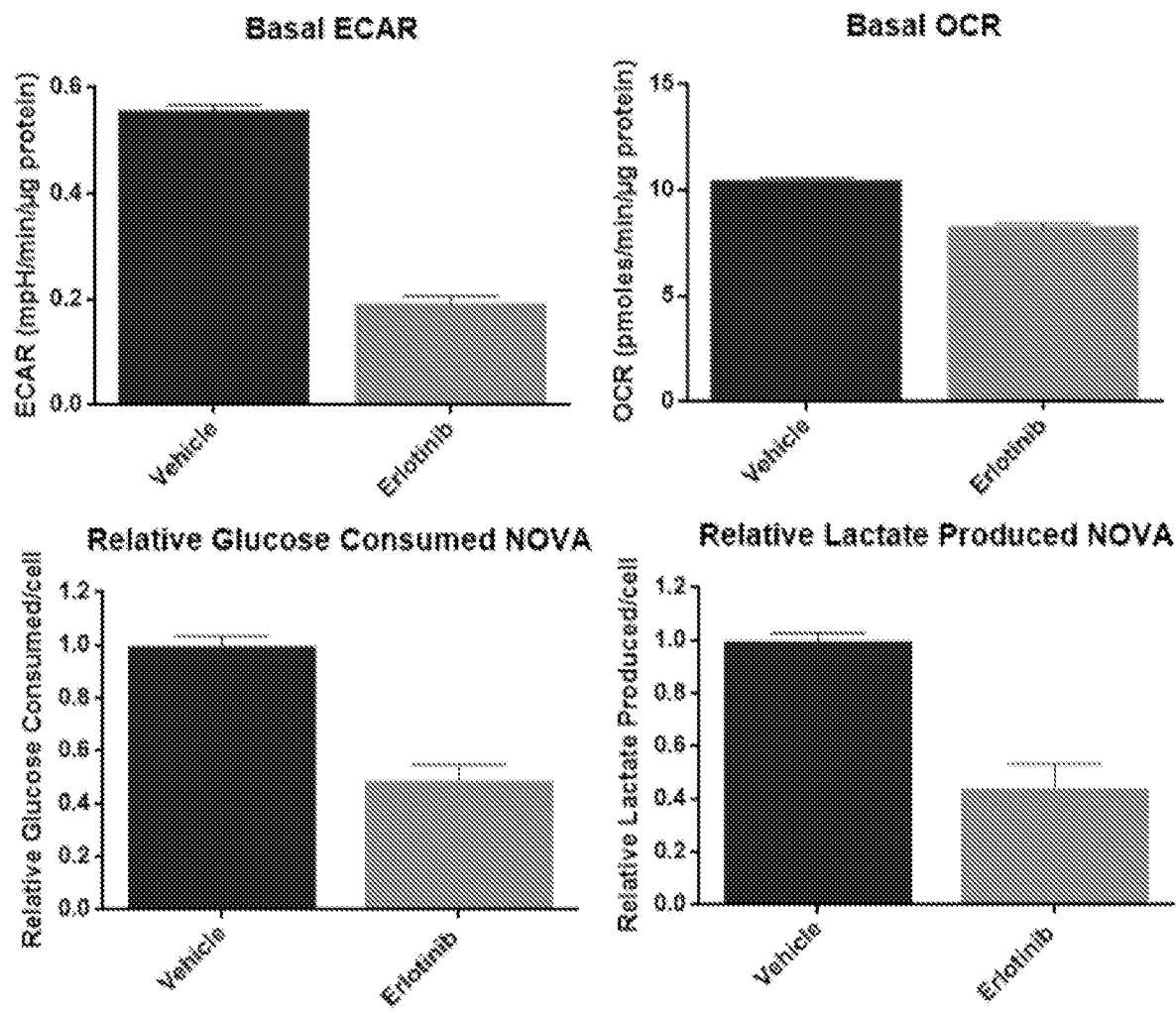
FIG. 19. (Upper) Extracellular acidification rate (ECAR) and oxygen consumption rate (OCR) per microgram protein of GBM39 cells after 10 mM glucose injection following 6 days of vehicle (DMSO) or 1 μM erlotinib treatment. Measurements were made with a Seahorse XFe24 Analyzer (error bars denote standard deviations among five repeats). (Lower) Glucose consumed and lactate produced measurements of GBM39 cells after 24 hrs of 1 μM erlotinib treatment relative to vehicle (DMSO). Measurements were made with a Nova Biomedical BioProfile Analyzer (error bars denote standard deviations among five repeats).

As shown in FIG. 4, panel a, erlotinib treatment dramatically decreased the glucose uptake capacity of GBM39 cells as well as their lactate production. Parallel measurements of oxygen consumption rate (OCR), extracellular acidification rate (ECAR), and lactate production on bulk GBM39 cells also lead to consistent results (FIG. 19). As a commonly used inhibitor in targeted chemotherapy, erlotinib prevents EGFR binding with ATP and inhibits its phosphorylation. This mechanism is consistent with our results, where significant down regulation of the phosphorylation levels on EGFR as well as downstream signaling proteins. On the other hand, under the treatment of oligomycin, GBM39 cells exhibited a slightly higher glucose uptake, but with significantly increased lactate production. These results dovetailed with the functioning mechanism of oligomycin, which inhibited ATP synthase and blocked the cellular electron transport chain, leading to elevated aerobic glycolysis activities. [14] Interestingly, oligomycin also appeared to suppress the phosphoproteins downstream of the EGFR signaling pathway, which implied that change of metabolic paradigm might also affect the oncogenic signaling network.

Figure 20:
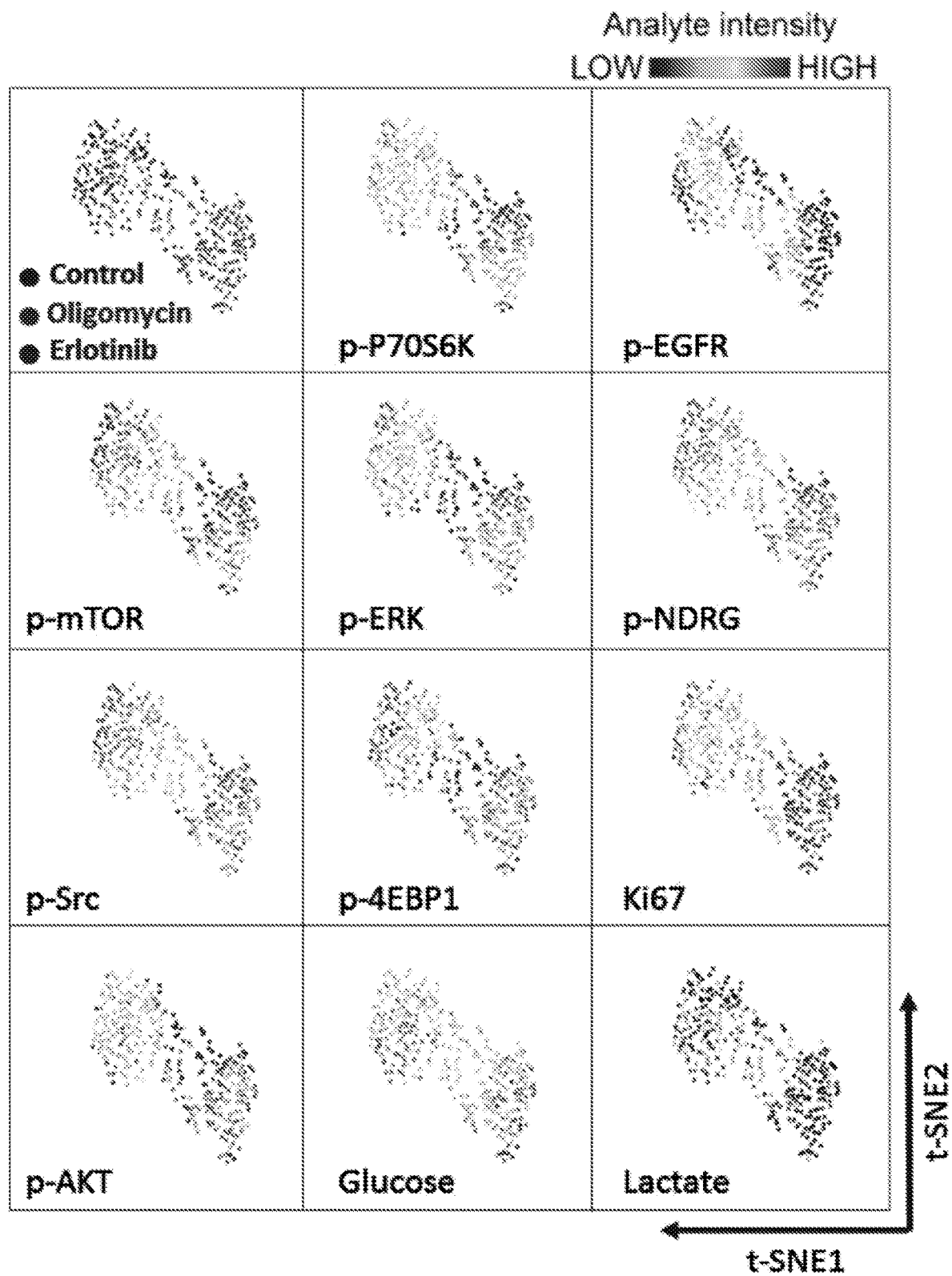
FIG. 20. viSNE display of the single cell data across the 3 test conditions. Cells are color coded by either the test conditions or the expression levels of the indicated analytes.
Figure 21:
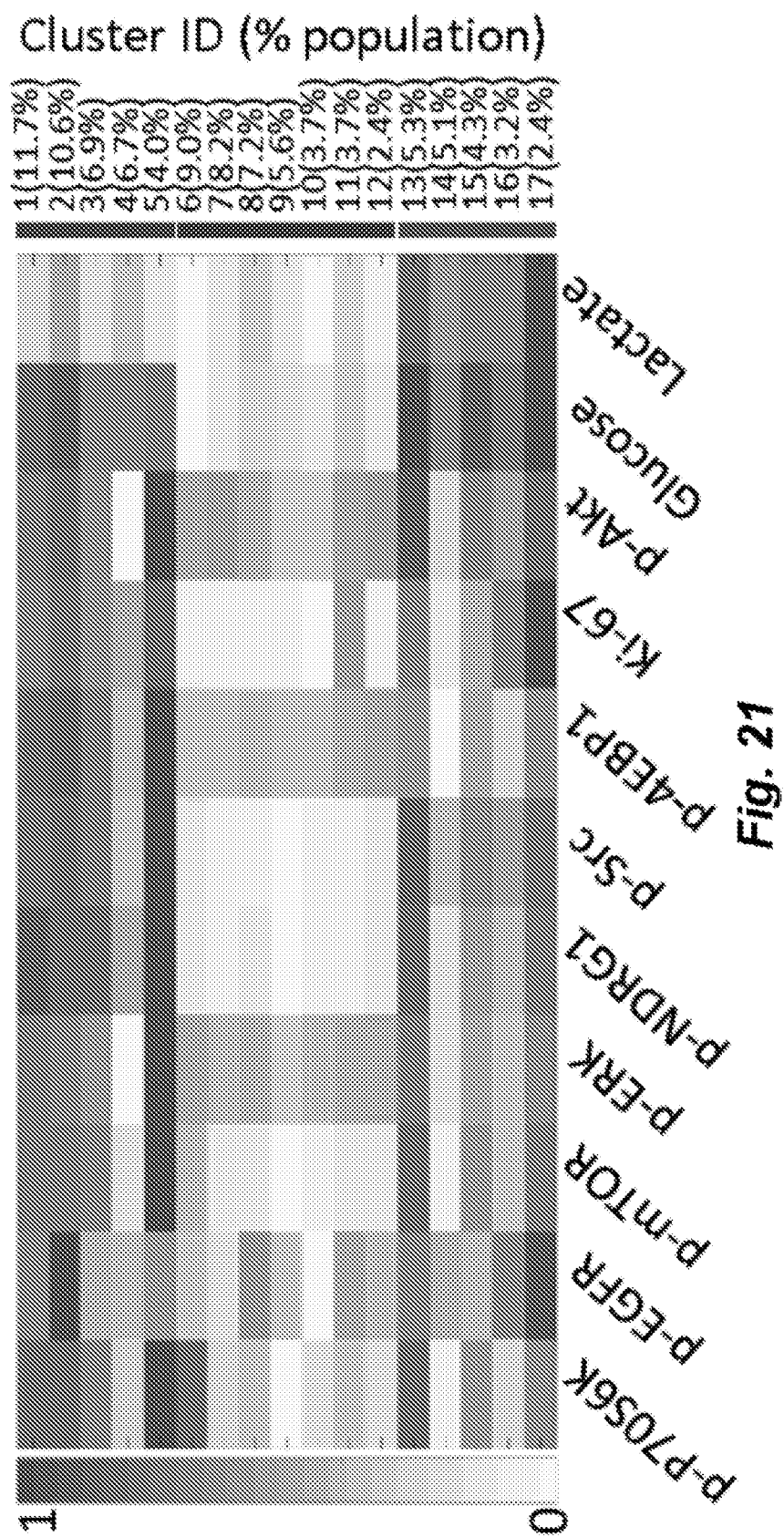
FIG. 21. Heatmap of the average analyte level in each cluster. Each analyte level has been rescaled to a 0 to 1 range across all the clusters. The percentage after each cluster ID denotes the cell number proportion of that cluster in corresponding samples. Samples were control, erlotinib, and oligomycin.
Figure 22:
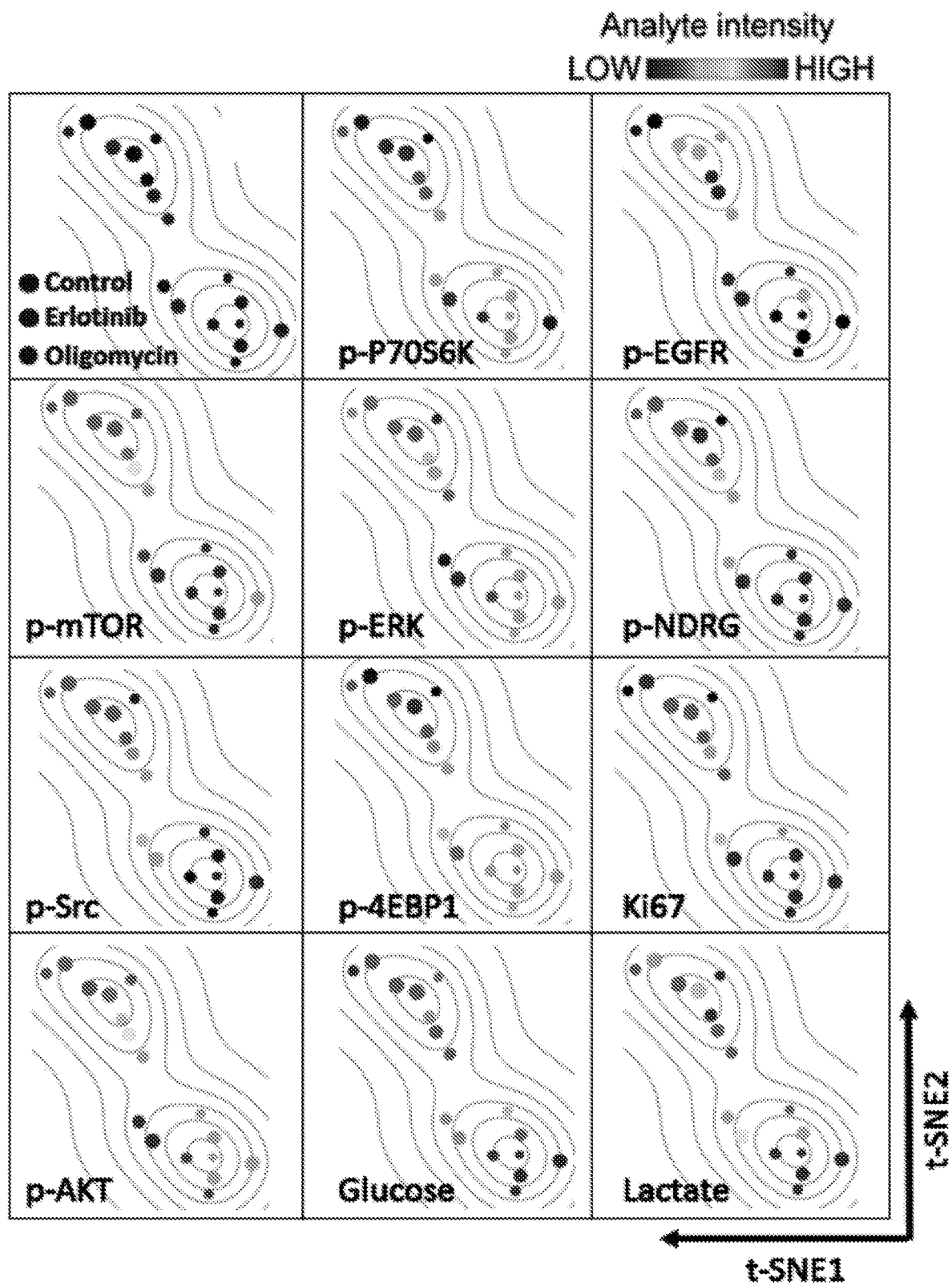
FIG. 22. PhenoGraph results for each of the analytes.

The single cell dataset contains rich information that can be mined through statistical analysis. To further dissect the interplay between aerobic glycolysis and phosphoprotein signaling, we employed the t-distributed stochastic neighbor embedding (t-SNE) to project the high-dimensional single cell data into a 2D space (FIG. 20). We further used PhenoGraph to partition these single data into subpopulations, using a nearest-neighbor method.[4a, 15] We resolved 17 subpopulations (clusters) across three treatment conditions (FIG. 4, panel b, FIG. 20-22). We found that glucose uptake level and lactate production were decoupled across many subpopulations, evidenced by their distribution patterns (FIG. 4, panel b, small panels). Even within the same sample group, the two analytes correlated poorly. For instance, cluster 1 and cluster 2 exhibited similar glucose uptake level but drastically different lactate production. This result proved that glucose uptake alone could not represent aerobic glycolysis activities at single cell level.

Figure 23:
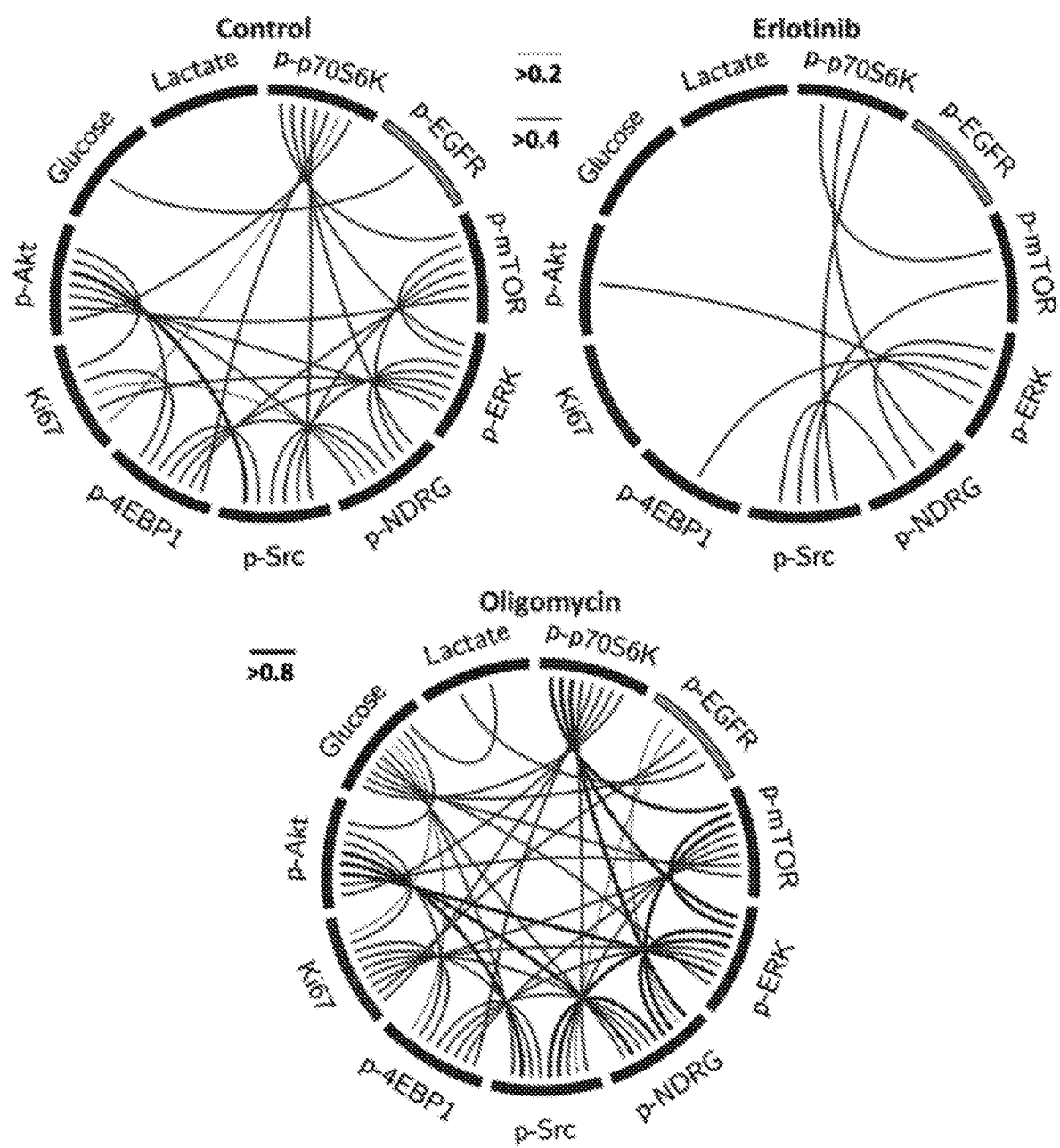
FIG. 23. Correlation networks resolved by GBM39 single cell profiling under control, erlotinib and oligomycin treatment conditions. Each line represents a statistically significant correlation between two analytes. The thickness of the line denotes the correlation amplitude. The graphs were generated using Circos software (Krzywinski et al. (2009) *Genome Res.* 19:1639-1645).
Figure 24:
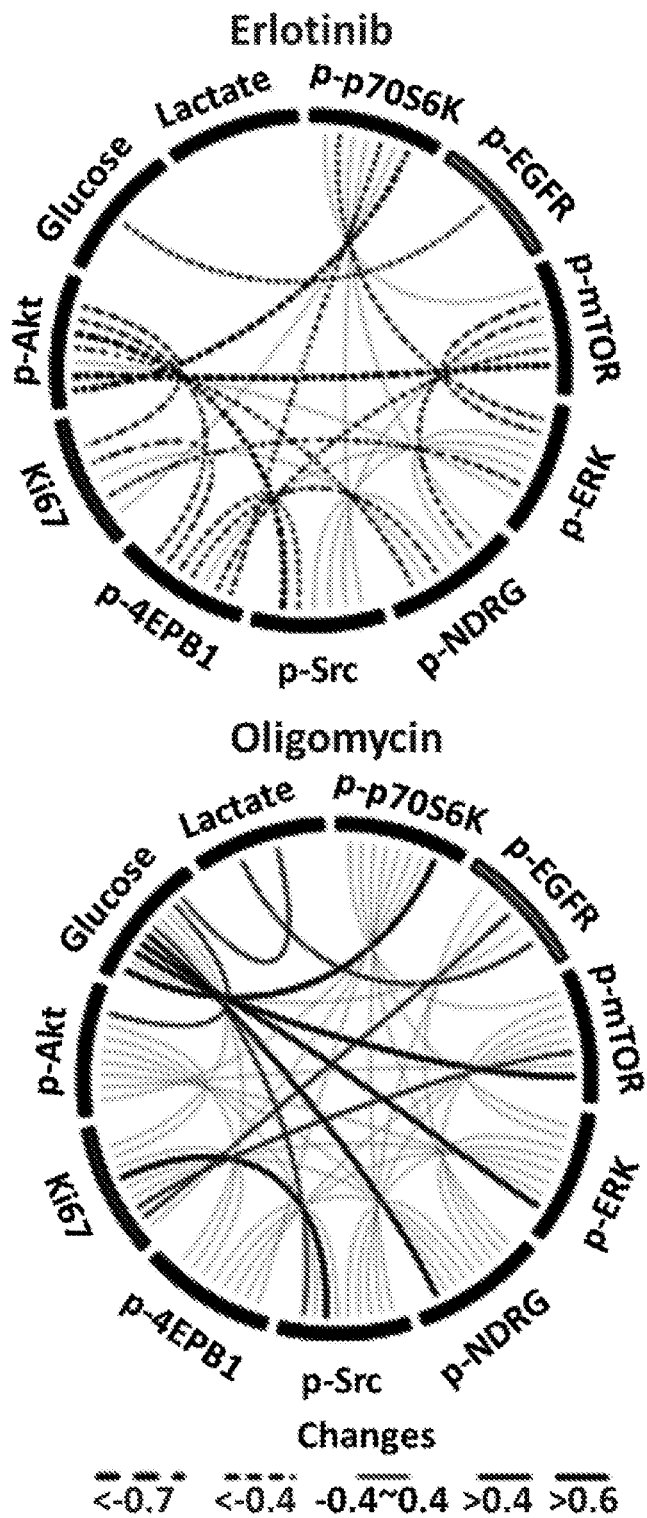
FIG. 24. Correlation networks highlighting the changes after drug treatments.
Figure 25:
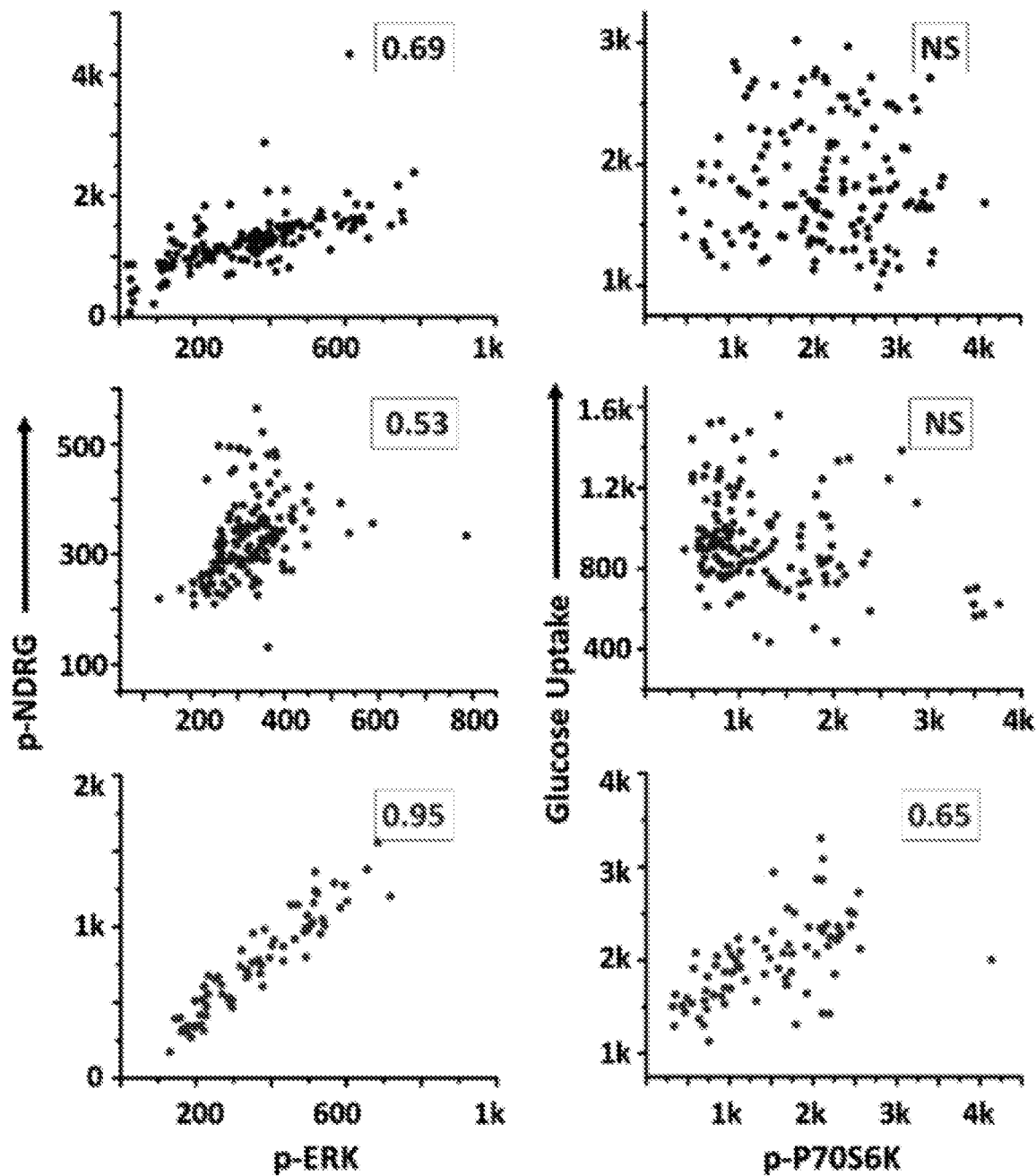
FIG. 25. Selected correlations in the GBM39 cells from control (upper, row), 1 μM erlotinib (middle row), and 0.1 μM oligomycin treated (lower row) samples. Statistically significant correlations between analytes are labeled in boxes. NS, not significant.
Figure 26:
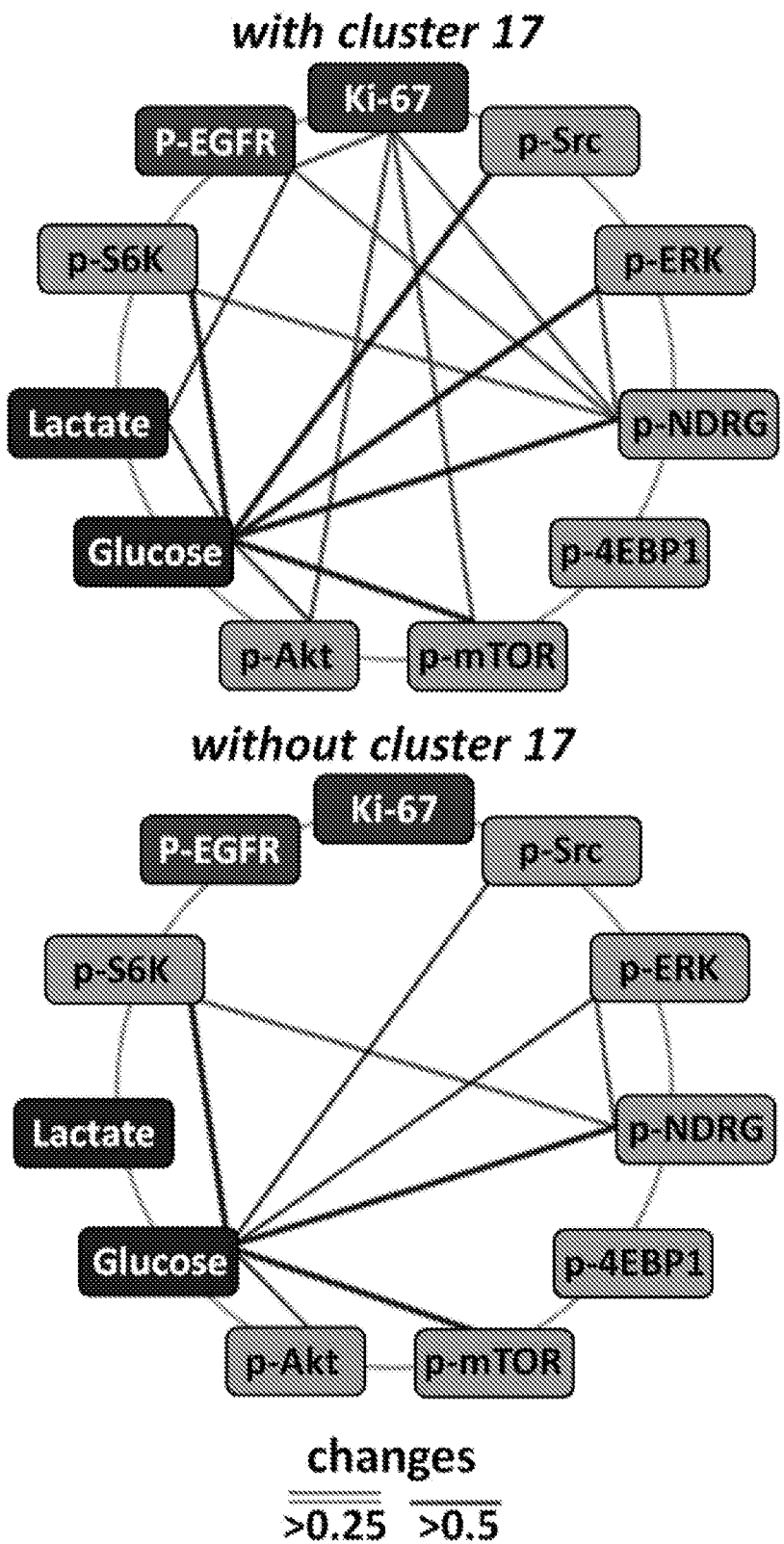
FIG. 26. Correlation changes following oligomycin treatment. Without Cluster 17, the increased correlations between p-EGFR and its downstream effectors, as well as between glucose/lactate and phosphoproteins are significantly dampened or even disappeared. The correlations between lactate and glucose, as well as between lactate and p-EGFR are also disappeared. This comparison confirms that the highest proliferative Cluster 17 cells are driving the observed oncogene addiction.

We also found that the most proliferative cells from each treatment group (Clusters 5, 11 and 17), marked by the elevated level of Ki67 (proliferation marker), exhibited rather unique metabolic and signaling signatures. In particular, in the control and erlotinib-treated cells, the proliferation ability did not correlate well with aerobic glycolysis nor the EGFR signaling activities (cluster 5 and 11). However, cluster 17 had the highest proliferation, lactate production and EGFR signaling activities within the oligomycin-treated sample group. Further analysis also revealed that oligomycin treatment led to strengthened correlations between aerobic glycolysis and oncogenic signaling, as well as within the phosphoprotein signaling network (FIGS. 23-25). These results indicated that by promoting the highly aerobic glycolytic phenotype, oligomycin also reinforced the cellular reliance on oncogenic EGFR signaling. In addition, cluster 17 was found to be the major contributors to this increased reliance (FIG. 26). Given time, these cells may dominate the entire cell population based on their relatively higher proliferation rate. On the other hand, the elevated oncogene addiction could render them more susceptible to EGFR inhibition.

Figure 27:
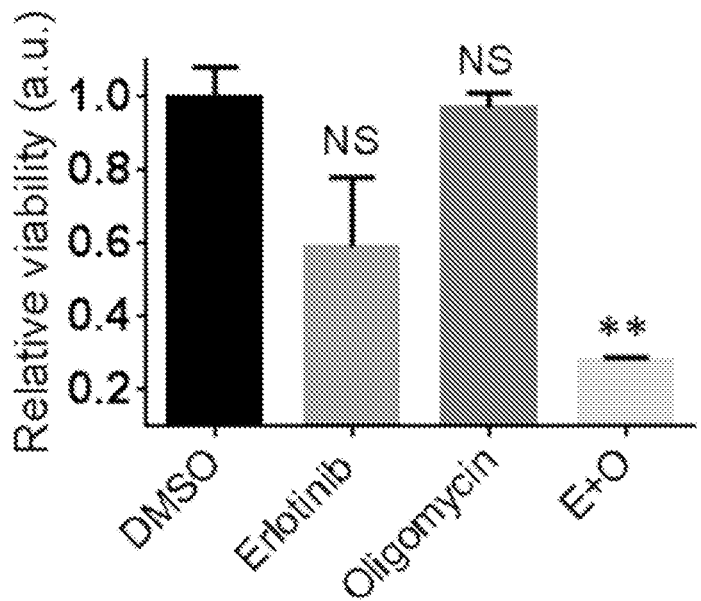
FIG. 27. Relative viability for monotherapies and the therapy combination evaluated by cell counting assay under the same treatment condition (erlotinib: 1 μM, oligomycin: 0.1 μM) used in the SCBC assay (cell number normalized to DMSO. Statistical significance is evaluated by Student's t-test; NS: not significant, **p<0.01). The synergy score from this test was calculated to be 13.6, which is very close to that from the resazurin assay.
Figure 28:
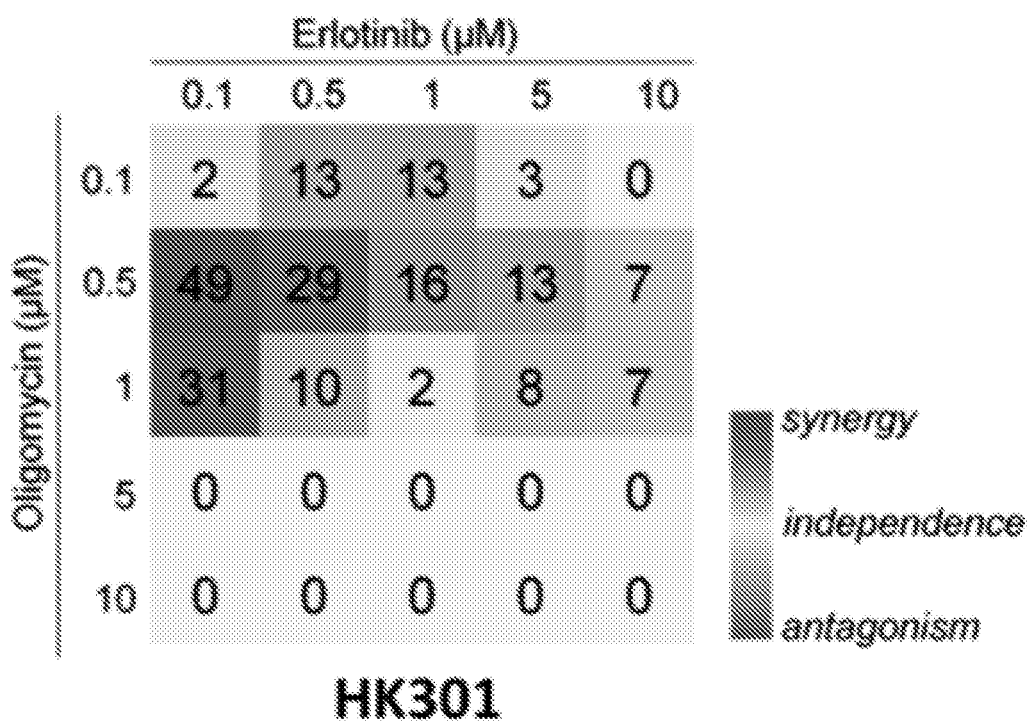
FIG. 28. Synergistic effects observed in erlotinib and oligomycin co-treatment experiments on HK301 cells FIG. 29. Synergistic effects observed in erlotinib-metformin and erlotinib-phenformin co-treated experiments on GBM39 cells.

Based on the observations above, we hypothesized that a combination of erlotinib and oligomycin would induce a synergistic growth inhibition on GBM39. Indeed, such synergistic effect across a broad dose range of erlotinib (1-10 µM) and oligomycin (0.1-1 µM) was observed (FIG. 4, panel c, FIG. 27). In order to test the generality of this result, we also performed the same tests on a second EGFRVIII mutant GBM cell line (HK301) that is more sensitive to erlotinib treatment. As expected, we observed similar synergistic effects, albeit starting at lower doses of erlotinib (FIG. 28).

Figure 29:
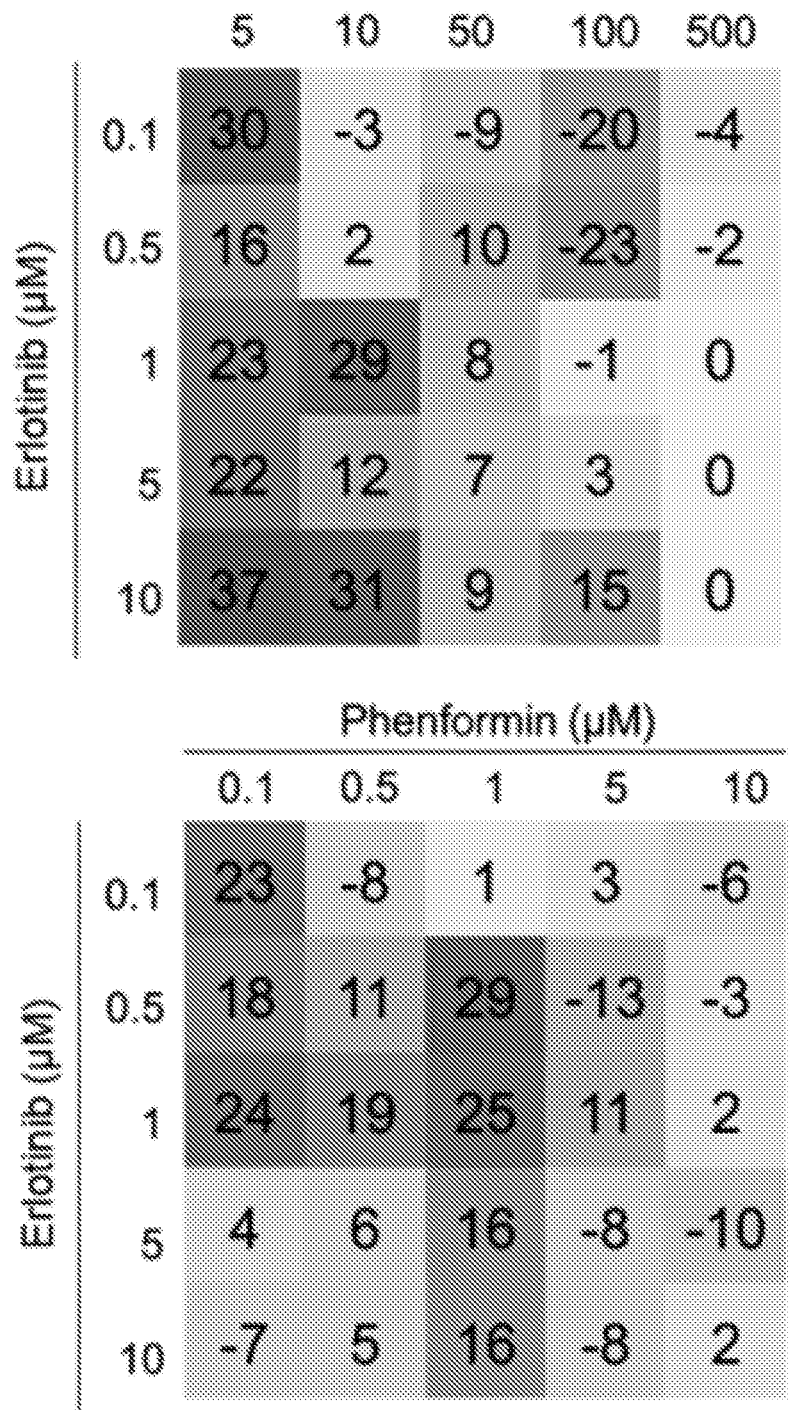
Figure 30:
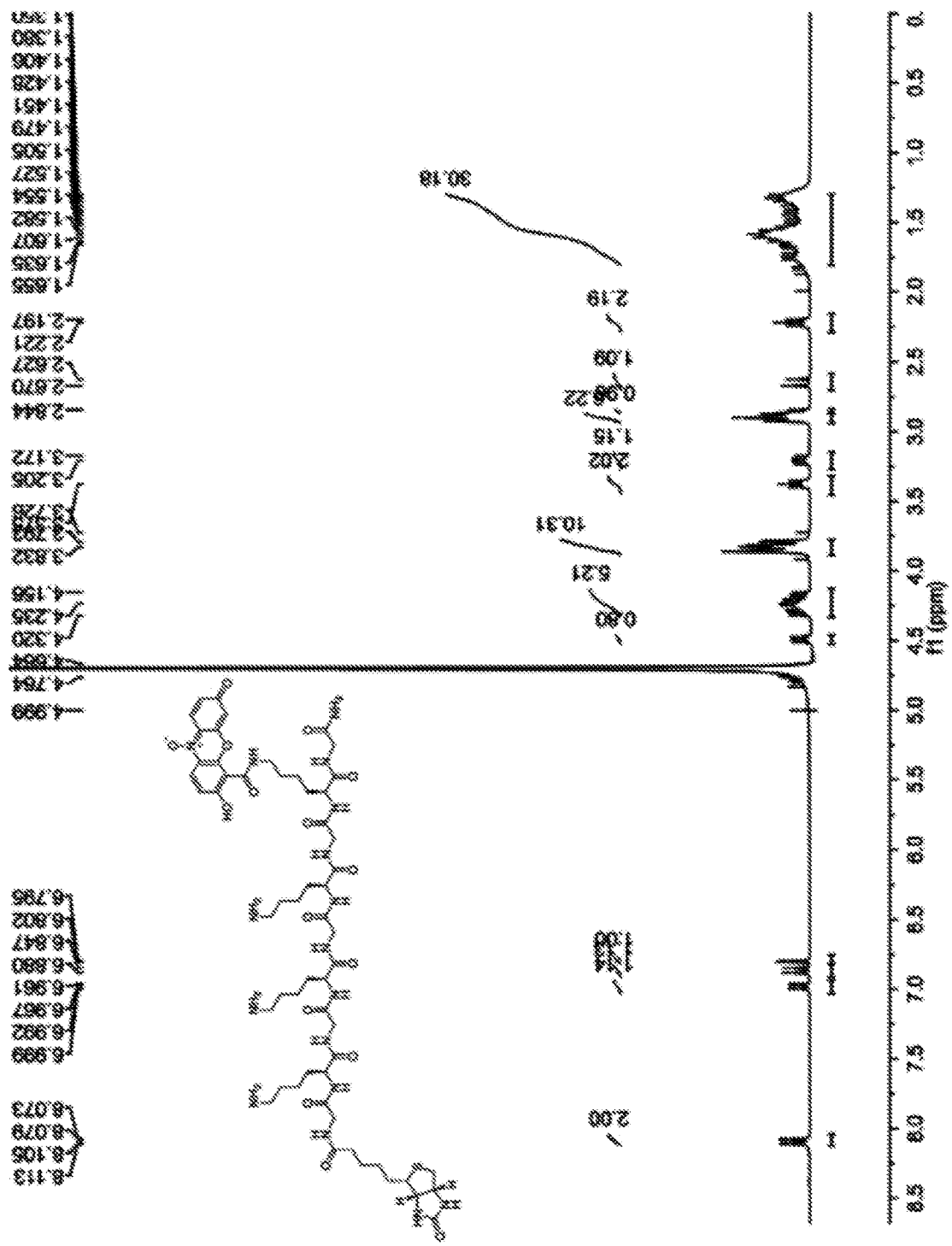
FIG. 30. $^1$H-NMR of Biotin-modified CRz (BRz) (300 MHz, $D_2O$), from the aromatic area expand spectrum, we can tell the product took the carboxyl-quinone type configuration.
Figure 31:
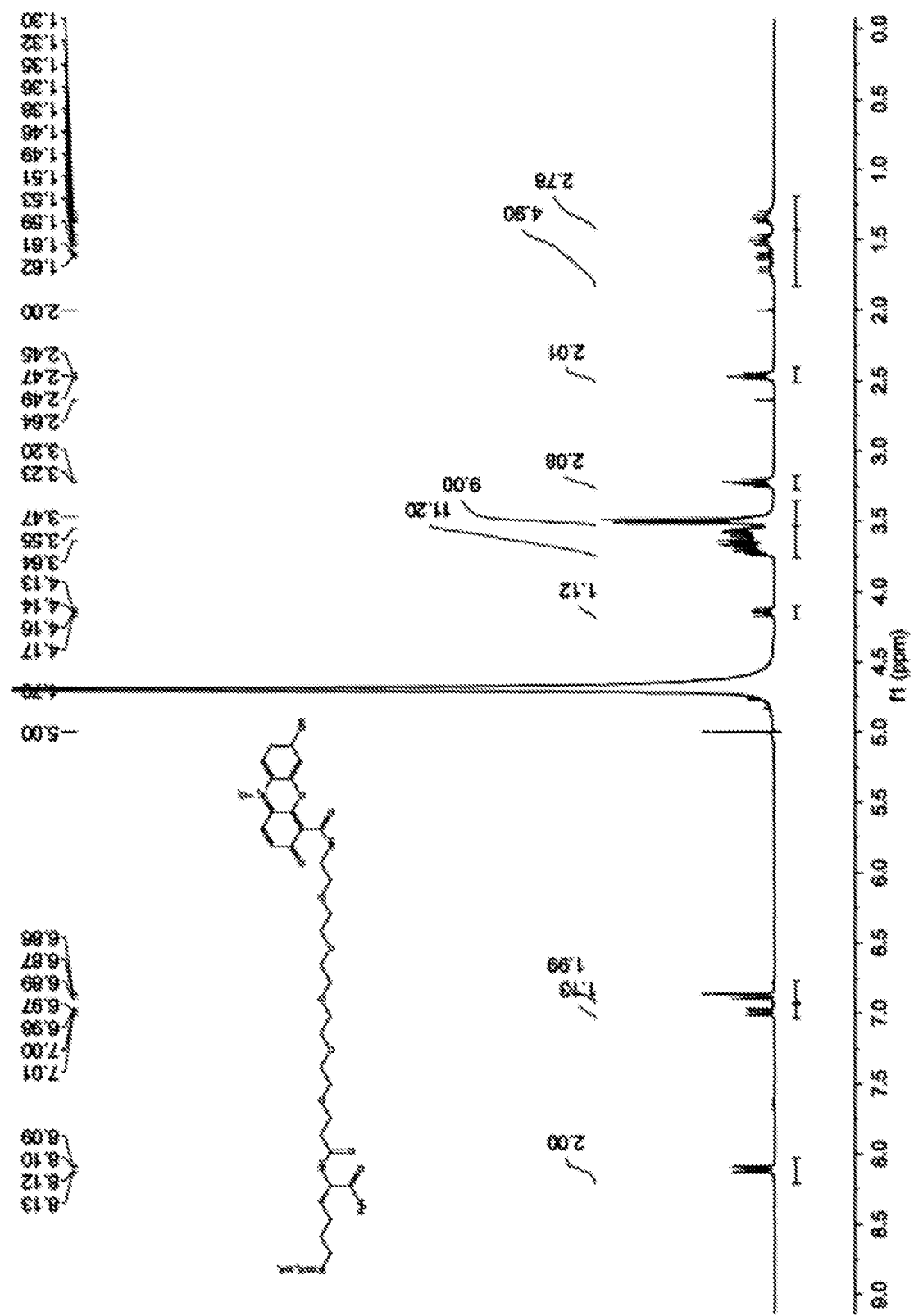
FIG. 31. $^1$H NMR spectra of APRz (300 MHz, $D_2O$).
Figure 32:
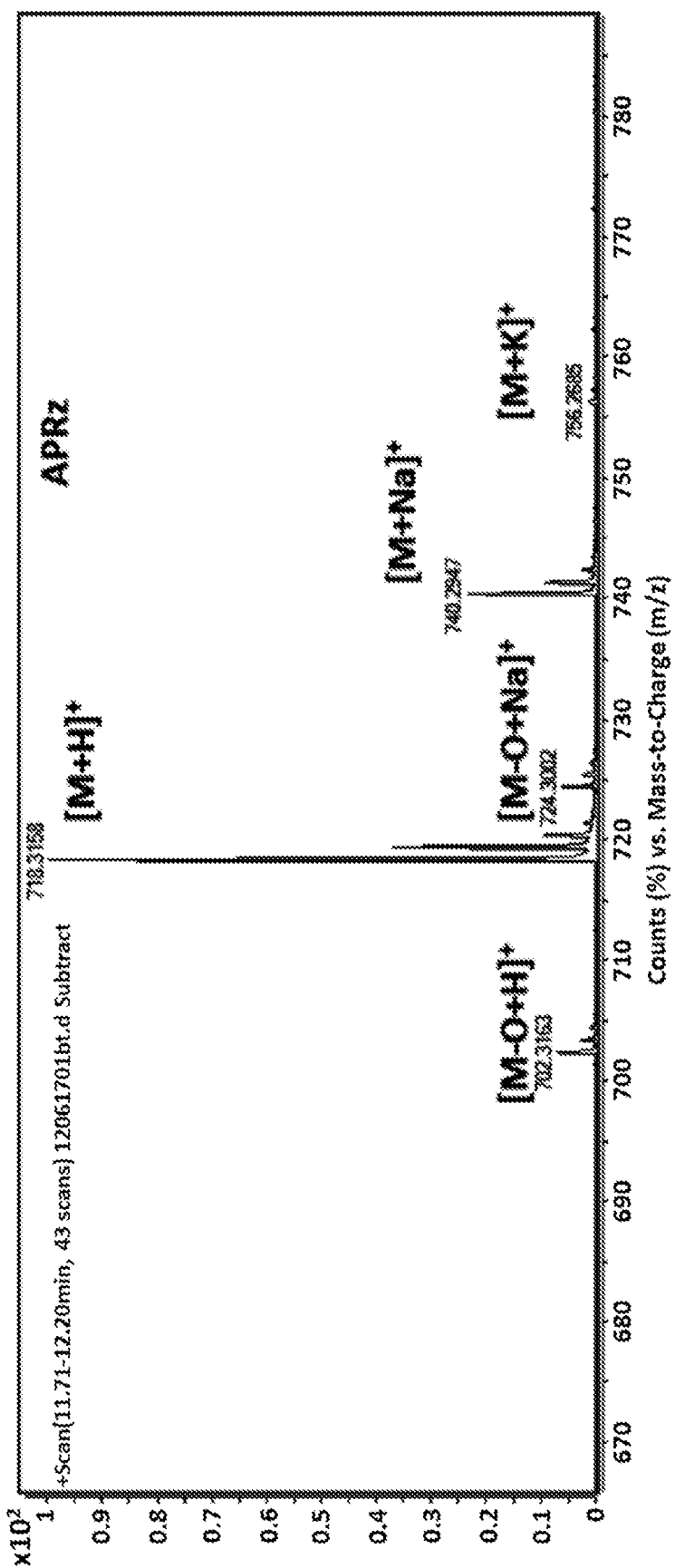
FIG. 32. Mass spectrum of APRz obtained through electrospray ionization (ESI). A fraction of the molecules were possibly reduced through ESI process.
Figure 33:
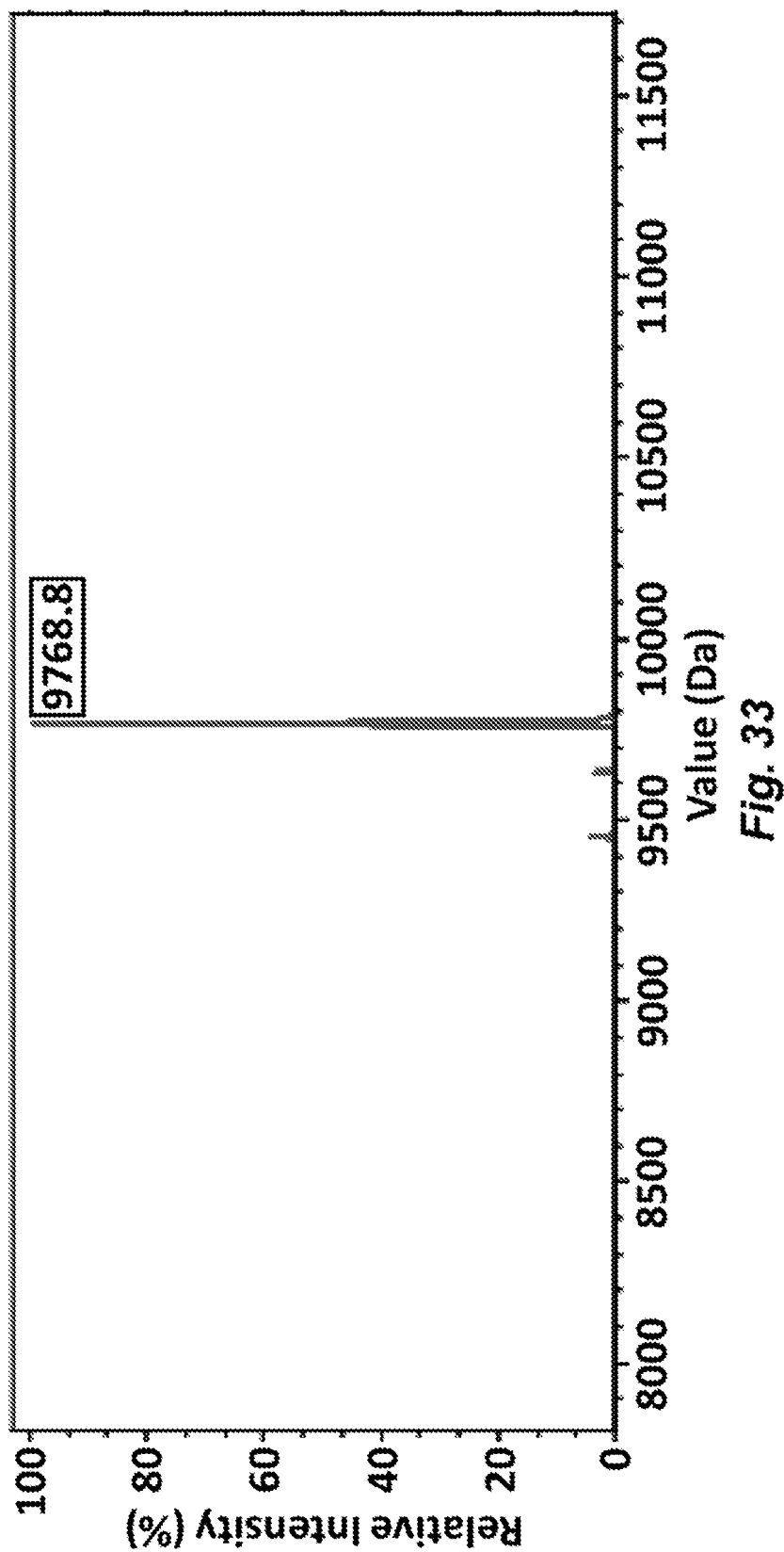
FIG. 33. The MALDI for DNA oligomer (modified with DBCO at 5'), calculated molecular weight 9769.7, molecular weight found 9768.8 [M–H]–.
Figure 34:
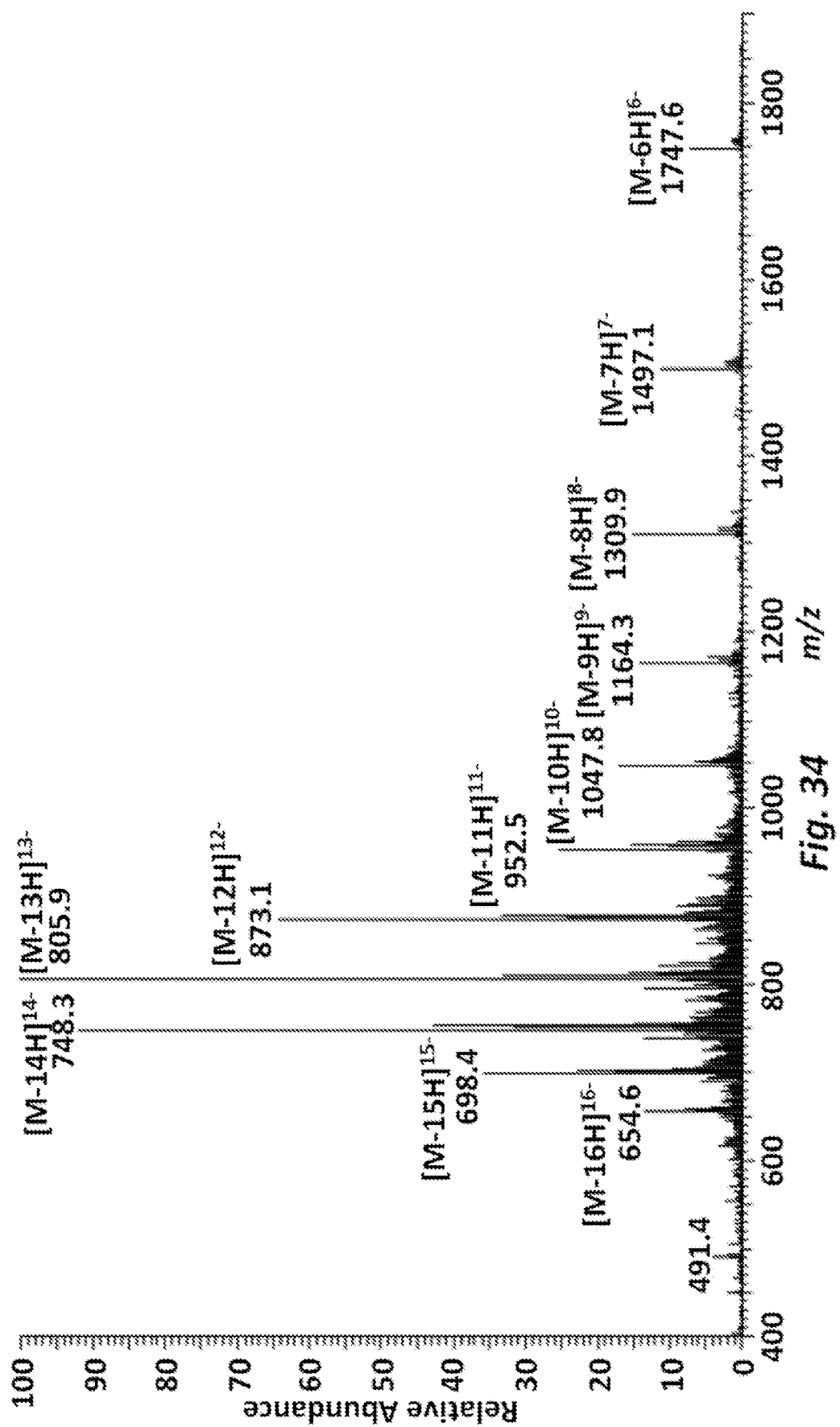
FIG. 34. ESI of APRz-DNA complex. Calculated molecular weight 10487.0 and 1746.8 $[M-6H]^{6-}$, molecular weight Found 1747.6 $[M-6H]^{6-}$.
Figure 35:
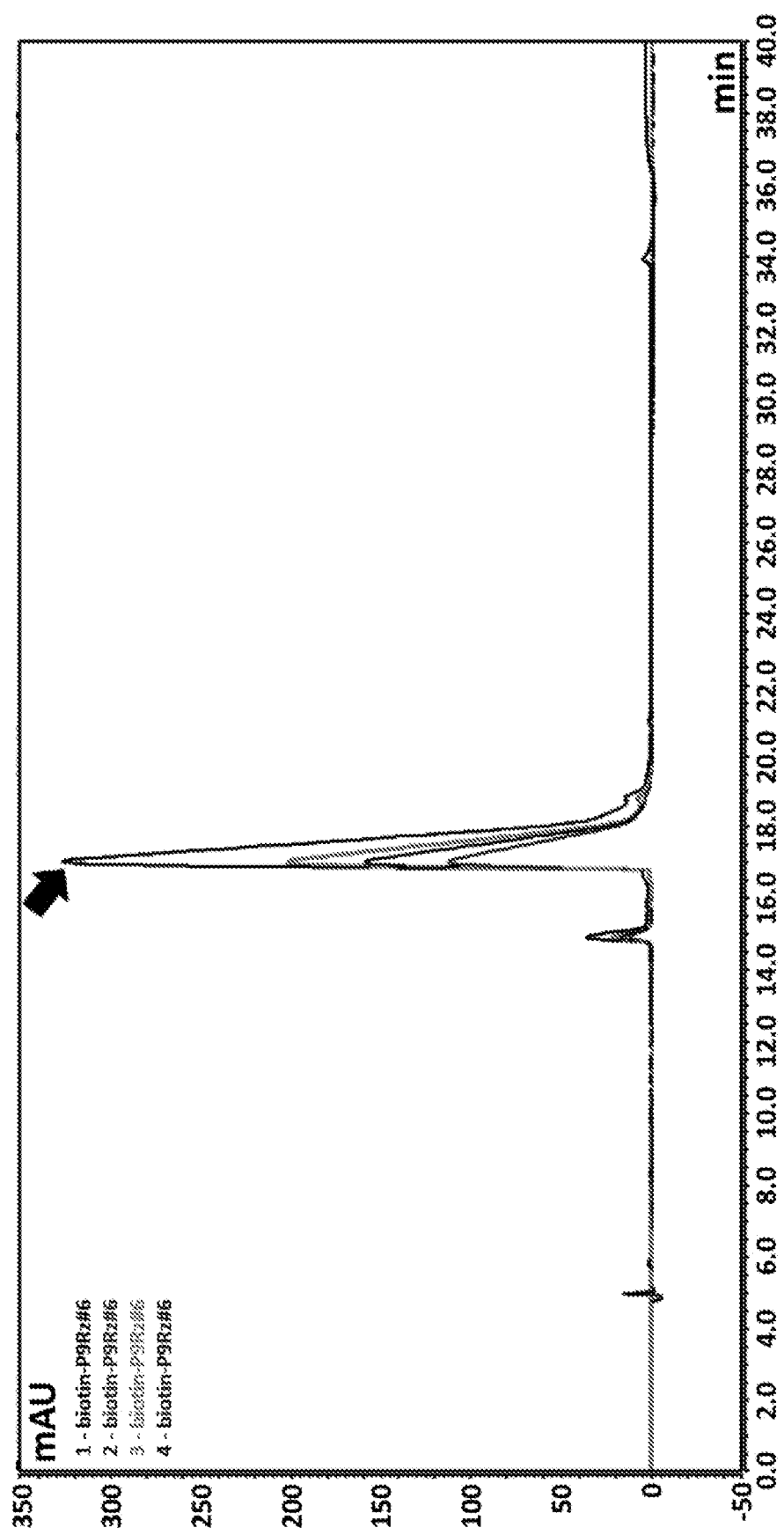
FIG. 35. HPLC of CRz (BRz), arrow shows the target peak.
Figure 36:
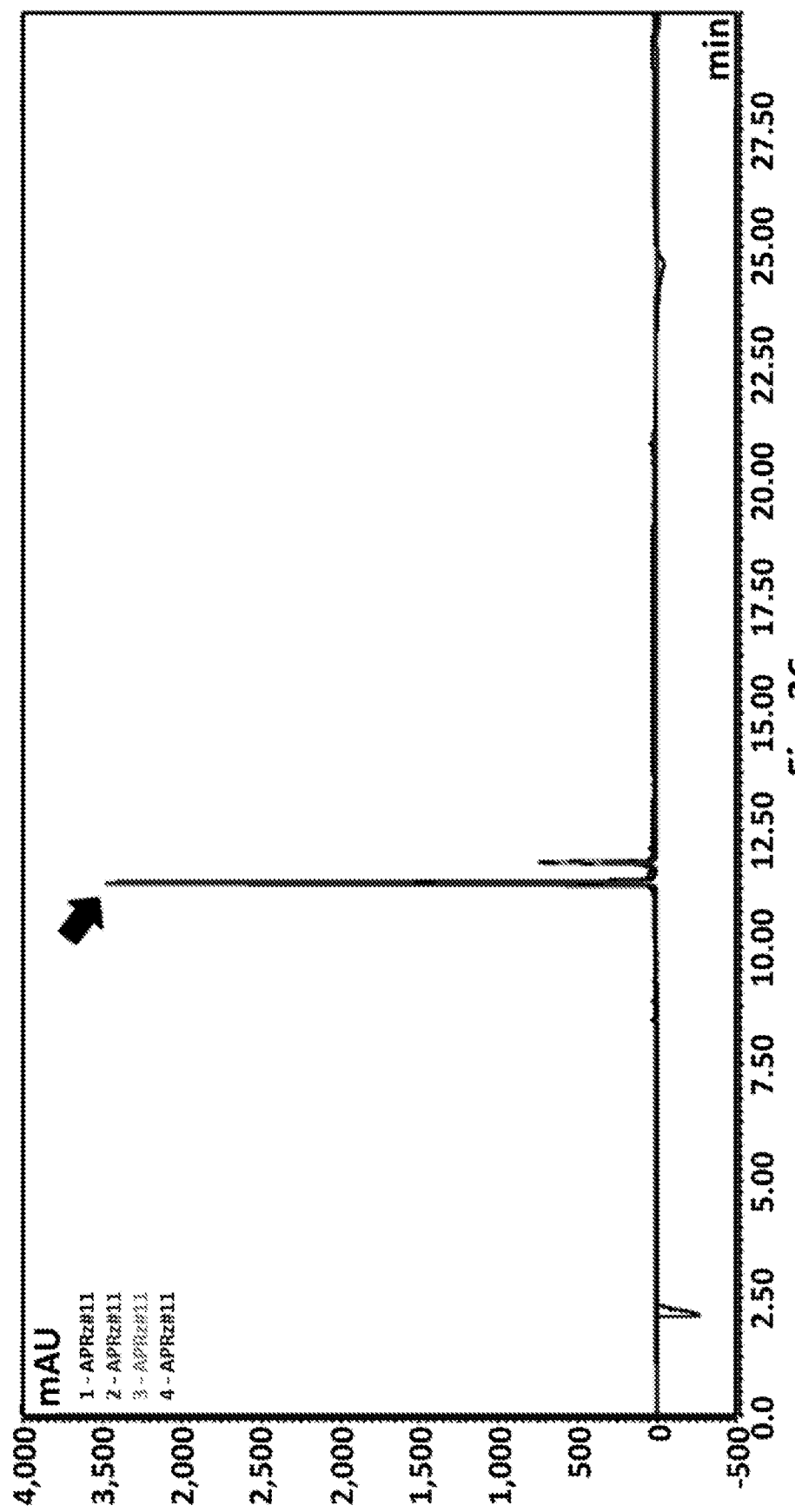
FIG. 36. HPLC of APRz, arrow shows the target peak.

We then sought to test if the effect of oligomycin can be extended to other clinically relevant respiration inhibitors. We studied the therapeutic outcome of combining erlotinib with metformin or phenformin on GBM39 cells. The latter two drugs are approved for treating type-II diabetes and their reaction mechanisms are similar to that of oligomycin. Again, we observed significant synergistic effects (FIG. 29).

The described chemical approach for lactate quantification is complementary to our previously reported glucose uptake assay and enables comprehensive and true aerobic glycolysis profiling in single cells. When combined with the multiplex phosphoproteomic assays in the SCBC platform, it permits a clarifying view into how glycolytic activities relate to phosphoprotein signaling. In addition, the surface immobilized fluorescence probes may be adapted to detect other redox-active metabolites, through employing different enzymatic schemes.

Supplemental Materials.

TABLE 1

List of capture antibodies used in this work.

| Capture Antibody Name | Manufacture |
|---|---|
| Anti-streptavidin | Abcam, ab10020 |
| Phospho-p70 S6 Kinase (T389) DuoSet | R&D Systems, DYC896 |
| Human EGFR Antibody, Goat Polyclonal | R&D Systems, AF231 |
| Human Total p53 DuoSet | R&D Systems, DYC1043 |
| Human Phospho-TOR (S2448) DuoSet | R&D Systems, DYC1665 |
| Human/Mouse/Rat Phospho-ERK1 (T202/Y204) DuoSet | R&D Systems, DYC1825 |
| Human NDRG1, Goat Polyclonal | R&D Systems, AF5209 |
| Human Phospho-Src (Y419) DuoSet | R&D Systems, DYC2685 |
| Human Phospho-Src (Y419) DuoSet | R&D Systems, AF3227 |
| Human/Mouse Phospho-Akt1 (S473) DuoSet | R&D Systems, DYC2289C |
| Human Ki-67/MKI67, Sheep Polyclonal | R&D Systems, AF7617 |

TABLE 2

List of detection antibodies used in this work.

| Detection Antibody Name | Manufacture |
|---|---|
| Phospho-p70 S6 Kinase (T389) DuoSet | R&D Systems, DYC896 |
| Human Total p53 DuoSet | R&D Systems, DYC1043 |
| Human Phospho-TOR (S2448) DuoSet | R&D Systems, DYC1665 |
| Human/Mouse/Rat Phospho-ERK1 (T202/Y204) DuoSet | R&D Systems, DYC1825 |
| Human Phospho-Src (Y419) DuoSet | R&D Systems, DYC2685 |
| Human/Mouse Phospho-Akt1 (S473) DuoSet | R&D Systems, DYC2289 |
| Phospho-EGF Receptor (Tyr1173) Antibody, Rabbit Mono-clonal | Cell Signaling, 4407S |

Key Chemicals and Reagents (2-(1H-benzotriazol-1-yl)-1,1,3,3-tetramethyluronium hexafluorophosphate (HBTU, 99.6%) and Fmoc-Lys ($N_3$)—OH (99.3%) were obtained from Chem-Impex (Wood Dale, IL). Rink amide MBHA resin (0.678 mmol/g) was purchased from Aapptec (Louisville, KY). Fmoc-PEG5-OH (98.68%) was obtained from BroadPharm (San Diego, CA). Diisopropylethylamine (DIEA, 99.5%) was obtained from ACROS (Germany) and piperidine (99%) was purchased from Alfa Aesar (Ward Hill, MA). Trifluoroacetic acid (TFA, 99%) was obtained from Oakwood Chemical (Estill, SC) and $D_2O$ (99.9%) was purchased from Cambridge Isotope Laboratories. Inc. (Andover, MA). Beta-nicotinamide adenine dinucleotide disodium salt hydrate reduced form (NADH, Disodium Salt, 99.2%) was obtained from Calbiochem (Germany). Sodium-L-lactate (99%) was obtained from Sigma-Aldrich (Switzerland). G'-DBCO (94.9%) was ordered from IDT (Coralville, IA). Beta-nicotinamide adenine dinucleotide sodium salt (NAD+, 95%) and L-lactic dehydrogenase from rabbit muscle (LDH, 800-1200 units/mg protein) was obtained from Sigma-Aldrich (Saint Louis, MO). Diaphorase was obtained from Innovative Research, Inc. (Novi, MI). Bovine serum albumin (BSA), N,N-Dimethylformamide (DMF, 99.9%) and Acetonitrile (99.95%) was obtained from Fisher Scientific (Fair Lawn, NJ). Sodium phosphate dibasic anhydrous (Na2HPO4, 99.6%) and Sodium phosphate monobasic monohydrate (NaH2PO4, 99.4%) were purchased from Fisher (China). Sodium Chloride (NaCl) and TWEEN™ 20 were purchased from Fisher (USA). 4-carboxylresazurin was synthesized following literature procedures (Xie et al. PCT Publication No: WO 2011/038241).

Conjugation of CRz to Poly-Lysine and Immobilization to the Surface

50 µL of CRz solution (100 µM in pH 6 MES buffer) was mixed with 25 µL of EDC solution (200 µM in pH 6 MES buffer) and 30 µL of N-hydroxysuccinimide solution (200 µM in pH 6 MES buffer). The mixture was incubated at room temperature for 15 min. Subsequently, 10 µL of poly-lysine solution (1 mg/mL in pH 7 PBS buffer) was added to the solution. The mixture was incubated at room temperature for 24 hours. The crude mixture was purified by reverse phase HPLC followed by lyophilization.

In order to immobilize the polymer to the surface, the afforded CRz-modified poly-lysine was reconstituted in water at 1 mg/mL and flown through the glass surface in a PDMS microchannel for 5 hrs and dried in air overnight.

Synthesis of Amine-Modified CRz

Figure 6:
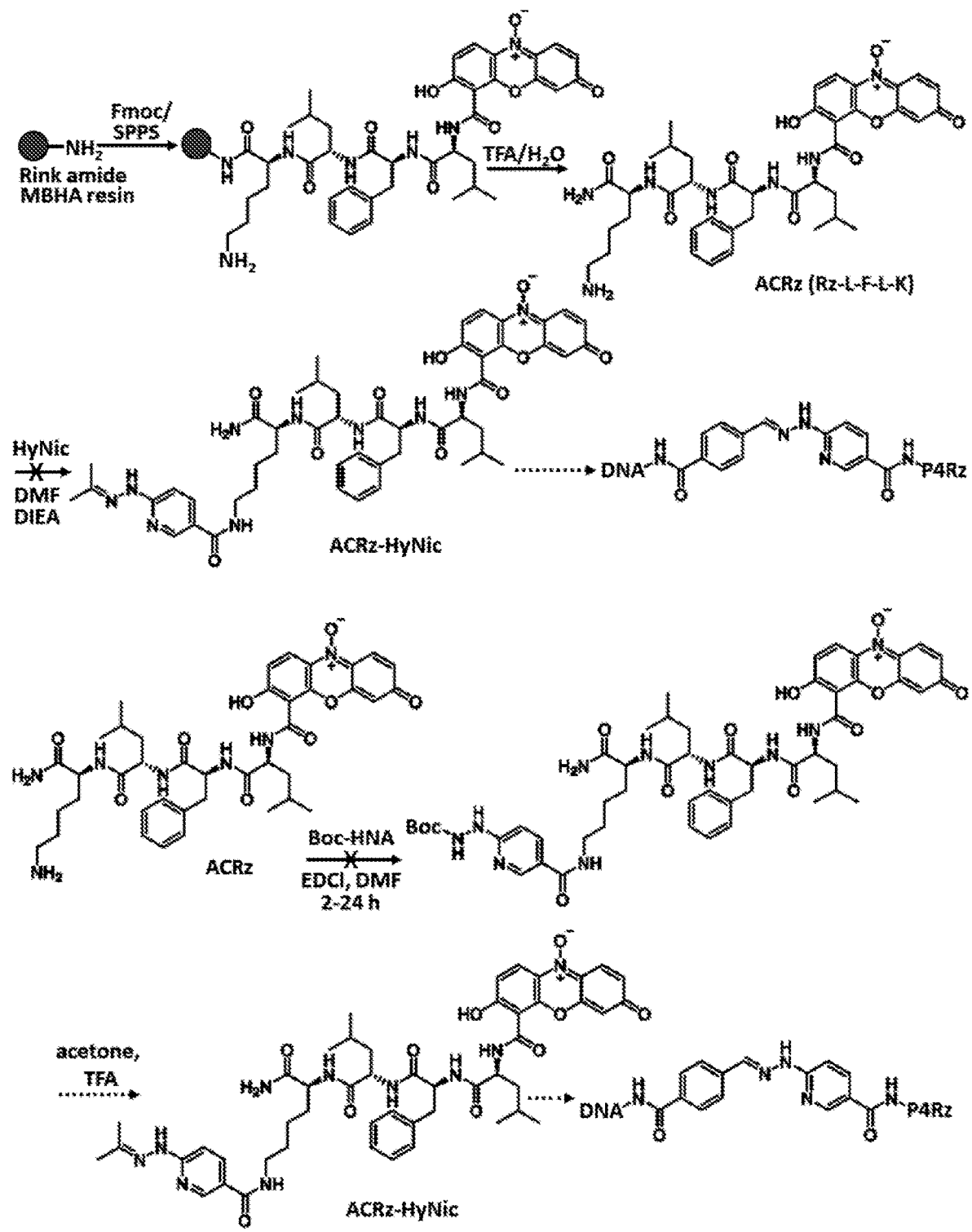
FIG. 6. Synthesis of the peptide-modified CRz bearing an aliphatic amine group (ACRz). Subsequent conversion to protected hydrazine was unsuccessful, due to the lability of the N-oxide group. Changing hydrazine protection group did not improve the yield.

The amine-modified CRz (ACRz) was synthesized on Rink-MBHA resin (200 mg, loading capacity 0.678 mmol/g) following standard solid-phase peptide synthesis protocols. The synthetic scheme is shown in FIG. 6. For Fmoc deprotection, the resin was agitated with piperidine (5 mL, 20% v/v in DMF, 3×5 min) and washed with DMF (5×5 mL). For amino acid coupling, a solution of Fmoc-amino acid (0.68 mmol, in 3 mL of DMF), HBTU (3.2 mL of 0.2 M in DMF) and DIEA (0.28 mL) was added to the resin and agitated at room temperature for 1 h, followed by DMF washes (5×5 mL). To cleave the peptide from the resin, a mixture of TFA and water (95:5 v/v, 10 mL) was added to the resin. After 2 h, the solution was filtered, and the resin was washed with TFA (3×5 mL). The combined cleavage solution was concentrated in vacuo to give the crude product, which was further purified by reverse-phase HPLC. ESI-TOF, $C_{40}H_{51}N_7O_9$, $[M+H]^+$ calcd 774.38, found 774.35.

Synthesis of Carboxy-Modified CRz (CPRz)

Figure 7:
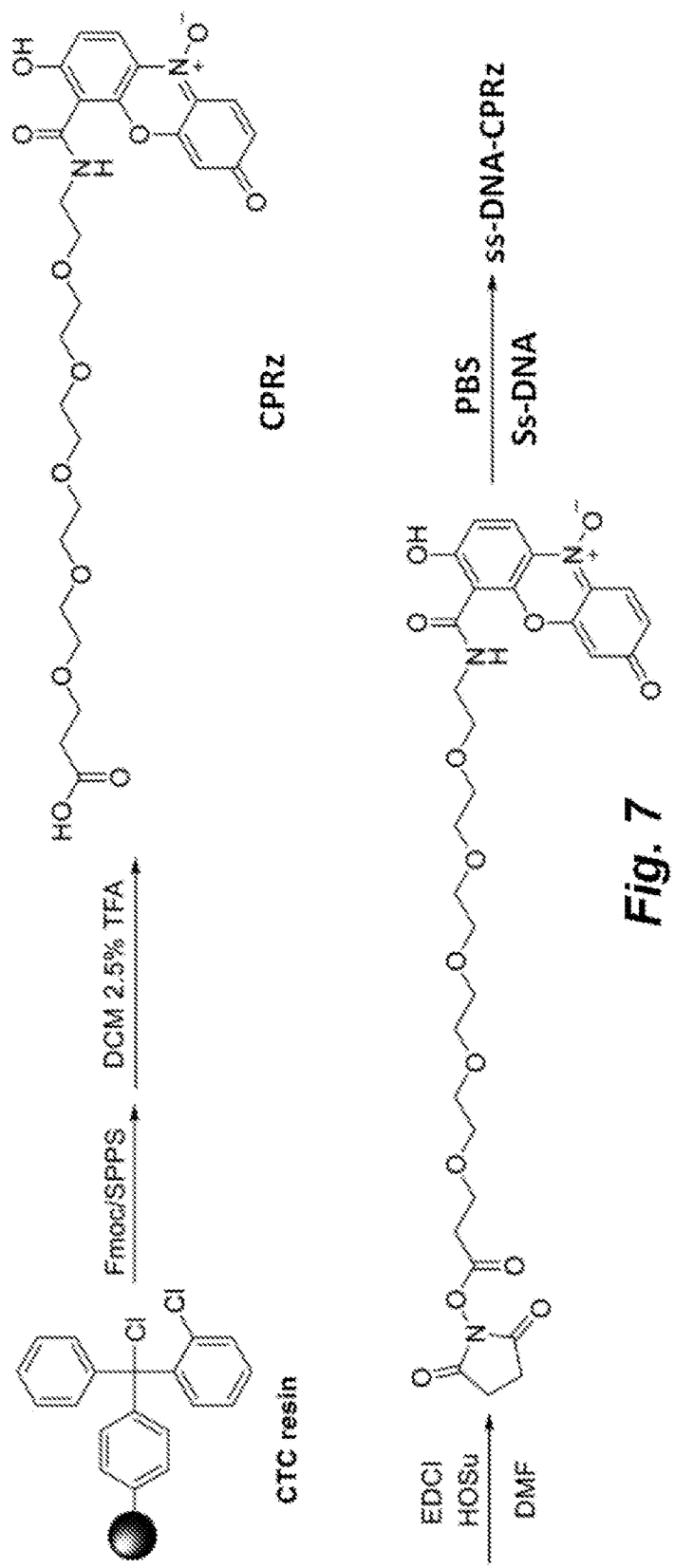
FIG. 7. Synthesis of the extended CRz bearing an aliphatic carboxyl group (CPRz). This carboxyl group could be readily converted to an NHS ester using standard coupling procedures. However, the ss-DNA-CPRz was not stable, and went through spontaneous self-reduction even at −20° C.

The Carboxy-modified CRz (CPRz) was synthesized on CTC resin (200 mg, loading capacity 0.4 mmol/g) following standard solid-phase peptide synthesis protocols. The synthetic scheme is shown in FIG. 7. For the first amino acid coupling, the resin was agitated with the Fmoc-NH-PEG5-COOH (0.24 mmol) and DIEA (0.28 mL) in dry DCM (2 mL) for 1 h, and MeOH (0.2 mL) was added to end-cap the resin. For Fmoc deprotection, the resin was agitated with piperidine (5 mL, 20% v/v in DMF, 3× 5 min) and washed with DMF (5× 5 mL). For amino acid coupling, a solution of Fmoc-amino acid (0.68 mmol, in 3 mL of DMF), HBTU (3.2 mL of 0.2 M in DMF) and DIEA (0.28 mL) was added to the resin and agitated at room temperature for 1 h, followed by DMF washes (5×5 mL). To cleave the peptide from the resin, a mixture of TFA and DCM (5:95 v/v, 10 mL) was added to the resin. After 2 h, the solution was filtered, and the resin was washed with TFA (3×5 mL). The combined cleavage solution was concentrated in vacuo to give the crude product, which was further purified by reverse-phase HPLC. ESI-TOF, $C_{26}H_{32}N_2O_{12}$, $[M+Na]^+$ calcd 587.19, found 587.16.

Synthesis of Biotin-CRz (BRz)

The BRz sequence was synthesized on Rink Amide MBHA resin (200 mg, loading capacity 0.678 mmol/g) following standard solid-phase peptide synthesis protocols. The synthetic scheme is shown in FIG. 8. For Fmoc deprotection, the resin was agitated with piperidine (5 mL, 20% v/v in DMF, 3×5 min) and washed with DMF (5×5 mL). For amino acid coupling, a solution of Fmoc-amino acid (0.68 mmol, in 3 mL of DMF), HBTU (3.2 mL of 0.2 M in DMF) and DIEA (0.28 mL) was added to the resin and agitated at room temperature for 1 h, followed by DMF washes (5×5 mL). To cleave the peptide from the resin, a mixture of TFA and water (95:5 v/v, 10 mL) was added to the resin. After 2 h, the solution was filtered and the resin was washed with TFA (3×5 mL). The combined cleavage solution was concentrated in vacuo to give the crude product, which was further purified by reverse-phase HPLC, yield 27.8% (by HPLC). MALDI-TOF, $C57H85N17O16S$, $[M+H]^+$ calcd 1296.62, found 1296.70. $^1H$ NMR (300 MHz, $D_2O$) δ 8.10 (d, J=10.1 Hz, 1H), 8.09 (d, J=9.3 Hz, 1H), 6.98 (dd, J=9.4, 2.0 Hz, 1H), 6.86 (d, J=10.0 Hz, 1H), 6.80 (d, J=2.1 Hz, 1H), 4.49 (dd, J=7.9, 4.9 Hz, 1H), 4.33-4.13 (m, 5H), 3.89-3.77 (m, 10H), 3.37 (t, J=6.4 Hz, 2H), 3.27-3.14 (m, 1H), 2.90 (t, J=7.5 Hz, 6H), 2.85 (m, 1H), 2.65 (d, J=13.0 Hz, 1H), 2.22 (t, J=7.3 Hz, 2H), 1.81-1.29 (m, 30H).

Synthesis of APRz

Figure 9:
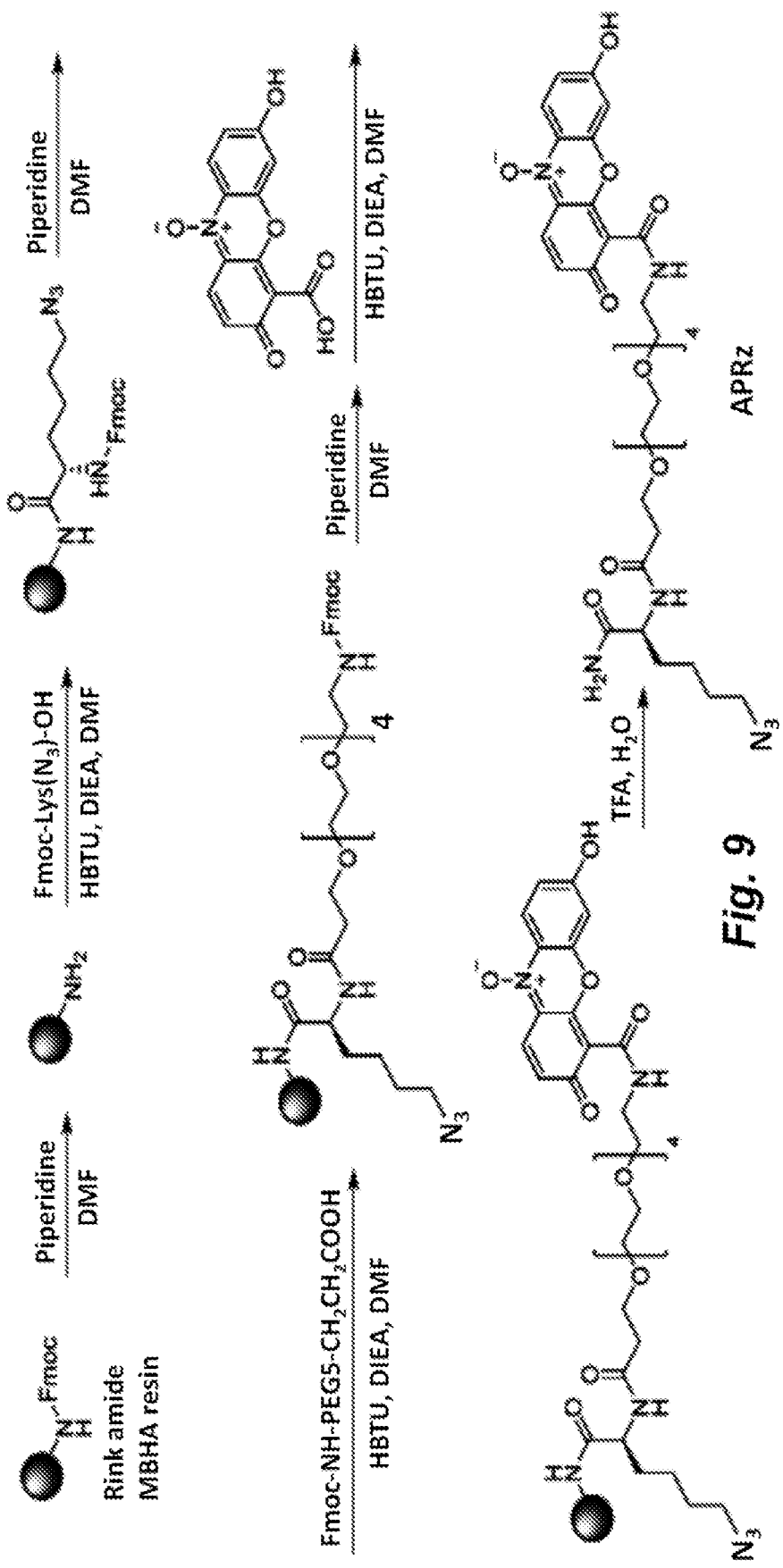
FIG. 9. Synthesis of azide-modified CRz (APRz).

The APRz sequence was synthesized on Rink Amide MBHA resin (200 mg, loading capacity 0.678 mmol/g) following standard solid-phase peptide synthesis protocols. The synthetic scheme is shown in FIG. 9. For Fmoc deprotection, the resin was agitated with piperidine (5 mL, 20% v/v in DMF, 3×5 min) and washed with DMF (5×5 mL). For amino acid coupling, a solution of Fmoc-amino acid (0.68 mmol, in 3 mL of DMF), HBTU (3.2 mL of 0.2 M in DMF) and DIEA (0.28 mL) was added to the resin and agitated at room temperature for 1 h, followed by DMF washes (5×5 mL). To cleave the peptide from the resin, a mixture of TFA and water (95:5 v/v, 10 mL) was added to the resin. After 2 h, the solution was filtered and the resin was washed with TFA (3×5 mL). The combined cleavage solution was concentrated in vacuo to give the crude product, which was further purified by reverse-phase HPLC, yield 32.2% (by HPLC). ESI-TOF, $C32H43N7O12$, $[M+Na]^+$ calcd 740.29, found 740.31. $^1H$ NMR (300 MHZ, $D_2O$) δ 8.12 (d, J=9.9 Hz, 1H), 8.11 (d, J=9.5 Hz, 1H), 6.99 (dd, J=9.5, 2.4 Hz, 1H), 6.88 (d, J=9.9 Hz, 1H), 6.87 (d, J=2.4 Hz, 1H), 4.15 (dd, J=9.2, 5.1 Hz, 1H), 3.75-3.53 (m, 11H), 3.53-3.35 (m, 9H), 3.23 (t, J=6.7 Hz, 2H), 2.47 (t, J=6.0 Hz, 2H), 1.83-1.43 (m, 5H), 1.42-1.19 (m, 3H).

DNA-APRz Conjugate

60 μL of APRz solution (100 μM in 1% BSA/PBST) was mixed with 0.6 μL of DNA-DBCO solution (100 μM in PBS) and the mixture was incubated at room temperature for one hour. After incubation, the mixture was diluted to 600 μL and used without further purification. The excess amount of APRz ensures high yield of DNA-APRz. Unreacted APRz can be easily removed after DNA hybridization.

Generation of the Solution Phase Working Curve

107 μL of NAD solution (1 mM in PBS) is mixed with 100 μL of APRz solution (20 μM in PBS), 1 μL of diaphorase (1 kU/mL in PBS) and 2 μL of LDH (1 kU/mL in $(NH_4)_2SO_4$) and added into a 96-well plate. 40 μL of lactate solutions (various concentrations in PBS) are then added to the mixture and incubated for one hour. The fluorescence intensity is then measured by a microplate reader (excitation 540 nm, emission 590 nm). Experiment was carried out in quadruplets to determine the error range.

Generation of the Surface-Based Working Curve

A 16-well PDMS slab was placed onto a microscope glass slide, on which single strand DNA oligomers are patterned in 20 μm stripes. The volume of each well is 50 μL and it is equipped with at least eight sets of DNA barcode strips. 50 μL of 1% BSA/PBST was added to each well and the device was incubated at room temperature for one hour to block the surface. Afterwards, the solutions were removed and each well was washed with PBST for three times. 45 μL of the DNA-APRz conjugate solution was added into each well and incubated at 37° C. for one hour.

Subsequently, each well was washed with PBST for three times. At this stage, the APRz probe was immobilized to the surface and ready to use.

To obtain the standard curve for lactate quantification, 20 μL of NAD+ solution (1 mM in PBST), 1 μL of LDH solution (1 kU in ammonium sulfate buffer), 1 μL of diaphorase solution (1 kU/mL in PBS) and 20 μL of lactate solution (various concentrations in PBST) was added to each well and the device was incubated at room temperature for one hour. The solutions were then removed and the device was washed with 1% BSA/PBST for three times, followed by three times of PBST. The PDMS slab was then removed and the glass slide was washed in PBS, 50% PBS/water and water and then spin-dried. The surface fluorescence intensity was then measured by a microscanner. Each data point was collected in quadruplets to obtain the error bar.

Cell Culture

GBM 39 primary neurospheres were provided by Prof. C. David James (UCSF, San Francisco, U.S.A.) and HK301 cells were provided by Prof. Harley Kornblum (UCLA, Los Angeles, U.S.A). Cells were cultured in Dulbecco's Modified Eagle Media Nutrient Mix F-12 (DMEM/F12, Thermo) supplemented with B27 (Invitrogen), Glutamax (Thermo), heparin (1 μg/mL, Sigma), Epidermal Growth Factor (EGF, 20 μg/mL, Sigma), Fibroblast Growth Factor (FGF, 20 ng/mL, Sigma) and 100 U/mL of penicillin and streptomycin (Thermo) in a humidified 5% $CO_2$ (v/v) incubator at 37° C. For drug treatments, 500K cells were suspended in 10 mL of media and was cultured for 24 h. Then, the medium was changed to 10 mL of fresh one containing 1 μM of erlotinib (ChemieTek) or 100 nM of oligomycin A (Sigma). For the erlotinib group, the GBM 39 cells were treated for 24 h while for the oligomycin group, the cells were treated for 3 h. Afterwards, the treated cells were processed for tests.

ECAR/OCR Measurements

The glycolysis stress test and mitochondrial stress test was measured with the Seahorse XFe24 Analyzer. Briefly, GBM39 cells were dissociated to single cell suspensions in XF base medium or XF base medium with 10 mM glucose for measuring the glycolysis stress test or the mitochondrial stress test, respectively. Cells were plated at $1\times10^5$ cells/well and adhered to a Seahorse XF24 cell culture microplate using Corning Cell-Tak. Plates were analyzed on the XFe24 Analyzer after a 30 min incubation for equilibration. Assay conditions of the glycolysis stress test included injections of 10 mM glucose, 1 μM oligomycin and 100 mM 2-DG. Assay conditions of the mitochondrial stress test included injections of 1 μM oligomycin, 0.75 μM FCCP, and 1 μM of Rotenone and antimycin A. After the assay, plated cells were lysed and protein concentrations were measured. Measurements were normalized to total protein in each well.

NOVA Measurements

Glucose consumption and lactate production were measured with a Nova Biomedical BioProfile Basic Analyzer. Briefly, cells were dissociated to single cell suspensions in DMEM/F12 with B27, penicillin-streptomycin, and GlutaMAX supplemented with heparin (5 μg/mL), EGF (50 ng/ml), and FGF (20 ng/ml). Cells were plated at $2\times10^6$ cell/well in 2 mL and incubated with specified drug treatment. 24 h after drug treatment, 1 mL supernatant was collected and analyzed in the Nova BioProfile Analyzer. Measurements were normalized to cell number.

Single Cell Suspension Preparation

GBM 39 neurospheres were collected via centrifugation at 500 g for 5 min and the media was removed. The collected cell pellet was then treated with 0.05% Tripsin/EDTA (Life Technologies) for 5 min at 37° C. and the original media was added back to the pellet. The suspension was then centrifuged again and the supernatant was discarded. The cells are now disassociated as single cells and ready for tests.

For SCBC measurements, the as-prepared single cells were resuspended in warm media with 10 μg/mL of GlucBio at 1 M cells/mL. After incubated at 37° C. for 30 min and washed with cold PBS for 3 times, the collected cell pellet was resuspended in serum-free, biotin-free media which contained 25 U/mL lactate dehydrogenase (LDH) and 25 U/mL diaphorase. The concentration of the as-prepared single cell suspension was 1 M cells/mL.

Single Cell Metabolic/Proteomic Measurements

The single cell barcode chips (SCBC) were fabricated according to well-established procedures. DNA-encoded antibody library (DEAL) was grafted onto the surface through DNA hybridization to afford capture antibody arrays. The DNA-APRz conjugate can also be incorporated onto the surface barcode through the same procedure. The devices were operated following previously established protocols (see, e.g., Xue et al. (2015) *J. Am. Chem. Soc.,* 137:4066-4069; Xue et al. (2016) *J. Am. Chem. Soc.* 138:3085-3093 with two modification: 1) cells were loaded and segregated in individual chambers and the devices were incubated at 37° C. for 30 min to allow lactate secretion. 2) the lysis buffer was prepared to contain 2 mM of $NAD^+$.

Statistical Analysis

The SCBC readouts from the microchambers with single cells were collected to form a data table. Each row of the table corresponds to a measurement of a panel of functional proteins from a single cell and each column contains digitized fluorescence intensities that provide readout of the levels of each of the assayed proteins. To calculate the analyte-analyte correlations, random downsampling was performed first to create a balanced dataset with equal number of single cell measurements in control, erlotinib and oligomycin conditions. Protein-protein Spearman's rank correlation coefficients were calculated. Bonferroni corrected p-value was used to define the statistical significance level for the entire panel and only those significant correlations were shown in the networks. Analyte-analyte correlation networks were generated by running the calculation through all the analyte pairs in panel.

Phenograph, t-SNE and SARA Analyses.

Phenograph and t-SNE dimensionality reduction analysis was performed on SCBC dataset following previously published algorithms (see, e.g., Amir, et. al. (2013) *Nat. Biotech.* 31:545-552). Single cell data were transformed using hyperbolic arcsin with a cofactor of five. In the Phenograph construction, ten nearest neighbors (k=10) were identified for each single cell using Euclidean distance.

SARA analysis was performed on the single cell dataset for quantifying signaling responses to perturbations following previous published algorithm. SARA examines the entire single cell fluctuations of analyte levels to detect meaningful changes between two conditions. The algorithm performs random permutations to estimate the statistical significance of the signaling responses, and generates a score based upon the Mallow's distance of two single cell distributions.

Drug Synergy Measurements

For the cell counting assay, 500K cells were suspended in 10 mL of media and cultured for 24 hrs. Then, the medium was changed to 10 mL of fresh media containing various concentrations of erlotinib, oligomycin A, metformin and phenfomin. Cells were cultured for 72 hrs, during which time the drugs were replenished every 24 h. The cell numbers from each culturing condition were counted and normalized to the control sample.

For the resazurin assay, 100 μL of 10 μg/mL laminin was added into each well of a 96-well plate and the plate was incubated at 37° C. overnight. Then, the laminin solution was removed and 20,000 of GBM 39 cells suspended in 200 μL of media was added into each well. After a 24 h incubation to ensure the cell attachment, media were changed to 200 μL of fresh ones containing various concentrations of erlotinib and oligomycin A. The cells were cultured for another 72 hrs and the drugs were replenished every 36 hrs. Subsequently, 20 μL of 0.2 mg/mL resazurin PBS solution was added into each well, followed by incubation at 37° C. for 4 hrs. The resulting fluorescent signals were recorded by a plate reader (560 nm excitation/590 nm emission).

The synergy score of the two drugs was calculated by using the following equation:

$$S_{A,B} = I_{A,B} - (I_A + I_B - I_A \times I_B)$$

where $S_{A,B}$ is the synergy effect between drugs A and B, $I_{A,B}$ is the cell killing efficiency by using the combination of drug A and B while $I_A$ and $I_B$ are the cell killing efficiencies from independent doses of drug A or B, respectively. The numbers presented in FIG. 4 are the excess activity percentage under the Bliss independence assumption.

References.

[1] a) Ito & Suda (2014) *Nat. Rev. Mol. Cell Biol.* 15:243-256; b) Kohli & Passegué (2014) *Trend. Cell Biol.* 24:479-487; c) Cairns et al. (2011) *Nat. Rev. Cancer,* 11:85-95.

[2] Hanahan & Weinberg (2011) *Cell,* 144:646-674.

[3] Locasale & Cantley (2011) *Cell Metab.* 14:443-451.

[4] a) Amir et al. (2013) *Nat. Biotech.* 31:545-552; b) McGranahan & Swanton (2017) *Cell,* 168:613-628.

[5] Xue et al. (2015) *J. Am. Chem. Soc.,* 137:4066-4069.

[6] Lunt & Heiden (2011) *Anmi. Rev. Cell Dev. Biol.* 27:441-464.

[7] Xue et al. (2016) *J. Am. Chem. Soc.* 138:3085-3093.

[8] Hitosugi (2013) *J. Chen, Oncogene,* 33:4279.

[9] a) O'Brien et al. (2000) *Eur. J. Biochem.* 267:5421-5426; b) Palomino et al. (2002) *Antimicrob. Agents Chemother.* 46:2720-2722; c) Candeias et al. (1998) *J. Chem. Soc., Perkin Trans.* 2:2333-2334.

[10] Jewett & Bertozzi (2010) *Chem. Soc. Rev.* 39:1272-1279.

[11] a) Zhao et al. (2011) *Cell Metab.* 14:555-566; b) Eyer et al. (2012) *Lab Chip,* 12:765-772.

[12] Zheng et al. (2010) *Anal. Chem.* 82:5082-5087.

[13] Park et al. (2012) *Biochem. J.* 448:417-423.

[14] TeSlaa & Teitell (2014) *Meth. Enzymol.* 542:91-114.

[15] a) Levine et al. (2015) *Cell,* 162:184-197; b) Bendall et al. (2014) *Cell,* 157:714-725.

Example 2

Protocol for Quantifying D-2-Hydroxylglutarate (D2HG) Using BT142 Cells

1. Preparation of Streptavidin (SAC)-DNA conjugate:
    1.1 Desalt SAC (100 μl, 1 mg/ml, 20 μM) in 5 mM TCEP (i.e., Tris(2-carboxyethyl) phosphine)/PBS twice by column.
    1.2 Prepare 100 mM MHPH (i.e., Maleimide HyNic) and 100 mM S4FB (i.e., succinimidyl 4-formylbenzoate) stock solutions in anhydrous DMF.
    1.3 Mix 100 μl purified SAC with 6 μl of MHPH and 6 μl of DMF, and then react for 3-4 hours at room temperature.

1.4 Mix 80 μl DNA stock (500 μM) with 20 μl of S4FB and 15 μl of DMF, and then react for 3-4 hours at room temperature.

1.5 Process the reacted SAC and DNA solutions with buffer exchange by using citrate buffer (50 mM citrate+150 mM NaCl, pH 6.0) twice.

1.6 Combine the two resultant solutions and react overnight at room temperature.

1.7 Purify the obtained conjugate with Fast protein liquid chromatography (FPLC).

2. Couple the DNA-barcoded slide with PDMS template to form an integrated PDMS device for 2HG bulk assay.

3. Dilute the SAC-DNA conjugate with 1% BSA solution with the ration of 1:100. Then, 25 μL of the resultant SAC-DNA conjugate is added into the microwell of the formed PDMS device and then incubate at 37° C. for 1 h.

4. Prepare 10 μM BPRz stock solution by dissolving BPRz powder into 1% BSA solution.

5. Suck up the conjugate and wash the microwell with 1×PBST solution for three times.

6. Add 25 μL of 10 μM BPRz solution into the microwell and then incubate at 37° C. for 1 h.

7. Meanwhile, cultured cells are collected and lysed with 1× cell lysis buffer containing 1× protease and phosphatase inhibitor.

8. Centrifuge the cell lysate at 18000 g for 10 min at 4° C.

9. After the second 1 h incubation, suck up the BPRz solution and wash the microwell with 1×PBTS for three time.

10. Add 25 μL of the supernatant of the centrifuged cell lysate into the microwell, followed by the addition of 1 μL of D-2-hydroxyglutarate dehydrogenase (D2HGDH) solution (1 mg/mL), and 1 μL of NAD$^+$ solution (10 mM). To obtain the calibration curve of the D2HG assay, 25 μL of standard D2HG solution with various concentrations are also added into different microwells of the PDMS device, followed by the addition of 1 μL of D2HGDH solution, and 1 μL of NAD$^+$ solution into each microwell. Incubate the PDMS device at 37° C. for 1 h.

11. Such up the solutions inside the microwells and wash them with 1×PBST for three times.

12. Peel off the PDMS template and in turn wash the DNA-barcoded slide with 1×PBS, 0.5×PBS, DI water and DI water. Finally, spin dry to remove the water on the slide.

13. Scan the slide with Genepix microarray scanner.

Figure 37:
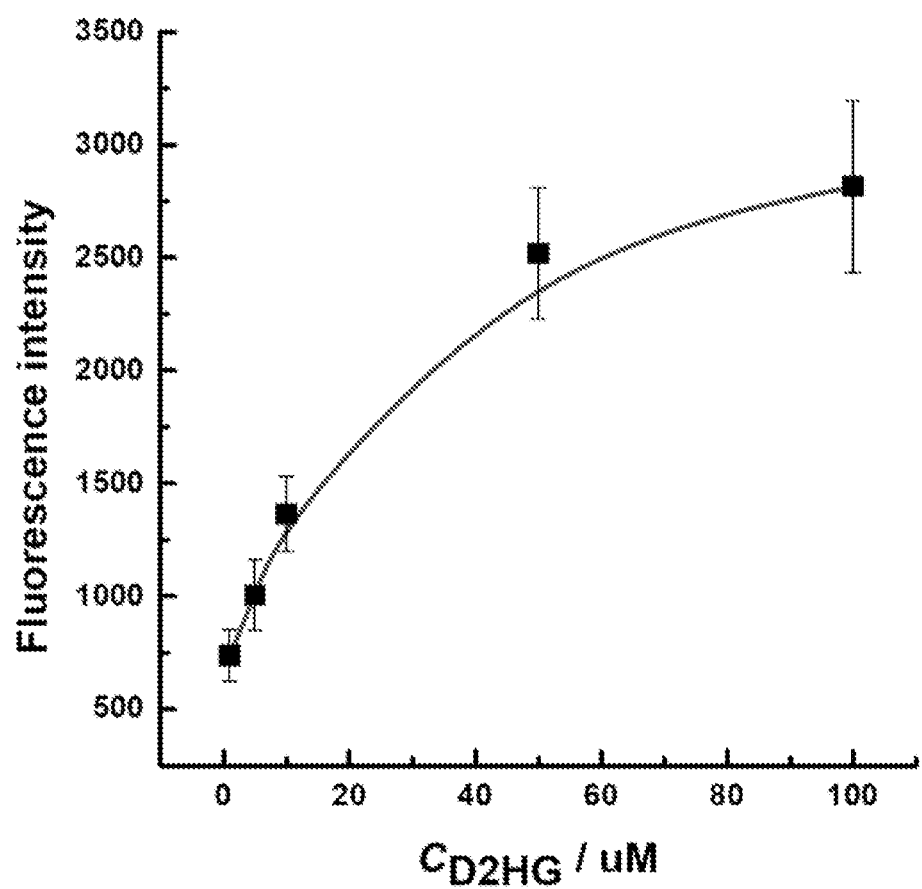
FIG. 37. Calibration curve of D2HG using standard D2HG solution. The measured fluorescence intensity of BT42mut lysate is ca. 2114.

FIG. 37 illustrates a calibration curve of D2HG using standard D2HG solution. The measured fluorescence intensity of BT42mut lysate is ca. 2114.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A compound, which has a redox-active resazurin moiety, wherein said compound is selected from the group consisting of

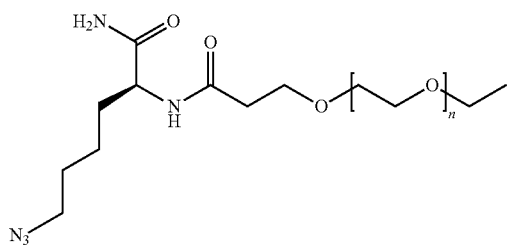

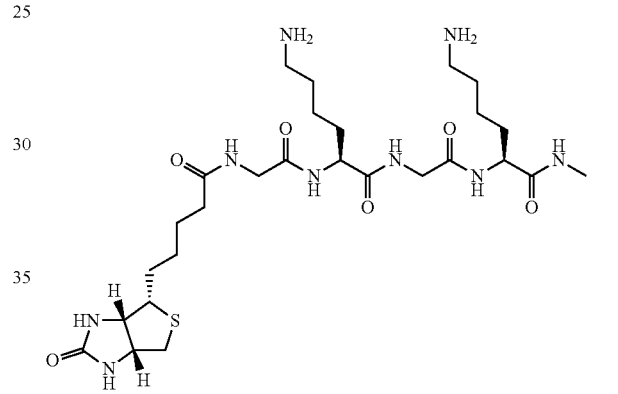

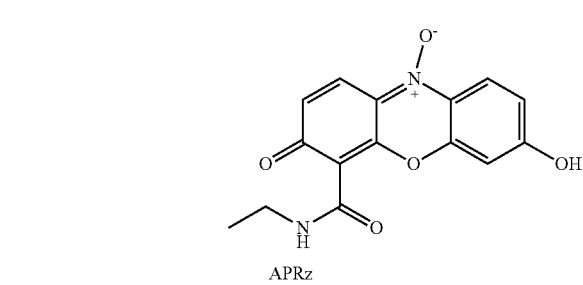

APRz

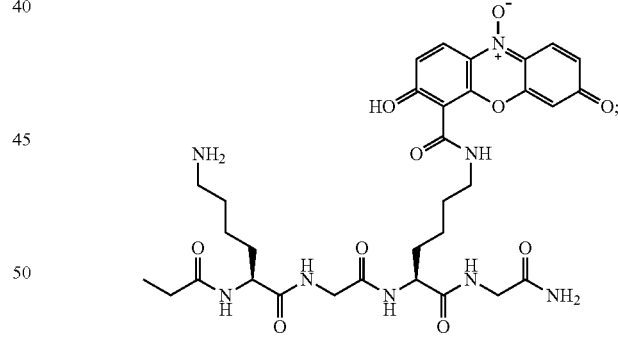

BRz

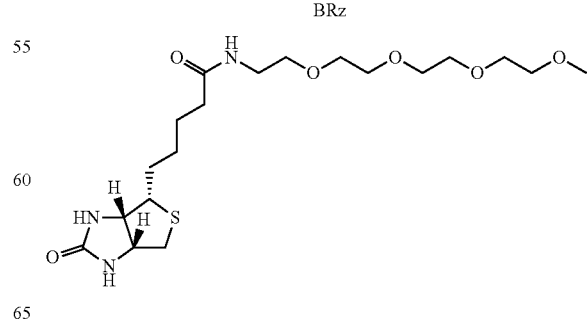

wherein n is 2 to 24;

-continued

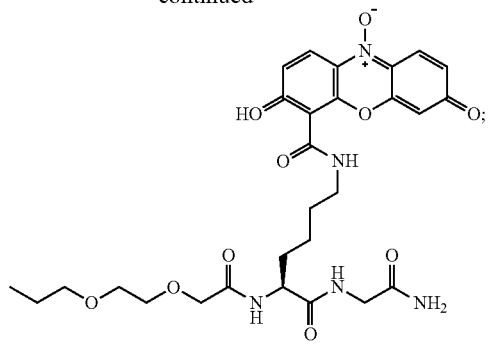

BPRz
Biotin-PEG5-K(Rz)-G

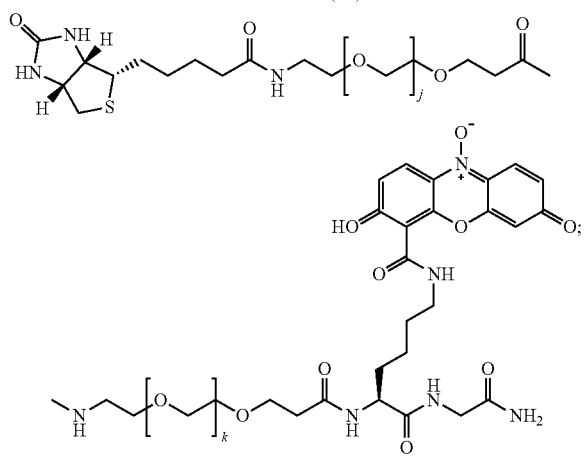

wherein j and k are independently 2-46; and

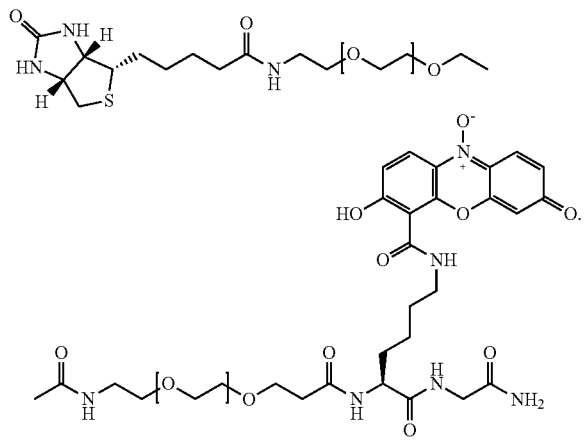

BP2Rz
Biotin-PEG48-K(Rz)-G

2. A composition comprising the compound according to claim 1 in an aqueous solution.

3. The composition according to claim 2, further comprising nicotine adenine dinucleotide (NAD), nicotine adenine dinucleotide phosphate (NADP), or both.

4. The composition according to claim 2, further comprising a diaphorase.

5. The composition according to claim 2, further comprising a lactate dehydrogenase.

6. An assay device, which comprises a solid surface and the compound according to claim 1 immobilized on the solid surface.

7. The assay device according to claim 6, wherein the compound is immobilized on the solid surface via a linker, wherein said linker comprises avidin, streptavidin, or a diarylcyclooctyne moiety.

8. The assay device according to claim 7, wherein the linker further comprises a nucleic acid molecule.

9. The assay device according to claim 7, wherein the diarylcyclooctyne moiety is dibenzylcyclooctyne (DBCO).

10. The assay device according to claim 8, wherein the nucleic acid molecule is hybridized to a second nucleic acid molecule that is immobilized on the solid surface.

11. The assay device of claim 6, wherein the solid surface is
    a surface of a microfluidic device;
    a surface of a microchannel or a microwell;
    a surface of an elastomeric microfluidics device; or
    a surface of a microchamber in a single cell barcode device.

12. The assay device of claim 11, further comprising a lysis buffer reservoir.

13. The assay device of claim 12, wherein a valve separates the lysis buffer reservoir from the microwell or the microchamber.

14. The assay device of claim 11, wherein the microwell or the microchamber comprises a DNA barcode stripe.

15. A method of detecting and/or quantifying an analyte, which is reducible or oxidizable, in a single cell, which comprises
    optionally lysing the single cell to obtain a lysate;
    contacting the single cell or the lysate with the compound according to claim 1 in the presence of an NAD moiety, which is nicotine adenine dinucleotide (NAD) or nicotine adenine dinucleotide phosphate (NADP), and enzyme(s) that enzymatically couple the oxidation or reduction of the analyte with the oxidation or reduction of the redox-active moiety; and
    detecting a change in fluorescence of the redox-active resazurin moiety, wherein said change in fluorescence indicates the presence of the analyte and the amount of fluorescence indicates the quantity of the analyte.

16. The method according to claim 15, wherein the compound is immobilized on a solid surface of an assay device.

17. The method according to claim 16, wherein the compound is immobilized on the solid surface via a linker which comprises avidin, streptavidin, or a diarylcyclooctyne moiety.

18. The method according to claim 17, wherein the linker further comprises a nucleic acid molecule.

19. The method according to claim 17, wherein the diarylcyclooctyne moiety is dibenzylcyclooctyne (DBCO).

20. The method according to claim 18, wherein the nucleic acid molecule is hybridized to a second nucleic acid molecule that is immobilized on the solid surface.

21. The method according to claim 15, wherein the enzymes comprise a diaphorase.

22. The method according to claim 15, wherein the enzymes comprise a lactate dehydrogenase.

23. The method according to claim 15, wherein the analyte is lactate, formate, glutamate, triacylglyceride, hydroxylglutarate, malate, fumarate, succinate, or citrate.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial
<220> FEATURE:
<223> OTHER INFORMATION: Peptide linker

<400> SEQUENCE: 1

Gly Lys Gly Lys Gly Lys
1               5

<210> SEQ ID NO 2
<211> LENGTH: 4
<212> TYPE: PRT
<213> ORGANISM: Artificial
<220> FEATURE:
<223> OTHER INFORMATION: Peptide linker

<400> SEQUENCE: 2

Gly Lys Gly Lys
1

<210> SEQ ID NO 3
<211> LENGTH: 8
<212> TYPE: PRT
<213> ORGANISM: Artificial
<220> FEATURE:
<223> OTHER INFORMATION: Peptide linker

<400> SEQUENCE: 3

Gly Lys Gly Lys Gly Lys Gly Lys
1               5
```

```
<210> SEQ ID NO 4
<211> LENGTH: 10
<212> TYPE: PRT
<213> ORGANISM: Artificial
<220> FEATURE:
<223> OTHER INFORMATION: Peptide linker

<400> SEQUENCE: 4

Gly Lys Gly Lys Gly Lys Gly Lys Gly Lys
1               5                   10

<210> SEQ ID NO 5
<211> LENGTH: 12
<212> TYPE: PRT
<213> ORGANISM: Artificial
<220> FEATURE:
<223> OTHER INFORMATION: Peptide linker

<400> SEQUENCE: 5

Gly Lys Gly Lys Gly Lys Gly Lys Gly Lys Gly Lys
1               5                   10
```